US006458889B1

(12) United States Patent
Trollsas et al.

(10) Patent No.: US 6,458,889 B1
(45) Date of Patent: *Oct. 1, 2002

(54) COMPOSITIONS AND SYSTEMS FOR FORMING CROSSLINKED BIOMATERIALS AND ASSOCIATED METHODS OF PREPARATION AND USE

(75) Inventors: Olof Mikael Trollsas, Los Gatos; Donald G. Wallace, Menlo Park; Frank A. DeLustro, Belmont, all of CA (US)

(73) Assignee: Cohesion Technologies, Inc., Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/883,138

(22) Filed: Jun. 15, 2001

Related U.S. Application Data

(63) Continuation-in-part of application No. 09/733,739, filed on Dec. 8, 2000, now Pat. No. 6,323,278, and a continuation-in-part of application No. 09/649,337, filed on Aug. 28, 2000, which is a continuation of application No. 09/302,852, filed on Apr. 30, 1999, now Pat. No. 6,166,130, which is a continuation of application No. 09/229,851, filed on Jan. 13, 1999, now Pat. No. 6,051,648, which is a continuation of application No. 08/769,806, filed on Dec. 18, 1996, now Pat. No. 5,874,500, which is a continuation-in-part of application No. 08/573,799, filed on Dec. 18, 1995, now abandoned.

(60) Provisional application No. 60/151,273, filed on Aug. 27, 1999.

(51) Int. Cl.[7] ............... C08F 283/00; C08G 63/91; C08G 63/48
(52) U.S. Cl. ............... 525/54.1; 525/419; 525/420; 525/425
(58) Field of Search ............... 525/54.1, 419, 525/420, 425

(56) References Cited

U.S. PATENT DOCUMENTS

| | | | |
|---|---|---|---|
| 3,619,371 A | 11/1971 | Crook et al. |
| 3,742,955 A | 7/1973 | Battista et al. |
| 3,788,948 A | 1/1974 | Kegadal et al. |
| 3,810,473 A | 5/1974 | Cruz, Jr. et al. |
| 3,876,501 A | 4/1975 | Hanushewsky |
| 3,949,073 A | 4/1976 | Daniels et al. |
| 3,960,830 A | 6/1976 | Bayer et al. |
| 4,002,531 A | 1/1977 | Royer |
| 4,055,635 A | 10/1977 | Green et al. |
| 4,088,538 A | 5/1978 | Schneider |
| 4,101,380 A | 7/1978 | Rubinstein et al. |
| 4,164,559 A | 8/1979 | Miyata et al. |
| 4,179,337 A | 12/1979 | Davis et al. |
| 4,192,021 A | 3/1980 | Deibig et al. |
| 4,237,229 A | 12/1980 | Hartdegen et al. |
| 4,238,480 A | 12/1980 | Sawyer |
| 4,261,973 A | 4/1981 | Lee et al. |

(List continued on next page.)

FOREIGN PATENT DOCUMENTS

| | | |
|---|---|---|
| CA | 2134744 | 5/1995 |
| EP | 0013249 | 1/1980 |
| EP | 0042253 | 12/1981 |
| EP | 00154447 | 9/1985 |
| EP | 0157359 | 10/1985 |
| EP | 0171176 | 2/1986 |
| EP | 0243179 | 10/1987 |
| EP | 0330389 | 8/1989 |
| EP | 0341007 | 11/1989 |
| EP | 4-227265 | 4/1990 |
| EP | 0431479 A1 | 6/1991 |

(List continued on next page.)

OTHER PUBLICATIONS

Braatz et al. (1992), "A New Hydrophilic Polymer for Biometrial Coatings with Low Protein Adsorption," *J. Biomater. Sci. Polymer Edn.* 3(6):451–462.

Dreborg et al. (1990), "Immunotherapy with Monomethoxypolyethylene Glycol Modified Allergens," *Critical Reviews in Therapeutic Drug Carrier Systems* 6(4):315–365.

Lichtenwalner et al. (1970), Encyclopedia of Polymer Science and Technology 12:535, Eds. Mark, Gaylord and Bikales, John Wiley, NY.

Nakayama et al. (1999), "Photocurable Surgical Tissue Adhesive Glues Composed of Photoreactive Gelatin and Poly(Ethylene Glycol) Diacrylate,"*Journal of Biomedical Materials Research (Applied Biomaterials)* 48(4):511–521.

Ouchi et al. (1987), "Synthesis of 5–Fluorouracil–Terminated Monomethoxypoly(Ethylene Glycol)s, Their Hydrolysis Behavior, and Their Antitumor Activities," *J. Macromol. Sci.–Chem. A24*(9):1011–1032.

(List continued on next page.)

*Primary Examiner*—Nathan M. Nutter
(74) *Attorney, Agent, or Firm*—Reed & Associates; Dianne E. Reed

(57) ABSTRACT

Crosslinkable compositions are provided that readily crosslink in situ to provide biocompatible, nonimmunogenic crosslinked biomaterials. The compositions contain at least three biocompatible, nonimmunogenic components having reactive functional groups thereon, with the functional groups selected so as to enable inter-reaction between the components, i.e., crosslinking. In a preferred embodiment, a first component is polynucleophilic, a second component is polyelectrophilic, and at least one third component contains one or more functional groups reactive with the nucleophilic moieties one the first or second component. At least one of the components is a polyfunctional hydrophilic polymer; the other components may also comprise hydrophilic polymers, or they may be low molecular weight, typically hydrophobic, crosslinkers. Methods for preparing and using the compositions are also provided. Exemplary uses include tissue augmentation, biologically active agent delivery, bioadhesion, and prevention of adhesions following surgery or injury.

74 Claims, 19 Drawing Sheets

U.S. PATENT DOCUMENTS

| | | |
|---|---|---|
| 4,279,812 A | 7/1981 | Cioca |
| 4,301,144 A | 11/1981 | Iwashita et al. |
| 4,314,380 A | 2/1982 | Miyata |
| 4,320,201 A | 3/1982 | Berg et al. |
| 4,357,274 A | 11/1982 | Werner |
| 4,390,519 A | 6/1983 | Sawyer |
| 4,404,970 A | 9/1983 | Sawyer |
| 4,412,947 A | 11/1983 | Cioca |
| 4,412,989 A | 11/1983 | Iwashita |
| 4,414,147 A | 11/1983 | Klibanov et al. |
| 4,415,628 A | 11/1983 | Cioca et al. |
| 4,415,665 A | 11/1983 | Mosbach et al. |
| 4,424,208 A | 1/1984 | Wallace et al. |
| 4,451,568 A | 5/1984 | Sneider et al. |
| 4,488,911 A | 12/1984 | Luck et al. |
| 4,495,285 A | 1/1985 | Shimizu et al. |
| 4,496,689 A | 1/1985 | Mitra |
| 4,515,637 A | 5/1985 | Cioca |
| 4,544,516 A | 10/1985 | Hughes et al. |
| 4,553,974 A | 11/1985 | Dewanjee |
| 4,557,764 A | 12/1985 | Chu |
| 4,563,350 A | 1/1986 | Nathan et al. |
| 4,563,351 A | 1/1986 | Nathan et al. |
| 4,563,490 A | 1/1986 | Stol et al. |
| 4,578,067 A | 3/1986 | Cruz, Jr. |
| 4,582,640 A | 4/1986 | Smestad et al. |
| 4,592,864 A | 6/1986 | Miyata et al. |
| 4,600,533 A | 7/1986 | Chu |
| 4,642,117 A | 2/1987 | Nguyen |
| 4,655,980 A | 4/1987 | Chu |
| 4,670,417 A | 6/1987 | Iwasaki et al. |
| 4,678,468 A | 7/1987 | Hiroyoshi |
| 4,687,820 A | 8/1987 | Hou et al. |
| 4,689,399 A | 8/1987 | Chu |
| 4,695,602 A | 9/1987 | Crosby et al. |
| 4,703,108 A | 10/1987 | Silver et al. |
| 4,704,131 A | 11/1987 | Noishiki et al. |
| 4,725,671 A | 2/1988 | Chu et al. |
| 4,732,863 A | 3/1988 | Tomasi |
| 4,737,544 A | 4/1988 | McCain et al. |
| 4,745,180 A | 5/1988 | Moreland et al. |
| 4,766,106 A | 8/1988 | Katre |
| 4,774,227 A | 9/1988 | Piez et al. |
| 4,789,663 A | 12/1988 | Wallace et al. |
| 4,795,467 A | 1/1989 | Piez et al. |
| 4,828,563 A | 5/1989 | Müller-Lierheim |
| 4,847,325 A | 7/1989 | Shadle et al. |
| 4,851,513 A | 7/1989 | Devore et al. |
| 4,886,866 A | 12/1989 | Braatz et al. |
| 4,935,465 A | 6/1990 | Garman |
| 4,950,483 A | 8/1990 | Ksander |
| 4,950,699 A | 8/1990 | Holman |
| 4,973,493 A | 11/1990 | Guire |
| 4,979,959 A | 12/1990 | Guire |
| 4,980,403 A | 12/1990 | Bateman et al. |
| 4,983,580 A | 1/1991 | Gibson |
| 5,024,742 A | 6/1991 | Nesburn et al. |
| 5,108,957 A | 4/1992 | Kelman et al. |
| 5,122,614 A | 6/1992 | Zalipsky |
| 5,141,747 A | 8/1992 | Scholz |
| 5,156,613 A | 10/1992 | Sawyer |
| 5,162,430 A | 11/1992 | Rhee et al. |
| 5,167,960 A | 12/1992 | Ito et al. |
| 5,169,754 A | 12/1992 | Siiman et al. |
| 5,192,316 A | 3/1993 | Ting |
| 5,198,493 A | 3/1993 | Holmberg et al. |
| 5,201,764 A | 4/1993 | Kelman et al. |
| 5,209,776 A | 5/1993 | Bass et al. |
| 5,219,564 A | 6/1993 | Zalipsky et al. |
| 5,219,895 A | 6/1993 | Kelman et al. |
| 5,264,214 A | 11/1993 | Rhee et al. |
| 5,290,552 A | 3/1994 | Sierra et al. |
| 5,292,802 A | 3/1994 | Rhee et al. |
| 5,298,643 A | 3/1994 | Greenwald |
| 5,304,595 A | 4/1994 | Rhee et al. |
| 5,306,500 A | 4/1994 | Rhee et al. |
| 5,308,889 A | 5/1994 | Rhee et al. |
| 5,321,095 A | 6/1994 | Greenwald |
| 5,324,775 A | 6/1994 | Rhee et al. |
| 5,324,844 A | 6/1994 | Zalipsky |
| 5,328,955 A | 7/1994 | Rhee et al. |
| 5,349,001 A | 9/1994 | Greenwald et al. |
| 5,354,336 A | 10/1994 | Kelman et al. |
| 5,364,622 A | 11/1994 | Franz et al. |
| 5,405,877 A | 4/1995 | Greenwald et al. |
| 5,410,016 A | 4/1995 | Hubbell et al. |
| 5,428,022 A | 6/1995 | Palefsky et al. |
| 5,455,027 A | 10/1995 | Zalipsky et al. |
| 5,475,052 A | 12/1995 | Rhee et al. |
| 5,510,418 A | 4/1996 | Rhee et al. |
| 5,514,379 A | 5/1996 | Weissleder et al. |
| 5,549,904 A | 8/1996 | Juergensen et al. |
| 5,565,519 A | 10/1996 | Rhee et al. |
| 5,567,422 A | 10/1996 | Greenwald |
| 5,580,923 A | 12/1996 | Yeung et al. |
| 5,605,976 A | 2/1997 | Martinez et al. |
| 5,612,460 A | 3/1997 | Zalipsky |
| 5,614,549 A | 3/1997 | Greenwald et al. |
| 5,614,587 A | 3/1997 | Rhee et al. |
| 5,626,863 A | 5/1997 | Hubell et al. |
| 5,637,749 A | 6/1997 | Greenwald |
| 5,643,464 A | 7/1997 | Rhee et al. |
| 5,643,575 A | 7/1997 | Martinez et al. |
| 5,667,839 A | 9/1997 | Berg |
| 5,681,904 A | 10/1997 | Manzara |
| 5,700,848 A | 12/1997 | Soon-Shiong et al. |
| 5,752,974 A | 5/1998 | Rhee et al. |
| 5,786,421 A | 7/1998 | Rhee et al. |
| 5,874,500 A * | 2/1999 | Rhee et al. ............... 525/54.1 |
| 6,051,648 A | 4/2000 | Rhee et al. |
| 6,166,130 A | 12/2000 | Rhee et al. |
| 6,217,894 B1 | 4/2001 | Sawhney et al. |

FOREIGN PATENT DOCUMENTS

| | | |
|---|---|---|
| EP | 0466383 | 1/1992 |
| EP | 0575273 | 12/1993 |
| EP | 0640647 | 3/1995 |
| EP | 0656214 | 6/1995 |
| EP | 0656215 | 6/1995 |
| EP | 0680990 | 11/1995 |
| EP | 0732109 | 9/1996 |
| FR | 2628634 | 9/1989 |
| GB | 1059455 | 2/1967 |
| JP | 60-70972 | 3/1994 |
| JP | 07-090241 | 4/1995 |
| WO | WO 84/01106 | 3/1984 |
| WO | WO 95/04412 | 10/1985 |
| WO | WO 87/04078 | 7/1987 |
| WO | WO 90/05755 | 5/1990 |
| WO | WO 92/13025 | 8/1992 |
| WO | WO 92/13578 | 8/1992 |
| WO | WO 94/01483 | 1/1994 |
| WO | WO 94/03155 | 2/1994 |
| WO | WO 97/22371 | 6/1997 |
| WO | WO 99/07417 | 2/1999 |
| WO | WO 00/33764 | 6/2000 |
| WO | WO 00/44808 | 8/2000 |
| WO | WO 00/62827 | 10/2000 |

OTHER PUBLICATIONS

Prior et al. (1999), "A Sprayable Hemostat Containing Fibrillar Collagen, Bovine Thrombin, and Autologous Plasma," *Ann. Thorac. Surg.* 68:479–485.

Zalipsky et al. (1983), "Attachment of Drugs to Polyethylene Glycols," *Eur. Polym. J.* 19(12):1177–1183.

Zalipsky et al. (1987), "A Convenient General Method for Synthesis of $N^{\alpha}$–$N^{\omega}$–Dithiasuccinoyl (Dts) Amino Acids and Dipeptides: Application of Polyethylene Glycol as a Carrier for Functional Purification,"*Int. J. Peptide Protein Res.* 30:740–783.

Zheng et al. (199), "Production of Microspheres with Surface Amino Groups from Blends of Poly(Lactide–co–Glycolide) and Poly($\epsilon$–CBZ–L–Lysine) and Use for Encapsulation, " *Biotechnol. Progr.* 15:763–767.

Poly(Eethylene Glycol) Chemistry: Biotechnical & Biomedical Applications, Chapter 22, J. Milton Harris, Ed., Plenum Press, NY (1992).

Abuchowski et al. (1977), "Alteration of immunological properties of bovine serum albumin by covalent attachment of polyethylene glycol," *Biol. Chem.* 252(11):3578–3581.

Abuchowski et al. (1984), "Cancer therapy with chemically modified enzymes. I. Antitumor properties of polyethylene glycol–asparaginase conjugates," *Cancer Biochem. Biophys.* 7:175–186.

Abuchowski et al. (1977), "Effect of covalent attachment of polyethylene glycol on immunogenicity and circulating life of bovine liver catalase," *J. Biol. Chem.* 252(11):3582–3586.

Anderson et al. (1964), "The use of esters of n–hydroxysuccinimide in peptide synthesis," [???] 86:1839–1842.

Beauchamp et al. (1983), "A new procedure for the synthesis of polyethylene glycol–potein adducts: Effects on fuction, receptor recognition, and clearance of superoxide dismutase, lactoferrin, and $a_2$–macroglobulin," *Analytical Biochemistry* 131:25–33.

Bendich et al. (1982), "Immunological effects of native and polyethylene glycol–modified asparaginases from *Vibro succinogenes* and *Escherichia coli* in normal and tumor–bearing mice," *Clin. Exp. Immunol.* 48:273–278.

Chen et al. (1981), "Properties of two urate oxidases modified by the covalent attachment of poly(ethylene glycol)," *Biochem. Biophys. Acta.* 660:293–298.

Chvapil et al. (1969), "Some chemical and biological characteristics of a new collagen–polymer compound material," *J. Biomed. Mater. Res.* 3:315–332.

Davis et al. (1981), "Hypouricaemic effect of polyethyleneglycol modified urate oxidase," *Lancet* 2:281–283.

Doillon et al. (1986), *J. Biomed. Mat. Res.* 20(8):1219–1228.

Ferruti (1981), "Succinic half–esters of poly(ethylene glycol)s and their benzotriazole and imidazole derivatives as oligomeric drug–binding matrices," *Makromol. Chem.* 182:2183–2192.

Fleisher et al. (1987), "Regeneration of lost attachment apparatus in the dog using polygalactin–910," *J. Dent. Res.* 281(66 spec.), Abstract No. 1393.

Gander et al. (1988). "Crosslinked poly(alkylene oxides) for the preparation of controlled release micromatrices," *J. Controlled Release* 5:271–283.

Gnanou et al. (1984), "Hydrophilic polyurethane networks based on poly(ethylene oxide): Synthesis, characterization, and properties. Potential applications as biomaterials," *Macromolecules* 17:945–952.

Gomel et al. (1992), "Inferetility surgery: Microsurgery," *Current Opinion in Obstetrics and Gynecology* 4:390–399.

Inada et al. (1984), "Ester synthesis catalyzed by polyethylene glycol–modified lipase in benzxene," *Biochem. & Biophys. Res. Comm.* 122:845–850.

Katre et al. (1987), "Chemical modification of recombinant interleukin 2 by polyethylene glycol increases its potency in the murine meth A sarcoma model," *Proc. Natl. Acad. Sci. USA* 84:1487–1491.

McPherson et al. (1988), *Collagan and Related Research Clinical and Experimental* 8(1):83–100.

Nathan et al. (199), "Copolymers of lysine and polyethylene glycol: A new family of functionalized drug carriers," *Bioconjugate Chem.* 4:54–62.

Nishida et al. (1984), "Hypouricaemic effect after oral administration in chickens of polyethylene glycol–modified uricase entrapped in liposomes," *J. Pharm. Pharmacol.* 36:354–355.

Pados et al. (1992), "Adhesions," *Current Opinion in Obstetrics and Gynecology* 4:421–428.

Pagidas et al. (1992), "Effects of Ringer's lactate, interceed (TC7) and gore–tex surgical membrane on postsurgical adhesion formation," *Fertility and Sterility* 57(1):199–201.

Pyatak et al. (1980), "Preparation of a polyethylene glycol: siperoxide dismutase adduct, and an examination of its blood circulating life and anti–inflammatory activity," *Res. Com. Chem. Path. Pharmacol.* 29:113–127.

Ramshaw et al. (1984), "Precipitation of collagens by polyethylene glycols," *Anal. Biochem.* 141:361–365.

Savoca et al. (1979), "Preparation of a non–immunigenic arginase by the covalent attachment of polyethylene glycol," *Biochem. Biophys. Acta.* 578:47–53 (1979).

Sawhney et al. (1994), "Optimization of photopolymerized bioerodible hydrogel properties for adhesion prevention," *J. Biomed. Mat. Res.* 28:831–838.

Sperinde et al. (1997), "Phase transformation poly(ethylene glycol) hydrogels for tissue engineering and cell therapies," $23^{rd}$ *Annual Meeting of the Society for Biomaterials*, p. 247.

Steinleitner et al. (1991), "Poloxamer 407 as an intraperitoneal barrier material for the prevention of postsurgical adhesion formation and reformation in rodent models for reproductive surgery,"*Obstetrics and Gynecology* 77:48–52.

Takahashi et al. (1984), "A chemical modification to make horseradish peroxidase soluable and active in benzene," *Biochem. & Biophys. Res. Comm.* 121:261–265.

Tulandi (1991), "Effects of fibrin sealant on tubal anastomosis and adhesion formation," *Fertility and Sterility* 56(1):136–138.

Ulbrich et al. (1986), "Poly(ethylene glycol)s containing enzymatically degradable bonds," *Makromol. Chem.* 187:1131–1144.

Urman et al. (1991), "Effect of hyaluronic acid on postoperative intraperitoneal adhesion formation and reformation in the rat model," *Fertility and Sterility* 56(3):568–570.

Viau et al. (1986), "Safety evaluation of free radical scavengers PEG–catalase and PEG–superoxide dismutase," *J. Free Rad. In Bio. & Med.* 2:283–288.

Viau et al. (1986), "Toxicologic studies of a conjugate of asparaginase and polyethylen glycol in mice, rats and dogs," *Am. J. Vet. Res.* 47:1398–1401.

West et al. (1995), "Comparison of covalently and physically cross–linked polyethylene glycol–based hydrogels for the prevention of postoperative adhesions in a rat model," *Biomaterials* 16:1153–1156.

Wieder et al. (1979), "Some properties of polyethylene glycol: Phenylalanine ammonia–lyase adducts," *J. Biol. Chem.* 254:12579–12587.

U.S. patent application Ser. No. 08/573,799, Rhee et al., filed Dec. 18, 1995.

U.S. patent application Ser. No. 09/649,337, Wallace et al., filed Aug. 28, 2000.

U.S. patent application Ser. No. 09/733,739, Rhee et al., filed Dec. 8, 2000.

Kroschwitz (1990), Concise Encyclopedia of Polymer Science and Engineering, Wiley Intersciences Edition, New York, NY, p. 489.

* cited by examiner

SSA-PEG, m=2: Tetrafunctionally Activated PEG Succinimidyl Succinamide

COMPOSITIONS AND SYSTEMS FOR FORMING CROSSLINKED BIOMATERIALS AND ASSOCIATED METHODS OF PREPARATION AND USE

CROSS-REFERENCE TO RELATED APPLICATIONS

This application is a continuation-in-part of U.S. application Ser. No. 09/733,739, filed Dec. 8, 2000, now U.S. Pat. No. 6,323,278, which is a continuation of U.S. application Ser. No. 09/302,852, filed Apr. 30, 1999 and issued as U.S. Pat. No. 6,166,130 on Dec. 26, 2000, which was a continuation of U.S. application Ser. No. 09/229,851, filed Jan. 13, 1999 and issued as U.S. Pat. No. 6,051,648 on Apr. 18, 2000, which was a continuation of U.S. application Ser. No. 08/769,806, filed Dec. 18, 1996 and issued as U.S. Pat, No. 5,874,500 on Feb. 23, 1999, which was a continuation-in-part of U.S. application Ser. No. 08/573,799, filed Dec. 18, 1995, now abandoned. This application is also a continuation-in-part of U.S. application Ser. No. 09/649,337, filed Aug. 28, 2000, claiming priority to U.S. Provisional Application Ser. No. 60/151,273, filed Aug. 27, 1999. All of the aforementioned applications are incorporated herein by reference in full.

TECHNICAL FIELD

This invention relates generally to compositions and systems for forming crosslinked biomaterials, to the crosslinked biomaterials prepared thereby, and to methods of using such compositions as bioadhesives, for tissue augmentation, in the prevention of surgical adhesions, for coating surfaces of synthetic implants, as drug delivery matrices, for ophthalmic applications, and in other applications, as discussed herein and/or as appreciated by one of ordinary skill in the art.

BACKGROUND OF THE INVENTION

U.S. Pat. No. 5,162,430, issued Nov. 10, 1992, to Rhee et al., and commonly owned by the assignee of the present invention, discloses collagen-synthetic polymer conjugates prepared by covalently binding collagen to synthetic hydrophilic polymers such as various derivatives of polyethylene glycol.

Commonly owned U.S. Pat. No. 5,324,775, issued Jun. 28, 1994, to Rhee et al., discloses various insert, naturally occurring, biocompatible polymers (such as polysaccharides) covalently bound to synthetic, non-immunogenic, hydrophilic polyethylene glycol polymers.

Commonly owned U.S. Pat. No. 5,328,955, issued Jul. 12, 1994, to Rhee et al., discloses various activated forms of polyethylene glycol and various linkages which can be used to produce collagen-synthetic polymer conjugates having a range of physical and chemical properties.

Commonly owned, copending U.S. application Ser. No. 08/403,358, filed Mar. 14, 1995, a European counterpart of which was published as EP 96102366, discloses a crosslinked biomaterial composition that is prepared using a hydrophobic crosslinking agent, or a mixture of hydrophilic and hydrophobic crosslinking agents. Preferred hydrophobic crosslinking agents include any hydrophobic polymer that contains, or can be chemically derivatized to contain, two or more succiniridyl groups.

Commonly owned, copending U.S. application Ser. No. 08/403,360, filed Mar. 14, 1995, issued Mar. 13, 1996 as U.S. Pat. No. 5,580,923 to Yeung et al., discloses a composition useful in the prevention of surgical adhesions comprising a substrate material and an anti-adhesion binding agent; where the substrate material preferably comprises collagen and the binding agent preferably comprises at least one tissue-reactive functional group and at least one substrate-reactive functional group.

Commonly owned, U.S. application Ser. No. 08/476,825, filed Jun. 7, 1995, issued Mar. 25, 1997 as U.S. Pat. No. 5,614,587 to Rhee et al., discloses bioadhesive compositions comprising collagen crosslinked using a multifunctionally activated synthetic hydrophilic polymer, as well as methods of using such compositions to effect adhesion between a first surface and a second surface, wherein at least one of the first and second surfaces is preferably a native tissue surface.

Japanese patent publication No. 07090241 discloses a composition used for temporary adhesion of a lens material to a support, to mount the material on a machining device, comprising a mixture of polyethylene glycol, having an average molecular weight in the range of 1000–5000, and poly-N-vinylpyrrolidone, having an average molecular weight in the range of 30,000–200,000.

West and Hubbell, Biomaterials (1995) 16:1153–1156, disclose the prevention of post-operative adhesions using a photopolymerized polyethylene glycol-co-lactic acid diacrylate hydrogel and a physically crosslinked polyethylene glycol-co-polypropylene glycol hydrogel, Poloxamer 407®.

Each publication cited above and is incorporated herein by reference to describe and disclose the subject matter for which it is cited.

The invention is directed to a versatile biocompatible composition not previously disclosed or envisioned by those in the biomaterial field. The composition is comprised of a crosslinkable matrix that may be readily crosslinked upon admixture with an aqueous medium to provide a crosslinked composition having a variety of uses, e.g., as a bioadhesive, a drug delivery platform, an implant coating, etc. All components of the composition are biocompatible and nonimmunogenic, and do not leave any toxic, inflammatory or immunogenic reaction products at the site of administration. Preferably, the composition is not subject to enzymatic cleavage by matrix metalloproteinases such as collagenase, and is therefore not readily degradable in vivo. Further, the composition may be readily tailored, in terms of the selection and quantity of each component, to enhance certain properties, e.g., compression strength, swellability, tack, hydrophilicity, optical clarity, and the like.

SUMMARY OF THE INVENTION

Accordingly, in one aspect of the invention, a composition is provided that is readily crosslinkable, either in situ or ex situ, to give a biocompatible, nonimmunogenic crosslinked matrix having utility in a host of different contexts, e.g., in bioadhesion, biologically active agent delivery, tissue augmentation, and other applications. The composition is comprised of:

(a) a first crosslinkable component A having m nucleophilic groups, wherein m≧2;

(b) a second crosslinkable component B having n electrophilic groups capable of reaction with the m nucleophilic groups to form covalent bonds, wherein n≧2 and m+n>4; and (c) a third crosslinkable component C having at least one functional group selected from (i) nucleophilic groups capable of reacting with the electrophilic groups of component B and (ii) electrophilic groups capable of reacting with the nucleophilic groups of component A, wherein each of components A, B and C is biocompatible and nonimmunogenic, at least one of components A, B and C is a hydrophilic polymer, and admixture of components A, B and C in an aqueous medium results in crosslinking of the composition to give a biocompatible, noninumunogenic, crosslinked matrix.

Each of the components may be polymeric, in which case at least two components are generally although not necessarily composed of a purely synthetic polymer rather than a naturally occurring or semi-synthetic polymer, wherein "semi-synthetic" refers to a chemically modified naturally occurring polymer. Alternatively, one or two of components A, B and C (but not all three) may be a low molecular weight crosslinking agent, typically an agent comprised of a hydrocarbyl moiety containing 2 to 14 carbon atoms and at least two functional groups, i.e., nucleophilic or electrophilic groups, depending on the component. For convenience, the term "polynucleophilic" will be used herein to refer to a compound having two or more nucleophilic moieties, and the term "polyelectrophilic" will be used to refer to a compound having two or more electrophilic moieties.

In another aspect of the invention, a crosslinkable composition is provided that comprises a plurality of biocompatible, non-immunogenic reactive compounds each composed of a molecular core having at least one functional group attached thereto (i.e., through a direct covalent bond or through a linking group), wherein under reaction-enabling conditions each reactive compound is capable of substantially immediate covalent reaction with at least one other of the plurality of reactive compounds by virtue of the at least one functional group. At least two of the reactive compounds contain two or more functional groups to enable crosslinking, and for preparation of highly crosslinked structures, all of the reactive components contain two or more reactive functional groups. Each molecular core is selected from the group consisting of synthetic hydrophilic polymers, naturally occurring hydrophilic polymers, hydrophobic polymers, and $C_2$–$C_{14}$ hydrocarbyl groups containing zero to 2 heteroatoms selected from N, O, S and combinations thereof, with the proviso that at least one of the molecular cores is a synthetic hydrophilic polymer. Preferably, each molecular core is selected from the group consisting of synthetic hydrophilic polymers and $C_2$–$C_4$ hydrocarbyl groups containing zero to 2 heteroatoms selected from N, O and combinations thereof.

In a related aspect of the invention, a crosslinkable composition is provided that comprises at least three biocompatible, non-immunogenic reactive compounds, wherein a first reactive compound is composed of a synthetic hydrophilic polymer having at least two functional groups attached thereto, a second reactive compound is comprised of a $C_2$–$C_{14}$ hydrocarbyl group containing zero to 2 heteroatoms selected from N, O, S and combinations thereof, with at least two functional groups attached thereto, and a third reactive compound is comprised of a naturally occurring hydrophilic polymer with at least two functional groups attached thereto. The functional groups of at least one of the reactive compounds are hydroxyl or sulfhydryl groups and the functional groups of at least one other of the reactive compounds are electrophilic groups capable of undergoing reaction with the hydroxyl or sulfhydryl groups to form a covalent bond, such that upon admixture of the composition with an aqueous base, a biocompatible, non-immunogenic crosslinked material is formed.

In another aspect of the invention, a biocompatible, nonimmunogenic, crosslinked matrix is provided by allowing the components of the crosslinkable composition to crosslink under appropriate reaction conditions. As will be discussed in detail infia, suitable reaction conditions involve admixture of all components in an aqueous medium. With certain types of nucleophilic groups, e.g., sulfhydryl and hydroxyl groups, it is preferred that the aqueous medium contain a base, which serves to increase the nucleophilic reactivity of such groups. Preferred bases are generally, although not necessarily, non-nucleophilic.

In other aspects of the invention, methods for preparing and using the aforementioned compositions also provided. Methods of using the compositions encompassed by the present invention include drug delivery methods, use in bioadhesion, delivery of cells and genes, tissue augmentation, prevention of adhesions following surgery or injury, and implant coating. Other methods of use are also within the scope of the invention, as will be described below.

BRIEF DESCRIPTION OF THE DRAWINGS

In FIGS. 1–10, the polyelectrophilic components are composed of a pentaerythritol core with each of the four hydroxyl groups substituted with PEG, and with each PEG branch terminated with a reactive electrophilic group. In FIGS. 14–18, the polyelectrophilic components are composed of low molecular weight, hydrophobic molecular cores difunctionalized with succinimidyl esters.

FIG. 16 provides in graph form the tensile test results obtained in Example 10.

FIG. 17 schematically illustrates devices that are useful for measuring tensile strength.

FIG. 18 illustrates the formation of an amide-linked conjugate resulting from reaction of succinimidyl-glutaryl-PEG with amino-PEG.

DETAILED DESCRIPTION OF THE INVENTION

I. Definitions and Nomenclature

Figure 1:
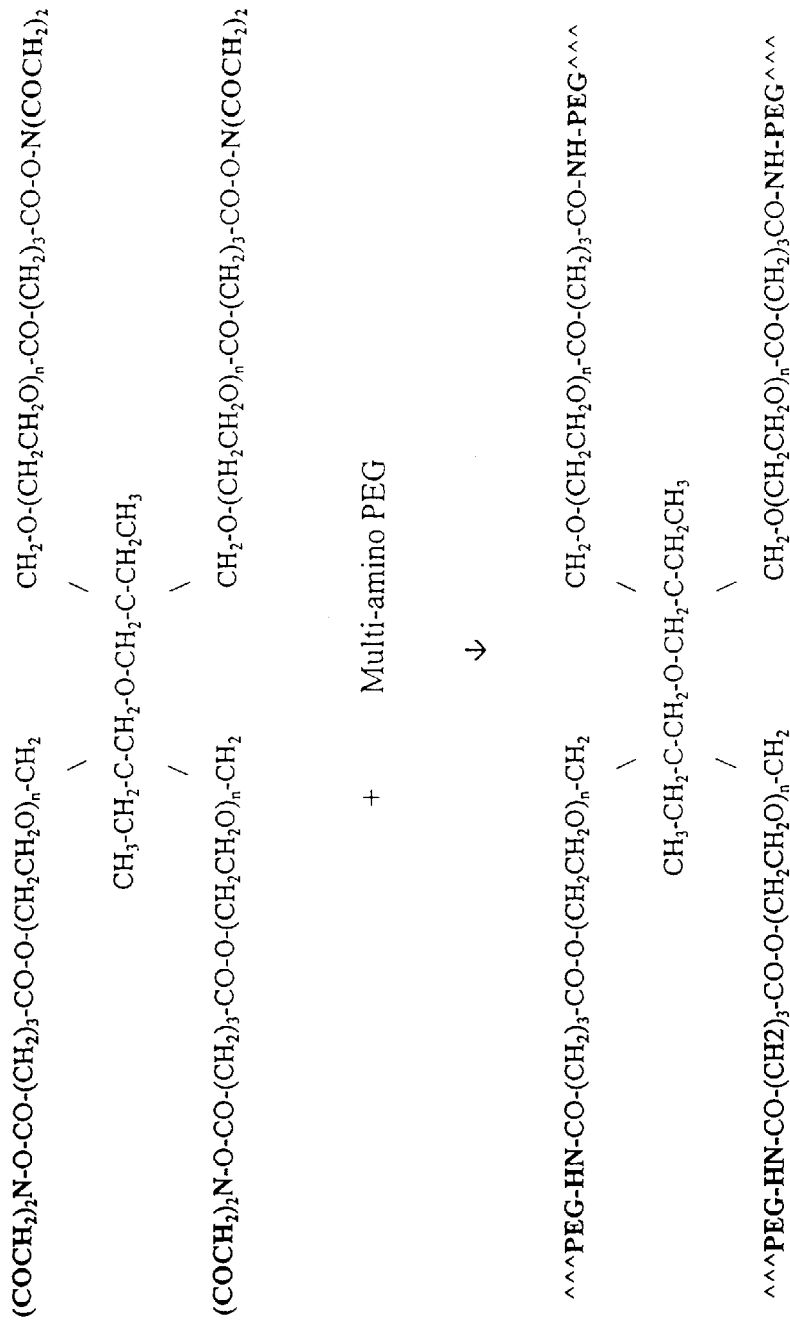
FIGS. 1 to 15 schematically illustrate reaction of various polyelectrophilic components with polyamino-substituted polyethylene glycol (PEG) as a representative polynucleophile.

Before describing the present invention in detail, it is to be understood that unless otherwise indicated this invention is not limited to particular compositional forms, crosslinkable components, crosslinking techniques, or methods of use, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "a crosslinkable component" refers not only to a single crosslinkable component but also to a combination of two or more different crosslinkable component, "a hydrophilic polymer" refers to a combination of hydrophilic polymers as well as to a single hydrophilic polymer, and the like.

Unless defined otherwise, all technical and scientific terms used herein have the meaning commonly understood by one of ordinary skill in the art to which the invention pertains. Although any methods and materials similar or equivalent to those described herein may be useful in the practice or testing of the present invention, preferred methods and materials are described below. All patents, patent applications and other publications mentioned herein are incorporated herein by reference. Specific terminology of particular importance to the description of the present invention is defined below.

The term "crosslinked" herein refers to a composition containing intermolecular crosslinks and optionally intramolecular crosslinks as well, arising from the formation of covalent bonds. Covalent bonding between two crosslinkable components may be direct, in which case an atom in one component is directly bound to an atom in the other component, or it may be indirect, through a linking group. A crosslinked matrix may, in addition to covalent bonds, also include intermolecular and/or intramolecular noncovalent bonds such as hydrogen bonds and electrostatic (ionic) bonds. The term "crosslinkable" refers to a component or compound that is capable of undergoing reaction to form a crosslinked composition.

The terms "nucleophile" and "nucleophilic" refer to a functional group that is electron rich, has an unshared pair of electrons acting as a reactive site, and reacts with a positively charged or electron-deficient site, generally present on another molecule.

The terms "electrophile" and "electrophilic" refer to a functional group that is susceptible to nucleophilic attack, i.e., susceptible to reaction with an incoming nucleophilic group. Electrophilic groups herein are positively charged or electron-deficient, typically electron-deficient.

The term "activated" refers to a modification of an existing functional group to generate or introduce a new reactive functional group from the prior existing functional group, wherein the new reactive functional group is capable of undergoing reaction with another functional group to form a covalent bond. For example, a component containing carboxylic acid (—COOH) groups can be activated by reaction with N-hydroxy-succinimide or N-hydroxysulfosuccinimide using known procedures, to form an activated carboxylate (which is a reactive electrophilic group), i.e., an N-hydroxysuccinimide ester or an N-hydroxysulfosuccinimide ester, respectively. In another example, carboxylic acid groups can be activated by reaction with an acyl halide, e.g., an acyl chloride, again using known procedures, to provide an activated electrophilic group in the form of an anhydride.

The terms "hydrophilic" and "hydrophobic" are generally defined in terms of a partition coefficient P, which is the[]ratio of the equilibrium concentration of a compound in an organic phase to that in an aqueous phase. A hydrophilic compound has a log P value less than 1.0, typically less than about −0.5, where P is the partition coefficient of the compound between octanol and water, while hydrophobic compounds will generally have a log P greater than about 3.0, typically greater than about 5.0. Preferred crosslinkable components herein are hydrophilic, although as long as the crosslinkable composition as a whole contains at least one hydrophilic component, crosslinkable hydrophobic components may also be present.

The term "polymer" is not only used in the conventional sense to refer to molecules composed of repeating monomer units, including homopolymers, block copolymers, random copolymers, and graft copolymers, but is also used, as indicated in parent application Ser. No. 09/733, 739, to refer to polyfunctional small molecules that do not contain repeating monomer units but are "polymeric" in the sense of being "polyfunctional," i.e., containing two or more functional groups. Accordingly, it will be appreciated that when the term "polymer" is used, difunctional and polyfunctional small molecules are included. Such moieties include, by way of example: the difunctional electrophiles disuccinimidyl suberate (DSS), bis(sulfosuccinimidyl) suberate ($BS^3$), dithiobis(succinimidylpropionate) (DSP), bis(2-succinimidooxy-carbonyloxy) ethyl sulfone (BSOCOES), 3,3'-dithiobis(sulfosuccinimidylpropionate (DTSSP); and the di-and polyfunctional nucleophiles ethylenediamine ($H_2N$—$CH_2$—$CH_2$—$NH_2$), tetramethylene diamine ($H_2N$—$[CH_2]_4$—$NH_2$), pentamethylene diamine (cadaverine) ($H_2N$—$[CH_2]_5$—$NH_2$), hexamethylene diamine ($H_2N$—$[CH_2]_6$—$NH_2$), bos(2-aminoethyl)amine (HN—$[CH_2$—$CH_2$—$NH_2]_2$), and tris (2-aminoethyl)amine (N—$[CH_2$—$CH_2$—$NH_2]_3$). All suitable polymers herein are nontoxic, non-inflammatory and nonimmunogenic, and will preferably be essentially nondegradable in vivo over a period of at least several months.

The term "synthetic" to refer to various polymers herein is intended to mean "chemically synthesized." Therefore, a synthetic polymer in the present compositions may have a molecular structure that is identical to a naturally occurring polymer, but the polymer per se, as incorporated in the compositions of the invention, has been chemically synthesized in the laboratory or industrially. "Synthetic" polymers also include semi-synthetic polymers, i.e., naturally occurring polymers, obtained from a natural source, that have been chemically modified in some way. Generally, however, the synthetic polymers herein are purely synthetic, i.e., they are neither semi-synthetic nor have a structure that is identical to that of a naturally occurring polymer.

The term "synthetic hydrophilic polymer" as used herein refers to a synthetic polymer composed of molecular segments that render the polymer as a whole "hydrophilic," as defined above. Preferred polymers are highly pure or are purified to a highly pure state such that the polymer is or is treated to become pharmaceutically pure. Most hydrophilic polymers can be rendered water soluble by incorporating a sufficient number of oxygen (or less frequently nitrogen) atoms available for forming hydrogen bonds in aqueous solutions. Hydrophilic polymers useful herein include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly (hydroxyethylmethacrylate), poly(hydroxyethylacrylate), poly(methylalkylsulfoxide methacrylate), poly (methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly (dimethylacrylamide), and poly(N-isopropyl-acrylamide); poly(olefinic alcohol)s such as poly(vinyl alcohol); poly(N- vinyl lactams) such as poly(vinyl pyrrolidone), poly(N-vinyl caprolactam), and copolymers thereof; polyoxazolines, including poly(methyloxazoline) and poly(ethyloxazoline); and polyvinylamines.

Hydrophobic polymers, including low molecular weight polyfunctional species, can also be used in the crosslinkable compositions of the invention. Hydrophobic polymers preferably contain, or can be derivatized to contain, two or more electrophilic groups, such as succinimidyl groups, most preferably, two, three, or four electrophilic groups. Generally, "hydrophobic polymers" herein contain a relatively small proportion of oxygen and/or nitrogen atoms. Preferred hydrophobic polymers for use in the invention generally have a carbon chain that is no longer than about 14 carbons. Polymers having carbon chains substantially longer than 14 carbons generally have very poor solubility in aqueous solutions and, as such, have very long reaction times when mixed with aqueous solutions of synthetic polymers containing multiple nucleophilic groups.

The term "collagen" as used herein refers to all forms of collagen, including those, which have been processed or otherwise modified. Preferred collagens are treated to remove the immunogenic telopeptide regions ("atelopeptide collagen"), are soluble, and may be in fibrillar or non-fibrillar form. Type I collagen is best suited to most applications involving bone or cartilage repair. However, other forms of collagen are also useful in the practice of the invention, and are not excluded from consideration here. Collagen crosslinked using heat, radiation, or chemical agents such as glutaraldehyde may also be used to form particularly rigid crosslinked compositions. Collagen crosslinked using glutaraldehyde or other (nonpolymer) linking agents is typically referred to herein as "GAX" while collagen crosslinked using heat and/or radiation is termed "HRX." Collagen used in connection with the preferred embodiments of the invention is in a pharmaceutically pure form such that it can be incorporated into a human body for the intended purpose.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weights indicates that the average molecular weight may be any value between the limits specified, and may include molecules outside those limits. Thus, a molecular weight range of about 800 to about 20,000 indicates an average molecular weight of at least about 800, ranging up to about 20 kDa.

The term "cytokine" is used to describe biologically active molecules including growth factors and active peptides, which aid in healing or regrowth of normal tissue. The function of cytokines is two-fold: 1) they can incite local cells to produce new collagen or tissue, or 2) they can attract cells to the site in need of correction. As such, cytokines serve to encourage "biological anchoring" of the collagen implant within the host tissue. As previously described, the cytokines can either be admixed with the collagen-polymer conjugate or chemically coupled to the conjugate. For example, one 30 may incorporate cytokines such as epidermal growth factor (EGF), transforming growth factor (TGF)-α, TGF-β (including any combination of TGF-βs), TGF-β1, TGF-β2, platelet derived growth factor (PDGF-AA, PDGF-AB, PDGF-BB), acidic fibroblast growth factor (FGF), basic FGF, connective tissue activating peptides (CTAP), β-thromboglobulin, insulin-like growth factors, tumor necrosis factors (TNF), interleukins, colony stimulating factors (CSFs), erythropoietin (EPO), nerve growth factor (NGF), interferons (IFN) bone morphogenic protein (BMP), osteogenic factors, and the like. Incorporation of cytokines, and appropriate combinations of cytokines can facilitate the regrowth and remodeling of the implant into normal bone tissue, or may be used in the treatment of wounds.

The term "effective amount" refers to the amount of composition required in order to obtain the effect desired. Thus, a "tissue growth-promoting amount" of a composition refers to the amount needed in order to stimulate tissue growth to a detectable degree. Tissue, in this context, includes connective tissue, bone, cartilage, epidermis and dermis, blood, and other tissues. The actual amount that is determined to be an effective amount will vary depending on factors such as the size, condition, sex and age of the patient and can be more readily determined by the caregiver.

The term "solid implant" refers to any solid object which is designed for insertion and use within the body, and includes bone and cartilage implants (e.g., artificial joints, retaining pins, cranial plates, and the like, of metal, plastic and/or other materials), breast implants (e.g., silicone gel envelopes, foam forms, and the like), catheters and cannulas intended for long-term use (beyond about three days) in place, artificial organs and vessels (e.g., artificial hearts, pancreases, kidneys, blood vessels, and the like), drug delivery devices (including monolithic implants, pumps and controlled release devices such as Alzet® minipumps, steroid pellets for anabolic growth or contraception, and the like), sutures for dermal or internal use, periodontal membranes, ophthalmic shields, corneal lenticules, and the like.

The term "suitable fibrous material" as used herein, refers to a fibrous material which is substantially insoluble in water, non-immunogenic, biocompatible, and immiscible with the crosslinkable compositions of the invention. The fibrous material may comprise any of a variety of materials having these characteristics and may be combined with crosslinkable compositions herein in order to form and/or provide structural integrity to various implants or devices used in connection with medical and pharmaceutical uses. For example, the crosslinkable compositions of the invention can be coated on the "suitable fibrous material," which can then be wrapped around a bone to provide structural integrity to the bone. Thus, the "suitable fibrous material" is useful in forming the "solid implants" of the invention.

The term "in situ" as used herein means at the site of administration. Thus, the injectable reaction mixture compositions are injected or otherwise applied to a specific site within a patient's body, e.g., a site in need of augmentation, and allowed to crosslink at the site of injection. Suitable sites will generally be intradermal or subcutaneous regions for augmenting dermal support, at a bone fracture site for bone repair, within sphincter tissue for sphincter augmentation (e.g., for restoration of continence), within a wound or suture, to promote tissue regrowth, and within or adjacent to vessel anastomoses, to promote vessel regrowth.

The term "aqueous medium" includes solutions, suspensions, dispersions, colloids, and the like containing water.

The term "substantially immediately" means within less than five minutes, preferably within less than two minutes, and the term "immediately" means within less than one minute, preferably within less than 30 seconds.

The terms "active agent," and "biologically active agent" are used interchangeably herein to refer to a chemical material or compound suitable for administration to a patient and that induces a desired effect. The terms include agents that are therapeutically effective as well as prophylactically effective. Also included are derivatives and analogs of those compounds or classes of compounds specifically mentioned that also induce the desired effect.

The term "hydrogel" is used in the conventional sense to refer to water-swellable polymeric matrices that can absorb a substantial amount of water to form elastic gels, wherein "matrices" are three-dimensional networks of macromolecules held together by covalent or noncovalent crosslinks. Upon placement in an aqueous environment, dry hydrogels swell to the extent allowed by the degree of cross-linking.

With regard to nomenclature pertinent to molecular structures, the following definitions apply:

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups. "Alkylene," "lower alkylene" and "substituted alkylene" refer to divalent alkyl, lower alkyl, and substituted alkyl groups, respectively.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom. The terms "arylene" and "substituted arylene" refer to divalent aryl and substituted aryl groups as just defined.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. If not otherwise indicated, "hydrocarbyl" indicates unsubstituted hydrocarbyl, substituted hydrocarbyl, heteroatom-containing hydrocarbyl, and substituted heteroatom-containing hydrocarbyl. Unless otherwise indicated, the terms "hydrocarbyl" and "hydrocarbylene" include substituted hydrocarbyl and substituted hydrocarbylene, heteroatom-containing hydrocarbyl and heteroatom-containing hydrocarbylene, and substituted heteroatom-containing hydrocarbyl and substituted heteroatom-containing hydrocarbylene, respectively.

By "substituted" as in "substituted hydrocarbyl," "substituted alkyl," and the like, as alluded to in some of the aforementioned definitions, is meant that in the hydrocarbyl, alkyl, or other moiety, at least one hydrogen atom bound to a carbon atom is replaced with one or more substituents that are functional groups such as alkoxy, hydroxy, halo, nitro, and the like. Unless otherwise indicated, it is to be understood that specified molecular segments can be substituted with one or more substituents that do not compromise a compound's utility. For example, "succinimidyl" is intended to include unsubstituted succinimidyl as well as sulfosuccinimidyl and other succinimidyl groups substituted on a ring carbon atom, e.g., with alkoxy substituents, polyether substituents, or the like.

II. The Crosslinkable Composition

In accordance with the present invention, a crosslinkable polymer composition is provided that contains a minimum of three components, each of which participates in a rreaction that results in a crosslinked matrix. The components of the crosslinkable composition are selected so that crosslinking gives rise to a biocompatible, nonimmunogenic matrix useful in a variety of contexts, including adhesion, biologically active agent delivery, tissue augmentation, and other applications. The crosslinkable composition of the invention is comprised of at least three crosslinkable components: a first component, component A, which has m nucleophilic groups, wherein $m \geq 2$; a second component, component B, which has n electrophilic groups capable of reaction with the m nucleophilic groups, wherein $n \geq 2$ and $m+n>4$; and a third component, component C, which has at least one functional group that is either electrophilic and capable of reaction with the nucleophilic groups of component A, or nucleophilic and capable of reaction with the electrophilic groups of component B. Thus, the total number of functional groups present on components A, B and C in combination is >5; that is, the total functional groups given by m+n+p must be >5, where p is the number of functional groups on component C and, as indicated, is $\geq 1$. Each of the components is biocompatible and nonimmunogenic, and at least one component is comprised of a hydrophilic polymer. For those compositions in which a higher degree of crosslinking is required, e.g., when a less swellable biomaterial is desirable or increased compressive strength is necessary, p should be $\geq 2$. Also, as will be appreciated, the crosslinkable composition may contain additional components D. E, F, etc., having one or more reactive nucleophilic or electrophilic groups and thereby participate in formation of the crosslinked biomaterial via covalent bonding to other components.

The m nucleophilic groups on component A may all be the same, or, alternatively, A may contain two or more different nucleophilic groups. Similarly, the n electrophilic groups on component B may all be the same, or two or more different electrophilic groups may be present. The functional group(s) on component C, if nucleophilic, may or may not be the same as the nucleophilic groups on component A, and, conversely, if electrophilic, the functional group(s) on component C may or may not be the same as the electrophilic groups on component B.

Accordingly, the components may be represented by the structural formulae $$R^1(-[Q^1]_q-X)_m \quad \text{(component A)}, \qquad (I)$$

$$R^2(-[Q^2]_r-Y)_n \quad \text{(component B), and} \qquad (II)$$

$$R^3(-[Q^3]_s-Fn)_p \quad \text{(component C)}, \qquad (III)$$

wherein:

$R^1$, $R^2$ and $R^3$ are independently selected from the group consisting of $C_2$ to $C_{14}$ hydrocarbyl, heteroatom-containing $C_2$ to $C_{14}$ hydrocarbyl, hydrophilic polymers, and hydrophobic polymers, providing that at least one of $R^1$, $R^2$ and $R^3$ is a hydrophilic polymer, preferably a synthetic hydrophilic polymer;

X represents one of the m nucleophilic groups of component A, and the various X moieties on A may be the same or different;

Y represents one of the n electrophilic groups of component B, and the various Y moieties on A may be the same or different;

Fn represents a functional group on component C;

$Q^1$, $Q^2$ and $Q^3$ are linking groups;

$m \geq 2$, $n \geq 2$, $m+n$ is $>4$, $p \geq 1$, and q, r and s are independently zero or 1.

A. Reactive Groups

X may be virtually any nucleophilic group, so long as reaction can occur with the electrophilic group Y and also with Fn when Fn is electrophilic. Analogously, Y may be virtually any electrophilic group, so long as reaction can take place with X and also with Fn when Fn is nucleophilic. The only limitation is a practical one, in that reaction between X and Y, X and $Fn_{EL}$ (where $Fn_{EL}$ indicates an electrophilic Fn group), and Y and $Fn_{NU}$, should be fairly rapid and take place automatically upon admixture with an aqueous medium, without need for heat or potentially toxic or non-biodegradable reaction catalysts or other chemical reagents. It is also preferred although not essential that reaction occur without need for ultraviolet or other radiation. Ideally, the reactions between X and Y, and between either X and $Fn_{EL}$ or Y and $Fn_{NU}$, should be complete in under 60 minutes, preferably under 30 minutes. Most preferably, the reaction occurs in about 5 to 15 minutes or less. Examples of nucleophilic groups suitable as X or $Fn_{NU}$ include, but are not limited to, $-NH_2$, $-NHR^4$, $-N(R^4)_2$, $-SH$, $-OH$, $-COOH$, $-C_6H_4-OH$, $-PH_2$, $-PHR^5$, $-P(R^5)_2$, $-NH-NH_2$, $-CO-NH-NH_2$, $-C_5H_4N$, etc. wherein $R^4$ and $R^5$ are hydrocarbyl, typically alkyl or monocyclic aryl, preferably alkyl, and most preferably lower alkyl. Organometallic moieties are also useful nucleophilic groups for the purposes of the invention, particularly those that act as carbanion donors. Organometallic nucleophiles are not, however, preferred. Examples of organometallic moieties include: Grignard functionalities $-R^6MgHal$ wherein $R^6$ is a carbon atom (substituted or unsubstituted), and Hal is halo, typically bromo, iodo or chloro, preferably bromo; and lithium-containing functionalities, typically alkyllithium groups; sodium-containing functionalities.

It will be appreciated by those of ordinary skill in the art that certain nucleophilic groups must be activated with a base so as to be capable of reaction with an electrophile. For example, when there are nucleophilic sulfhydryl and hydroxyl groups in the crosslinkable composition, the composition must be admixed with an aqueous base in order to remove a proton and provide an $-S^-$ or $-O^-$ species to enable reaction with an electrophile. Unless it is desirable for the base to participate in the crosslinking reaction, a nonnucleophilic base is preferred. In some embodiments, the base may be present as a component of a buffer solution. Suitable bases and corresponding crosslinking reactions are described infra in Section III.

The selection of electrophilic groups provided within the crosslinkable composition, i.e., on component B and on component C when Fn is electrophilic, must be made so that reaction is possible with the specific nucleophilic groups. Thus, when the X moieties are amino groups, the Y and any $Fn_{EL}$ groups are selected so as to react with amino groups. Analogously, when the X moieties are sulhydryl moieties, the corresponding electrophilic groups are sulfhydryl-reactive groups, and the like.

By way of example, when X is amino (generally although not necessarily primary amino), the electrophilic groups present on Y and $Fn_{EL}$ are amino reactive groups such as, but not limited to: (1) carboxylic acid esters, including cyclic esters and "activated" esters; (2) acid chloride groups ($-CO-Cl$); (3) anhydrides ($-(CO)-O-(CO)-R$); (4) ketones and aldehydes, including $\alpha,\beta$-unsaturated aldehydes and ketones such as $-CH=CH-CH=O$ and $-CH=CH-C(CH_3)=O$; (5) halides; (6) isocyanate ($-N=C=O$); (7) isothiocyanate ($-N=C=S$); (8) epoxides; (9) activated hydroxyl groups (e.g., activated with conventional activating agents such as carbonyldiimidazole or sulfonyl chloride); and (10) olefins, including conjugated olefins, such as ethenesulfonyl ($-SO_2CH=CH_2$) and analogous functional groups, including acrylate ($-CO_2-C=CH_2$), methacrylate ($-CO_2-C(CH_3)=CH_2$)), ethyl acrylate ($-CO_2-C(CH_2CH_3)=CH_2$), and ethyleneimino ($-CH=CH-C=NH$). Since a carboxylic acid group per se is not susceptible to reaction with a nucleophilic amine, components containing carboxylic acid groups must be activated so as to be amine-reactive. Activation may be accomplished in a variety of ways, but often involves reaction with a suitable hydroxyl-containing compound in the presence of a dehydrating agent such as dicyclohexylcarbodiimide (DCC) or dicyclohexylurea (DHU). For example, a carboxylic acid can be reacted with an alkoxy-substituted N-hydroxy-succinimide or N-hydroxysulfosuccinimide in the presence of DCC to form reactive electrophilic groups, the N-hydroxysuccinimide ester and the N-hydroxysulfosuccinimide ester, respectively. Carboxylic acids may also be activated by reaction with an acyl halide such as an acyl chloride (e.g., acetyl chloride), to provide a reactive anhydride group. In a further example, a carboxylic acid may be converted to an acid chloride group using, e.g., thionyl chloride or an acyl chloride capable of an exchange reaction. Specific reagents and procedures used to carry out such activation reactions will be known to those of ordinary skill in the art and are described in the pertinent texts and literature.

Analogously, when X is sulfhydryl, the electrophilic groups present on Y and $Fn_{EL}$ are groups that react with a sulfhydryl moiety. Such reactive groups include those that form thioester linkages upon reaction with a sulfhydryl group, such as those described in applicants' PCT Publication No. WO 00/62827 to Wallace et al. As explained in detail therein, such "sulfhydryl reactive" groups include, but are not limited to: mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarinide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates. With these sulfhydryl reactive groups, auxiliary reagents can also be used to facilitate bond formation, e.g., 1-ethyl-3-[3-dimethylaminopropyl] carbodiimide can be used to facilitate coupling of sulfhydryl groups to carboxyl-containing groups.

In addition to the sulfhydryl reactive groups that form thioester linkages, various other sulfydryl reactive functionalities can be utilized that form other types of linkages. For example, compounds that contain methyl imidate derivatives form imido-thioester linkages with sulfhydryl groups. Alternatively, sulthydryl reactive groups can be employed that form disulfide bonds with sulthydryl groups, such groups generally have the structure —S—S—Ar where Ar is a substituted or unsubstituted nitrogen-containing heteroaromatic moiety or a non-heterocyclic aromatic group substituted with an electron-withdrawing moiety, such that Ar may be, for example, 4-pyridinyl, o-nitrophenyl, m-nitrophenyl, p-nitrophenyl, 2,4-dinitrophenyl, 2-nitro-4-benzoic acid, 2-nitro-4-pyridinyl, etc. In such instances, auxiliary reagents, i.e., mild oxidizing agents such as hydrogen peroxide, can be used to facilitate disulfide bond formation.

Yet another class of sulfhydryl reactive groups forms thioether bonds with sulfhydryl groups. Such groups include, inter alia, maleimido, substituted maleimido, haloalkyl, epoxy, imino, and aziridino, as well as olefins (including conjugated olefins) such as ethenesulfonyl, etheneimino, acrylate, methacrylate, and ($\alpha,\beta$-unsaturated aldehydes and ketones.

When X is —OH, the electrophilic functional groups on the remaining component(s) must react with hydroxyl groups. The hydroxyl group may be activated as described above with respect to carboxylic acid groups, or it may react directly in the presence of base with a sufficiently reactive electrophile such as an epoxide group, an aziridine group, an acyl halide, an anhydride, When X is an organometallic nucleophile such as a Grignard functionality or an alkyllithium group, suitable electrophilic functional groups for reaction therewith are those containing carbonyl groups, including, by way of example, ketones and aldehydes.

It will also be appreciated that certain functional groups can react as nucleophiles or as electrophiles, depending on the selected reaction partner and/or the reaction conditions. For example, a carboxylic acid group can act as a nucleophile in the presence of a fairly strong base, but generally acts as an electrophile allowing nucleophilic attack at the carbonyl carbon and concomitant replacement of the hydroxyl group with the incoming nucleophile.

The covalent linkages in the crosslinked structure that result upon covalent binding of specific nucleophilic components to specific electrophilic components in the crosslinkable composition include, solely by way of example, the following (the optional linking groups $Q^1$, $Q^2$ and $Q^3$ are omitted for clarity):

TABLE 1

| REPRESENTATIVE NUCLEOPHILIC COMPONENT (A, $FN_{NU}$) | REPRESENTATIVE ELECTROPHILIC COMPONENT (B, $FN_{EL}$) | RESULTING LINKAGE |
|---|---|---|
| $R^1$—$NH_2$ | $R^2$—O—(CO)—O—N(COCH$_2$) (succinimidyl carbonate terminus) | $R^1$—NH—(CO)—O—$R^2$ |
| $R^1$—SH | $R^2$—O—(CO)—O—N(COCH$_2$) | $R^1$—S—(CO)—O—$R^2$ |
| $R^1$—OH | $R^2$—O—(CO)—O—N(COCH$_2$) | $R^1$—S—(CO)—$R^2$ |
| $R^1$—$NH_2$ | $R^2$—O(CO)—CH=CH$_2$ (acrylate terminus) | $R^1$—NH—CH$_2$CH$_2$—(CO)—O—$R^2$ |
| $R^1$—SH | $R^2$—O—(CO)—CH=CH$_2$ | $R^1$—S—CH$_2$CH$_2$—(CO)—O—$R^2$ |
| $R^1$—OH | $R^2$—O—(CO)—CH=CH$_2$ | $R^1$—O—CH$_2$CH$_2$—(CO)—O—$R^2$ |
| $R^1$—$NH_2$ | $R^2$—O(CO)—(CH$_2$)$_3$—CO$_2$N(COCH$_2$) (succinimidyl glutarate terminus) | $R^1$—NH—(CO)—(CH$_2$)$_3$—(CO)—O$R^2$ |
| $R^1$—SH | $R^2$—O(CO)—(CH$_2$)$_3$—CO$_2$—N(COCH$_2$) | $R^1$—S—(CO)—(CH$_2$)$_3$—(CO)—O$R^2$ |
| $R^1$—OH | $R^2$—O(CO)—(CH$_2$)$_3$—CO$_2$—N(COCH$_2$) | $R^1$—O—(CO)—(CH$_2$)$_3$—(CO)—O$R^2$ |
| $R^1$—$NH_2$ | $R^2$—O—CH$_2$—CO$_2$—N(COCH$_2$) (succinimidyl acetate terminus) | $R^1$—NH—(CO)—CH$_2$—O$R^2$ |
| $R^1$—SH | $R^2$—O—CH$_2$—CO$_2$—N(COCH$_2$) | $R^1$—S—(CO)—CH$_2$—O$R^2$ |
| $R^1$—OH | $R^2$—O—CH$_2$—CO$_2$—N(COCH$_2$) | $R^1$—O—(CO)—CH$_2$—O$R^2$ |
| $R^1$—$NH_2$ | $R^2$—O—NH(CO)—(CH$_2$)$_2$—CO$_2$—N(COCH$_2$) (succinimidyl succinamide terminus) | $R^1$—NH—(CO)—(CH$_2$)$_2$—(CO)—NH—O$R^2$ |
| $R^1$—SH | $R^2$—O—NH(CO)—(CH$_2$)$_2$—CO$_2$—N(COCH$_2$) | $R^1$—S—(CO)—(CH$_2$)$_2$—(CO)—NH—O$R^2$ |
| $R^1$—OH | $R^2$—O—NH(CO)—(CH$_2$)$_2$—CO$_2$—N(COCH$_2$) | $R^1$—O—(CO)—(CH$_2$)$_2$—(CO)—NH—O$R^2$ |
| $R^1$—$NH_2$ | $R^2$—O—(CH$_2$)$_2$—CHO (propionaldehyde terminus) | $R^1$—NH—(CO)—(CH$_2$)$_2$—O$R^2$ |

TABLE 1-continued

| REPRESENTATIVE NUCLEOPHILIC COMPONENT (A, $FN_{NU}$) | REPRESENTATIVE ELECTROPHILIC COMPONENT (B, $FN_{EL}$) | RESULTING LINKAGE |
|---|---|---|
| $R^1$—$NH_2$ | 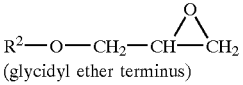<br>(glycidyl ether terminus) | $R^1$—NH—$CH_2$—CH(OH)—$CH_2$—$OR^2$ and<br>$R^1$—N[$CH_2$—CH(OH)—$CH_2$—$OR^2$]$_2$ |
| $R^1$—$NH_2$ | $R^2$—O—($CH_2$)$_2$—N=C=O<br>(isocyanate terminus) | $R^1$—NH—(CO)—NH—$CH_2$—$OR^2$ |
| $R^1$—$NH_2$ | $R^2$—$SO_2$—CH=$CH_2$<br>(vinyl sulfone terminus) | $R^1$—NH—$CH_2CH_2$—$SO_2$—$R^2$ |
| $R^1$—SH | $R^2$—$SO_2$—CH=$CH_2$ | $R^1$—S—$CH_2CH_2$—$SO_2$—$R^2$ |

B. LINKING GROUPS

The functional groups X, Y and Fn may be directly attached to the compound core ($R^1$, $R^2$ or $R^3$, respectively), or they may be indirectly attached through a linking group, with longer linking groups also termed "chain extenders." In structural formulae (I), (II) and (III), $R^1$(—[$Q^1$]$_q$—X)$_m$ (component A)  (I)

$R^2$(—[$Q^2$]$_r$—Y)$_n$ (component B)  (II)

$R^3$(—[$Q^3$]$_s$—Fn)$_p$ (component C)  (III)

the optional linking groups are represented by $Q^1$, $Q^2$ and $Q^3$, wherein the linking groups are present when q, r and s are equal to 1 (with R, X, Y, Fn, m n and p as defined previously).

Suitable linking groups are well known in the art. See, for example, International Patent Publication No. WO 97/22371. Linking groups are useful to avoid steric hindrance problems that are sometimes associated with the formation of direct linkages between molecules. Linking groups may additionally be used to link several multifunctionally activated compounds together to make larger molecules. In a preferred embodiment, a linking group can be used to alter the degradative properties of the compositions after administration and resultant gel formation. For example, linking groups can be incorporated into components. A, B or C to promote hydrolysis, to discourage hydrolysis, or to provide a site for enzymatic degradation.

Examples of linking groups that provide hydrolyzable sites, include, inter alia: ester linkages; anhydride linkages, such as obtained by incorporation of glutarate and succinate; ortho ester linkages; ortho carbonate linkages such as trimethylene carbonate; amide linkages; phosphoester linkages; α-hydroxy acid linkages, such as may be obtained by incorporation of lactic acid and glycolic acid; lactone-based linkages, such as may be obtained by incorporation of caprolactone, valerolactone, γ-butyrolactone and p-dioxanone; and amide linkages such as in a dimeric, oligomeric, or poly(amino acid) segment. Examples of non-degradable linking groups include succinimide, propionic acid and carboxymethylate linkages. See, for example, PCT WO 99/07417. Examples of enzymatically degradable linkages include Leu-Gly-Pro-Ala, which is degraded by collagenase; and Gly-Pro-Lys, which is degraded by plasmin.

Linking groups can also enhance or suppress the reactivity of the various nucleophilic and electrophilic groups. For example, electron-withdrawing groups within one or two carbons of a sulfhydryl group would be expected to diminish its effectiveness in coupling, due to a lowering of nucleophilicity. Carbon-carbon double bonds and carbonyl groups will also have such an effect. Conversely, electron-withdrawing groups adjacent to a carbonyl group (e.g., the reactive carbonyl of glutaryl-N-hydroxysuccinimidyl) would increase the reactivity of the carbonyl carbon with respect to an incoming nucleophile. By contrast, sterically bulky groups in the vicinity of a functional group can be used to diminish reactivity and thus coupling rate as a result of steric hindrance.

By way of example, particular linking groups and corresponding component structure are indicated in Table 2:

TABLE 2

| LINKING GROUP | COMPONENT STRUCTURE |
|---|---|
| —O—($CH_2$)$_n$— | Component A: $R^1$—O—($CH_2$)$_n$—X<br>Component B: $R^2$—O—($CH_2$)$_n$—Y<br>Component C: $R^3$—O—($CH_2$)$_n$—Z |
| —S—($CH_2$)$_n$— | Component A: $R^1$—S—($CH_2$)$_n$—X<br>Component B: $R^2$—S—($CH_2$)$_n$—Y<br>Component C: $R^3$—S—($CH_2$)$_n$—Z |
| —NH—($CH_2$)$_n$— | Component A: $R^1$—NH—($CH_2$)$_n$—X<br>Component B: $R^2$—NH—($CH_2$)$_n$—Y<br>Component C: $R^3$—NH—($CH_2$)$_n$—Z |
| —O—(CO)—NH—($CH_2$)$_n$— | Component A:<br>$R^1$—O—(CO)—NH—($CH_2$)$_n$—X<br>Component B:<br>$R^2$—O—(CO)—NH—($CH_2$)$_n$—Y<br>Component C:<br>$R^3$—O—(CO)—NH—($CH_2$)$_n$—Z |
| —NH—(CO)—O—($CH_2$)$_n$— | Component A:<br>$R^1$—NH—(CO)—O—($CH_2$)$_n$—X<br>Component B:<br>$R^2$—NH—(CO)—O—($CH_2$)$_n$—Y<br>Component C:<br>$R^3$—NH—(CO)—O—($CH_2$)$_n$—Z |
| —O—(CO)—($CH_2$)$_n$— | Component A:<br>$R^1$—O—(CO)—($CH_2$)$_n$—X<br>Component B:<br>$R^2$—O—(CO)—($CH_2$)$_n$—Y<br>Component C:<br>$R^3$—O—(CO)—($CH_2$)$_n$—Z |
| —(CO)—O—($CH_2$)$_n$— | Component A:<br>$R^1$—(CO)—O—($CH_2$)$_n$—X<br>Component B:<br>$R^2$—(CO)—O—($CH_2$)$_n$—Y<br>Component C:<br>$R^3$—(CO)—O—($CH_2$)$_n$—Z |
| —O—(CO)—O—($CH_2$)$_n$— | Component A:<br>$R^1$—O—(CO)—O—($CH_2$)$_n$—X<br>Component B:<br>$R^2$—O—(CO)—O—($CH_2$)$_n$—Y<br>Component C:<br>$R^3$—O—(CO)—O—($CH_2$)$_n$—Z |
| —O—(CO)—$CHR^7$— | Component A: $R^1$—O—(CO)—$CHR^7$—X<br>Component B: $R^2$—O—(CO)—$CHR^7$—Y<br>Component C: $R^3$—O—(CO)—$CHR^7$—Z |

TABLE 2-continued

| LINKING GROUP | COMPONENT STRUCTURE |
| --- | --- |
| —O—R$^8$—(CO)—NH— | Component A:<br>R$^1$—O—R$^8$—(CO)—NH—X<br>Component B:<br>R$^2$—O—R$^8$—(CO)—NH—Y<br>Component C:<br>R$^3$—O—R$^8$—(CO)—NH—Z |

In the table, n is generally in the range of 1 to about 10, R$^7$ is generally hydrocarbyl, typically alkyl or aryl, preferably alkyl, and most preferably loweralkyl, and R$^8$ is hydrocarbylene, heteroatom-containing hydrocarbylene, substituted hydrocarbylene, or substituted heteroatom-containing hydrocarbylene) typically alkylene or arylene (again, optionally substituted and/or containing a heteroatom), preferably lower alkylene (e.g., methylene, ethylene, n-propylene, n-butylene, etc.), phenylene, or amidoalkylene (e.g., —(CO)—NH—CH$_2$).

Other general principles that should be considered with respect to linking groups are as follows: If higher molecular weight components are to be used, they preferably have biodegradable linkages as described above, so that fragments larger than 20,000 mol. wt. are not generated during resorption in the body. In addition, to promote water miscibility and/or solubility, it may be desired to add sufficient electric charge or hydrophilicity. Hydrophilic groups can be easily introduced using known chemical synthesis, so long as they do not give rise to unwanted swelling or an undesirable decrease in compressive strength. In particular, polyalkoxy segments may weaken gel strength.

C. The Component Core

The "core" of each crosslinkable component is comprised of the molecular structure to which the nucleophilic or electrophilic groups are bound. Using the formulae (I) R$^1$—[Q$^1$]$_q$—X)$_m$, for component A, (II) R$^2$(—[Q$^2$]$_r$—Y)$_n$ for component B, and (III) R$^3$(—[Q$^3$]$_s$—Fn)$_p$ for component C, the "core" groups are R$^1$, R$^2$ and R$^3$. Each molecular core of the reactive components of the crosslinkable composition is generally selected from synthetic and naturally occurring hydrophilic polymers, hydrophobic polymers, and C$_2$–C$_{14}$ hydrocarbyl groups zero to 2 heteroatoms selected from N, O and S, with the proviso that at least one of the crosslinkable components A, B and C comprises a molecular core of a synthetic hydrophilic polymer. In a preferred embodiment, at least two of A, B and C comprises a molecular core of a synthetic hydrophilic polymer.

1. HYDROPHILIC POLYMERS AND "ACTIVATION" THEREOF

A "hydrophilic polymer" as used herein refers to a synthetic polymer having an average molecular weight and composition effective to render the polymer "hydrophilic" as defined in Part (I) of this section. Synthetic hydrophilic polymers useful herein include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose, acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly(N-vinyl caprolactam), and copolymers thereof, polyoxazolines, including poly(methyloxazoline) and poly(ethyloxazoline); and polyvinylamines. It must be emphasized that the aforementioned list of polymers is not exhaustive, and a variety of other synthetic hydrophilic polymers may be used, as will be appreciated by those skilled in the art.

Other suitable synthetic hydrophilic polymers include chemically synthesized polypeptides, particularly polynucleophilic polypeptides that have been synthesized to incorporate amino acids containing primary amino groups (such as lysine) and/or amino acids containing thiol groups (such as cysteine). Poly(lysine), a synthetically produced polymer of the amino acid lysine (145 MW), is particularly preferred. Poly(lysine)s have been prepared having anywhere from 6 to about 4,000 primary amino groups, corresponding to molecular weights of about 870 to about 580,000. Poly(lysine)s for use in the present invention preferably have a molecular weight within the range of about 1,000 to about 300,000, more preferably within the range of about 5,000 to about 100,000, and most preferably, within the range of about 8,000 to about 15,000. Poly(lysine)s of varying molecular weights are commercially available from Peninsula Laboratories, Inc. (Belmont, Calif).

The synthetic hydrophilic polymer may be a homopolymer, a block copolymer, a random copolymer, or a graft copolymer. In addition, the polymer may be linear or branched, and if branched, may be minimally to highly branched, dendrimeric, hyperbranched, or a star polymer. The polymer may include biodegradable segments and blocks, either distributed throughout the polymer's molecular structure or present as a single block, as in a block copolymer. Biodegradable segments are those that degrade so as to break covalent bonds. Typically, biodegradable segments are segments that are hydrolyzed in the presence of water and/or enzymatically cleaved in situ. Biodegradable segments may be composed of small molecular segments such as ester linkages, anhydride linkages, ortho ester linkages, ortho carbonate linkages, amide linkages, phosphonate linkages, etc. Larger biodegradable "blocks" will generally be composed of oligomeric or polymeric segments incorporated within the hydrophilic polymer. Illustrative oligomeric and polymeric segments that are biodegradable include, by way of example, poly(amino acid) segments, poly(orthoester) segments, poly(orthocarbonate) segments, and the like.

Although a variety of different synthetic hydrophilic polymers can be used in the present compositions, as indicated above, preferred synthetic hydrophilic polymers are polyethylene glycol (PEG) and polyglycerol (PG), particularly highly branched polyglycerol. Various forms of PEG are extensively used in the modification of biologically active molecules because PEG lacks toxicity, antigenicity, and immunogenicity (i.e., is biocompatible), can be formulated so as to have a wide range of solubilities, and does not typically interfere with the enzymatic activities and/or conformations of peptides. A particularly preferred synthetic hydrophilic polymer for certain applications is a polyethylene glycol (PEG) having a molecular weight within the range of about 100 to about 100,000 mol. wt., although for highly branched PEG, far higher molecular weight polymers can be employed—up to 1,000,000 or more—providing that biodegradable sites are incorporated ensuring that all degradation products will have a molecular weight of less than about 30,000. For most PEGs, however, the preferred molecular weight is about 1,000 to about 20,000 mol. wt., more preferably within the range of about 7,500 to about 20,000 mol. wt. Most preferably, the polyethylene glycol has a molecular weight of approximately 10,000 mol. wt.

Naturally occurring hydrophilic polymers include, but are not limited to: proteins such as collagen, fibronectin, albumins, globulins, fibrinogen, fibrin and thrombin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin, sulfate A, B, or C, keratin sulfate, keratosulfate and heparin; and activated polysaccharides such as dextran and starch derivatives. Collagen and glycosaminoglycans are preferred naturally occurring hydrophilic polymers for use herein.

In general, collagen from any source may be used in the compositions of the invention; for example, collagen may be extracted and purified from human or other mammalian source, such as bovine or porcine corium and human placenta, or may be recombinantly or otherwise produced. The preparation of purified, substantially non-antigenic collagen in solution from bovine skin is well known in the art. Commonly owned U.S. Pat. No. 5,428,022, issued Jun. 27, 1995 to Palefsky et al., discloses methods of extracting and purifying collagen from the human placenta. Commonly owned U.S. Pat. No. 5,667,839, issued Sep. 16, 1997 to Berg, discloses methods of producing recombinant human collagen in the milk of transgenic animals, including transgenic cows. The term "collagen" or "collagen material" as used herein refers to all forms of collagen, including those that have been processed or otherwise modified.

Collagen of any type, including, but not limited to, types I, II, III, IV, or any combination thereof, may be used in the compositions of the invention, although type I is generally preferred. Either atelopeptide or telopeptide-containing collagen may be used, however, when collagen from a source, such as bovine collagen, is used, atelopeptide collagen is generally preferred, because of its reduced immunogenicity compared to telopeptide-containing collagen.

Collagen that has not been previously crosslinked by methods such as heat, irradiation, or chemical crosslinking agents is preferred for use in the compositions of the invention, although previously crosslinked collagen may be used. Non-crosslinked atelopeptide fibrillar collagen is commercially available from Cohesion Corporation (Palo Alto, Calif.) at collagen concentrations of 35 mg/ml and 65 mg/ml under the trademarks Zyderm® I Collagen and Zyderm® II Collagen, respectively. Glutaraldehyde-crosslinked atelopeptide fibrillar collagen is commercially available from Cohesion Corporation at a collagen concentration of 35 mg/ml under the trademark Zyplast®.

Collagens for use in the present invention are generally, although not necessarily, in aqueous suspension at a concentration between about 20 mg/ml to about 120 mg/ml, preferably between about 30 mg/ml to about 90 mg/ml.

Although intact collagen is preferred, denatured collagen, commonly known as gelatin, can also be used in the compositions of the invention. Gelatin may have the added benefit of being degradable faster than collagen.

Because of its tacky consistency, nonfibrillar collagen is generally preferred for use in compositions of the invention that are intended for use as bioadhesives. The term "nonfibrillar collagen" refers to any modified or unmodified collagen material that is in substantially nonfibrillar form at pH 7, as indicated by optical clarity of an aqueous suspension of the collagen.

Collagen that is already in nonfibrillar form may be used in the compositions of the invention. As used herein, the term "nonfibrillar collagen" is intended to encompass collagen types that are nonfibrillar in native form, as well as collagens that have been chemically modified such that they are in nonfibrillar form at or around neutral pH. Collagen types that are nonfibrillar (or rnicrofibrillar) in native form include types IV, VI, and VII.

Chemically modified collagens that are in nonfibrillar form at neutral pH include succinylated collagen and methylated collagen, both of which can be prepared according to the methods described in U.S. Pat. No. 4,164,559, issued Aug. 14, 1979, to Miyata et al., which is hereby incorporated by reference in its entirety. Due to its inherent tackiness, methylated collagen is particularly preferred for use in bioadhesive compositions, as disclosed in commonly owned U.S. Pat. No. 5,614,587 to Rhee et al.

Collagens for use in the crosslinkable compositions of the present invention may start out in fibrillar form, then rendered nonfibrillar by the addition of one or more fiber disassembly agent. The fiber disassembly agent must be present in an amount sufficient to render the collagen substantially nonfibrillar at pH 7, as described above. Fiber disassembly agents for use in the present invention include, without limitation, various biocompatible alcohols, amino acids, inorganic salts, and carbohydrates, with biocompatible alcohols being particularly preferred. Preferred biocompatible alcohols include glycerol and propylene glycol. Non-biocompatible alcohols, such as ethanol, methanol, and isopropanol, are not preferred for use in the present invention, due to their potentially deleterious effects on the body of the patient receiving them. Preferred amino acids include arginine. Preferred inorganic salts include sodium chloride and potassium chloride. Although carbohydrates, such as various sugars including sucrose, may be used in the practice of the present invention, they are not as preferred as other types of fiber disassembly agents because they can have cytotoxic effects in vivo.

Because it is opaque and less tacky than nonfibillar collagen, fibrillar collagen is less preferred for use in bioadhesive compositions. However, as disclosed in commonly owned, U.S. application Ser. No. 08/476,825, fibrillar collagen, or mixtures of nonfibrillar and fibrillar collagen, may be preferred for use in adhesive compositions intended for long-term persistence in vivo, if optical clarity is not a requirement.

For those compositions intended to be used in tissue augmentation, fibrillar collagen is preferred because it tends to form stronger crosslinked gels having greater long-term persistency in vivo than those prepared using nonfibrillar collagen.

Any of the hydrophilic polymers herein must contain, or be activated to contain, functional groups, i.e., nucleophilic or electrophilic groups, which enable crosslinking. Activation of PEG is discussed below; it is to be understood, however, that the following discussion is for purposes of illustration and analogous techniques may be employed with other polymers.

With respect to PEG, first of all, various functionalized polyethylene glycols have been used effectively in fields such as protein modification (see Abuchowski et al., Enzymes as Drugs, John Wiley & Sons: New York, N.Y. (1981) pp. 367–383; and Dreborg et al., Crit. Rev. Therap. Drug Carrier Syst. (1990) 6:315), peptide chemistry (see Mutter et al., The Peptides, Academic: New York, N.Y. 2:285–332; and Zalipsky et al., Int. J. Peptide Protein Res. (1987) 30:740), and the synthesis of polymeric drugs (see Zalipsky et al., Eur. Polym. J. (1983) 19:1177; and Ouchi et al., J. Macromol. Sci. Chem. (1987) A24: 1011).

Activated forms of PEG, including multifunctionally activated PEG, are commercially available, and are also easily prepared using known methods. For example, see Chapter 22 of Poly(ethylene Glycol) Chemistry: Biotechnical and Biomedical Applications, J. Milton Harris, ed., Plenum Press, NY (1992); and Shearwater Polymers, Inc. Catalog, Polyethylene Glycol Derivatives, Huntsville, Alabama (1997–1998).

Structures for some specific, tetrafunctionally activated forms of PEG are shown in FIGS. 1 to 10, as are generalized reaction products obtained by reacting the activated PEGs with multi-amino PEGs, i.e., a PEG with two or more primary amino groups. The activated PEGs illustrated have a pentaerythritol (2,2-bis(hydroxymethyl)-1,3-propanediol) core. Such activated PEGs, as will be appreciated by those in the art, are readily prepared by conversion of the exposed hydroxyl groups in the PEGylated polyol (i.e., the terminal hydroxyl groups on the PEG chains) to carboxylic acid groups (typically by reaction with an anhydride in the presence of a nitrogenous base), followed by esterification with N-hydroxysuccinimide, N-hydroxysulfosuccinimide, or the like, to give the polyfunctionally activated PEG.

FIG. 1 shows the reaction of tetrafunctionally activated PEG succinimidyl glutarate, referred to herein as "SG-PEG," with multi-amino PEG, and the reaction product obtained thereby.

Figure 2:
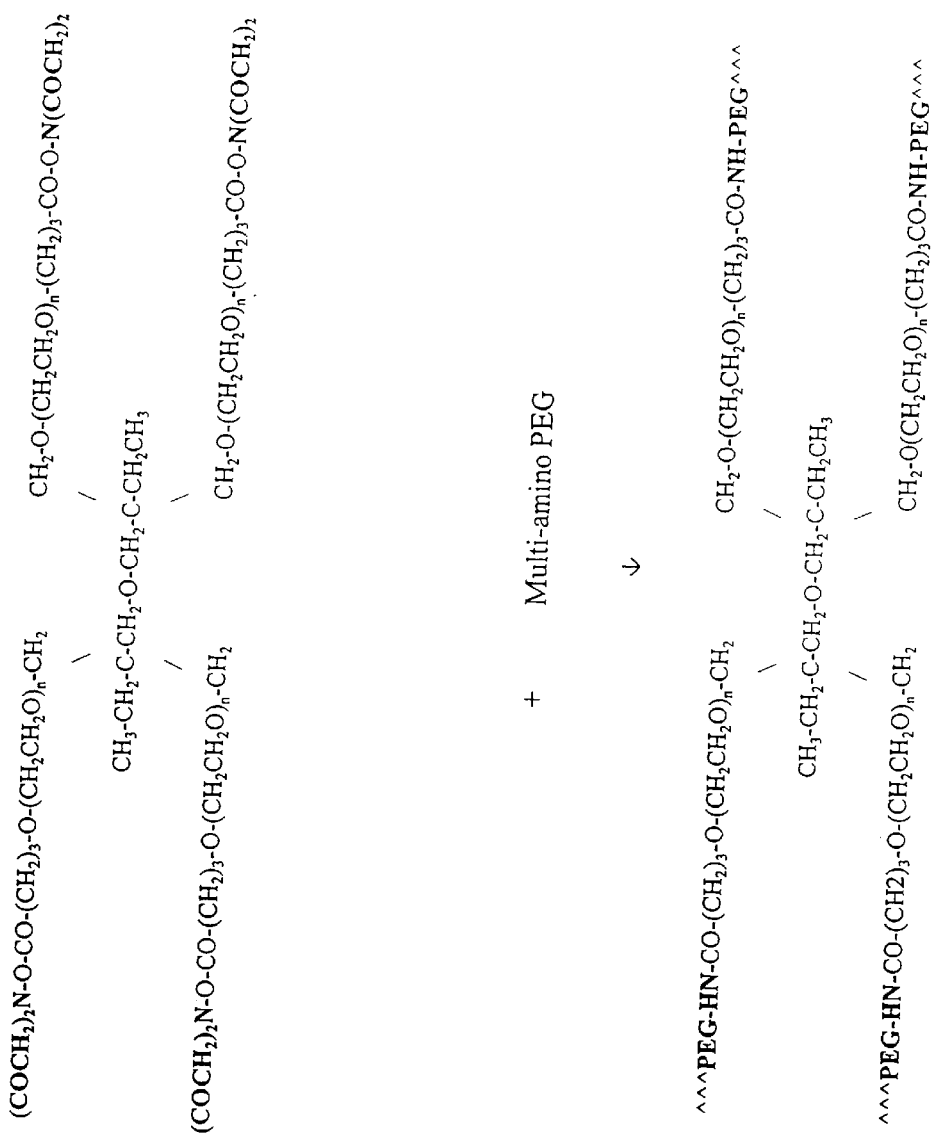

Another activated form of PEG is PEG succinimidyl propionate ("SE-PEG"). The structural formula for tetrafunctionally activated SE-PEG and the reaction product obtained upon reaction with multi-amino PEG are shown in FIG. 2.

Figure 3:
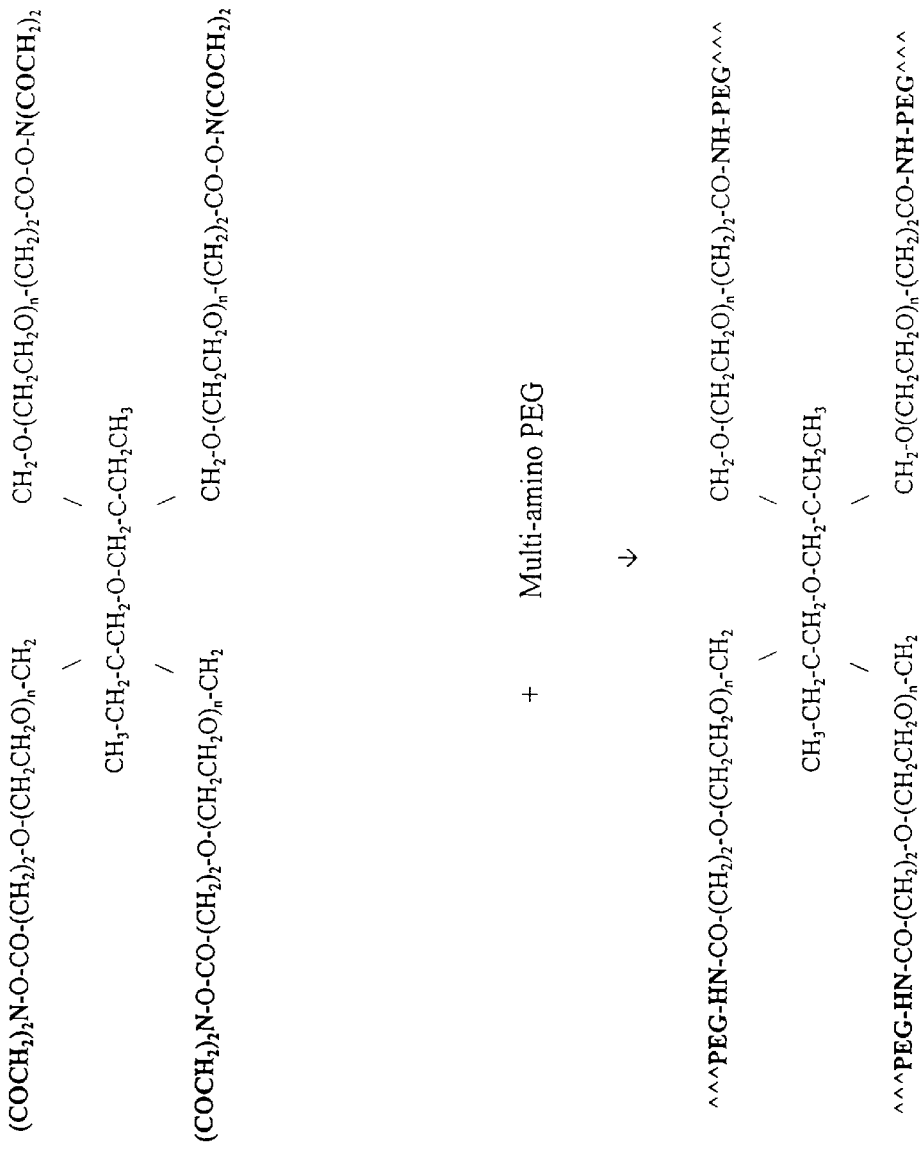
Figure 4:
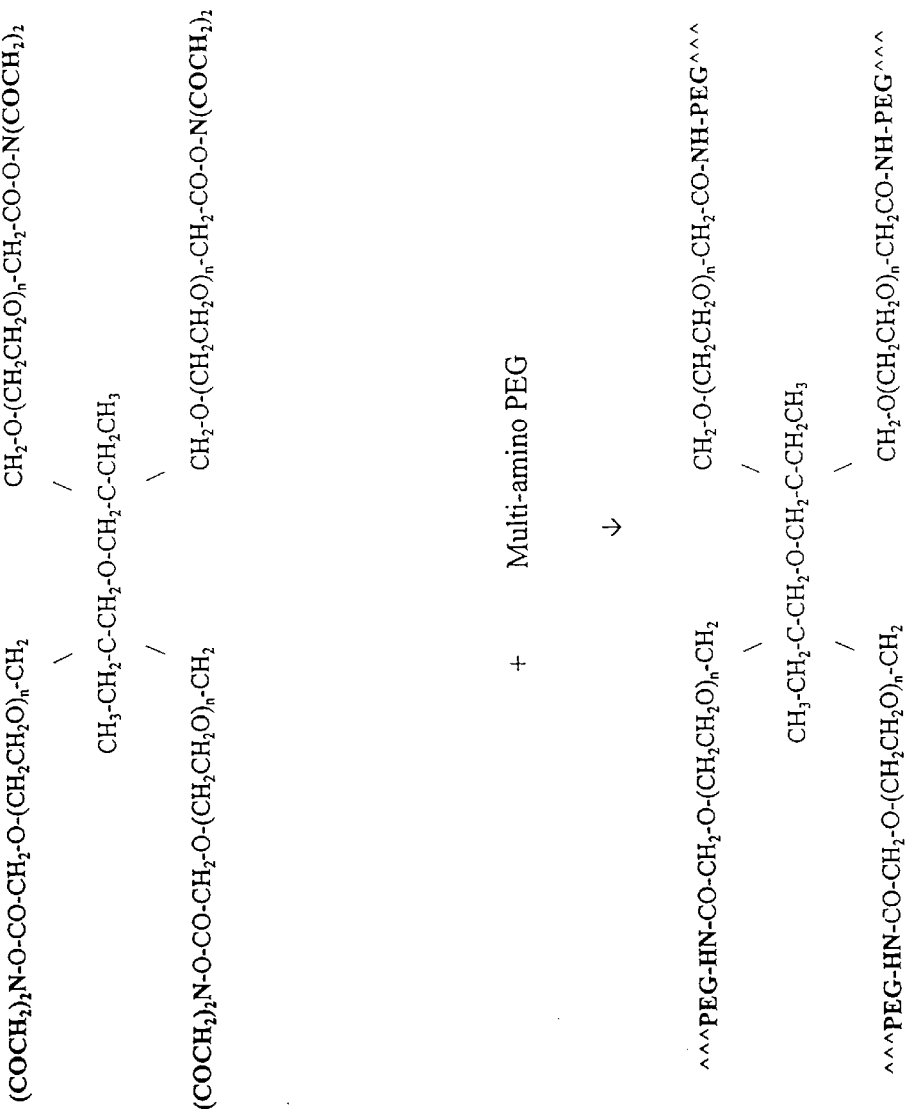

Analogous activated forms of PEG are PEG succinimidyl butylate and PEG succinimidyl acetate, the structures of which are shown in FIGS. 3 and 4, respectively, along with the reaction products obtained upon reaction with multi-amino PEG. SE-PEG, PEG succinimidyl butylate, and PEG succinimidyl acetate are sometimes referred to as "PEG succinimidyl" (PEG-S); see U.S. Pat. No. 5,328,955 to Rhee et al.

Figure 5:
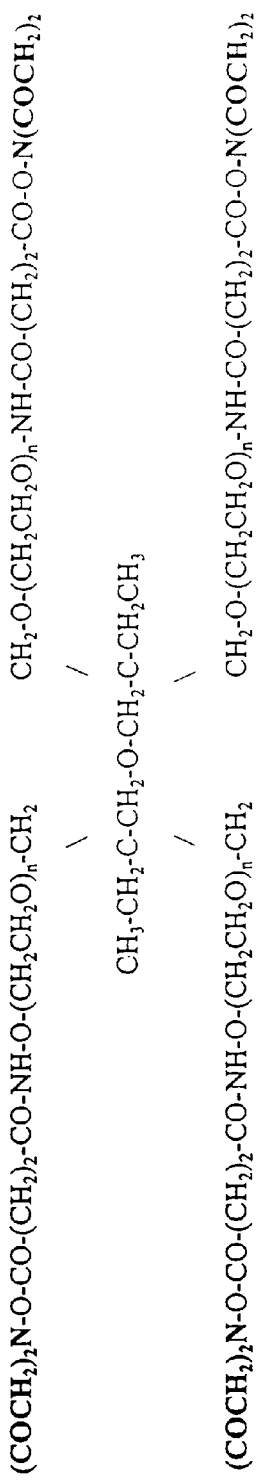
Figure 5:
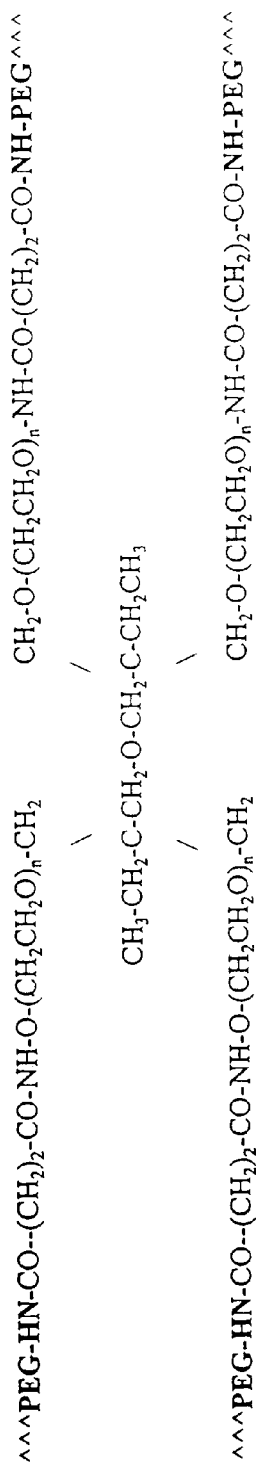

Another functionally activated form of PEG is referred to as "PEG succinimidyl succinamide" (SSA-PEG). The structural formula for the tetrafunctionally activated form of this compound and the reaction product obtained by reacting it with multi-amino PEG are shown in FIG. 5. In the structure of FIG. 5, an ethylene ($-CH_2CH_2-$) group is shown adjacent to the succinimidyl ester; it is to be understood, however, that as with the PEG succinimidyl compounds, related structures containing a methylene linkage, an n-propylene linkage, or the like, are also possible.

Figure 6:
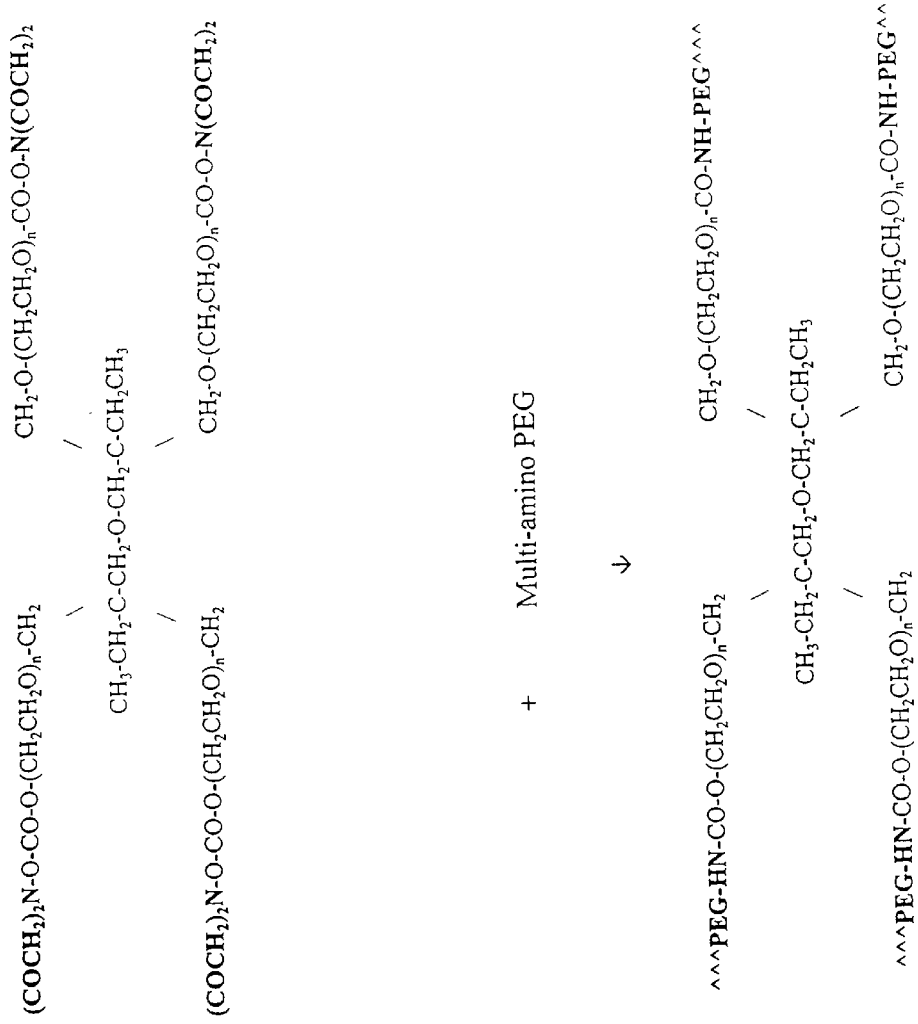

Yet another activated form of PEG is PEG succinimidyl carbonate (SC-PEG). The structural formula of tetrafunctionally activated SC-PEG and the conjugate formed by reacting it with multi-amino PEG are shown in FIG. 6.

Figure 7:
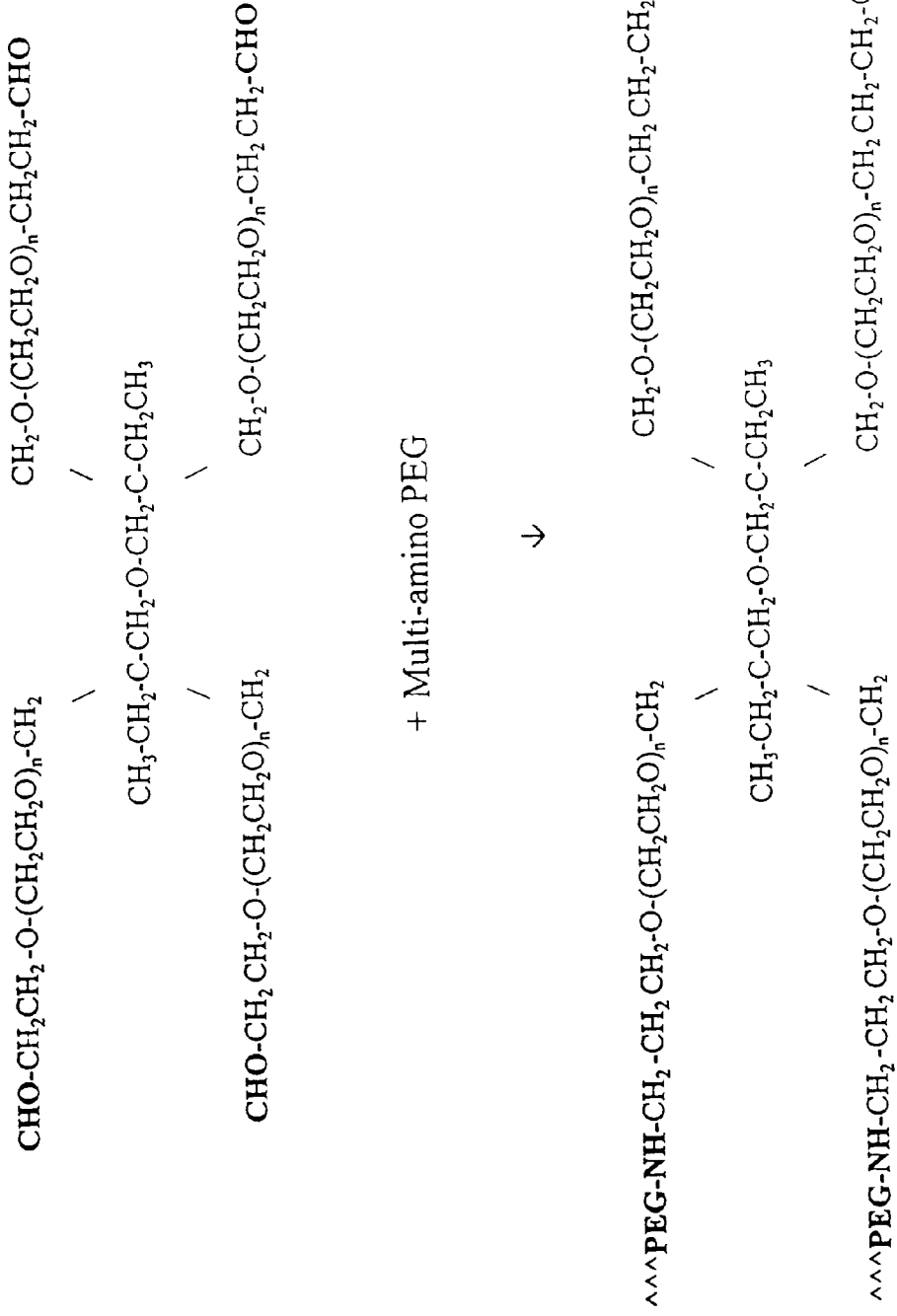

PEG can also be derivatized to form functionally activated PEG propionaldehyde (A-PEG), the tetrafunctionally activated form of which is shown in FIG. 7, as is the conjugate formed by the reaction of A-PEG with multi-amino PEG.

Figure 8:
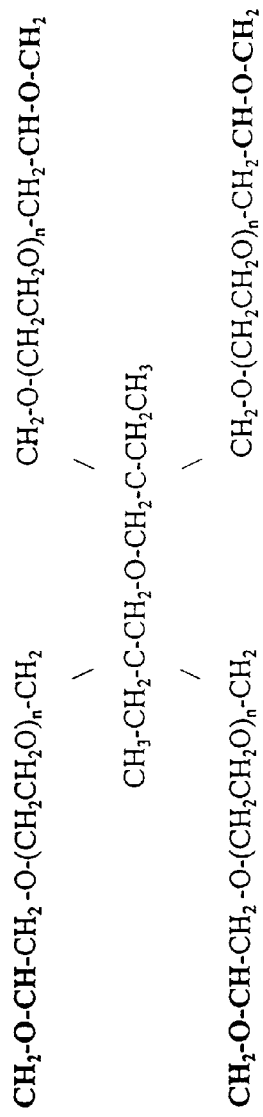
Figure 8:
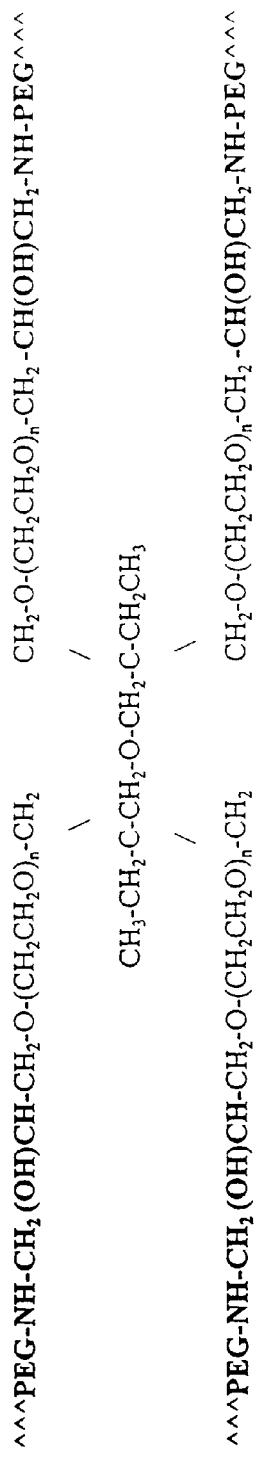

Yet another form of activated polyethylene glycol is functionally activated PEG glycidyl ether (E-PEG), of which the tetrafunctionally activated compound is shown in FIG. 8, as is the conjugate formed by reacting such with multi-amino PEG.

Figure 9:
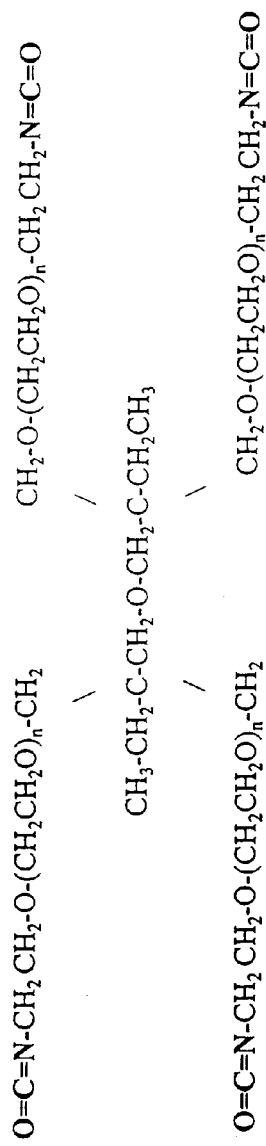
Figure 9:
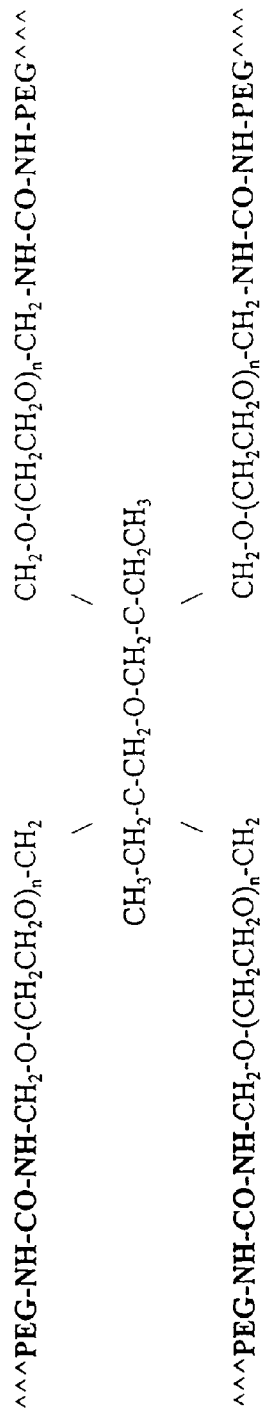

Another activated derivative of polyethylene glycol is functionally activated PEG-isocyanate (I-PEG), which is shown in FIG. 9, along with the conjugate formed by reacting such with multi-amino PEG.

Figure 10:
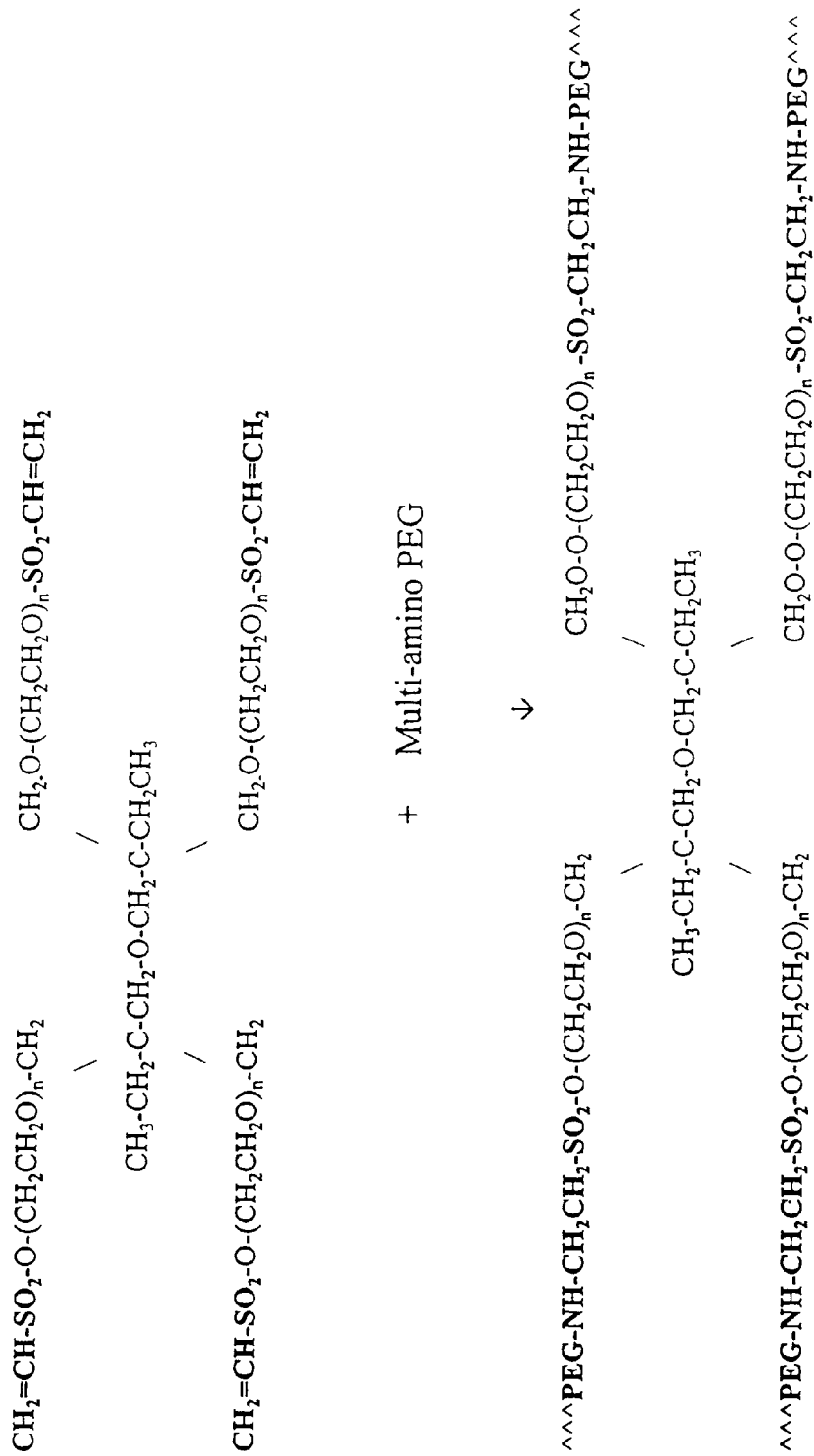
Figure 11:
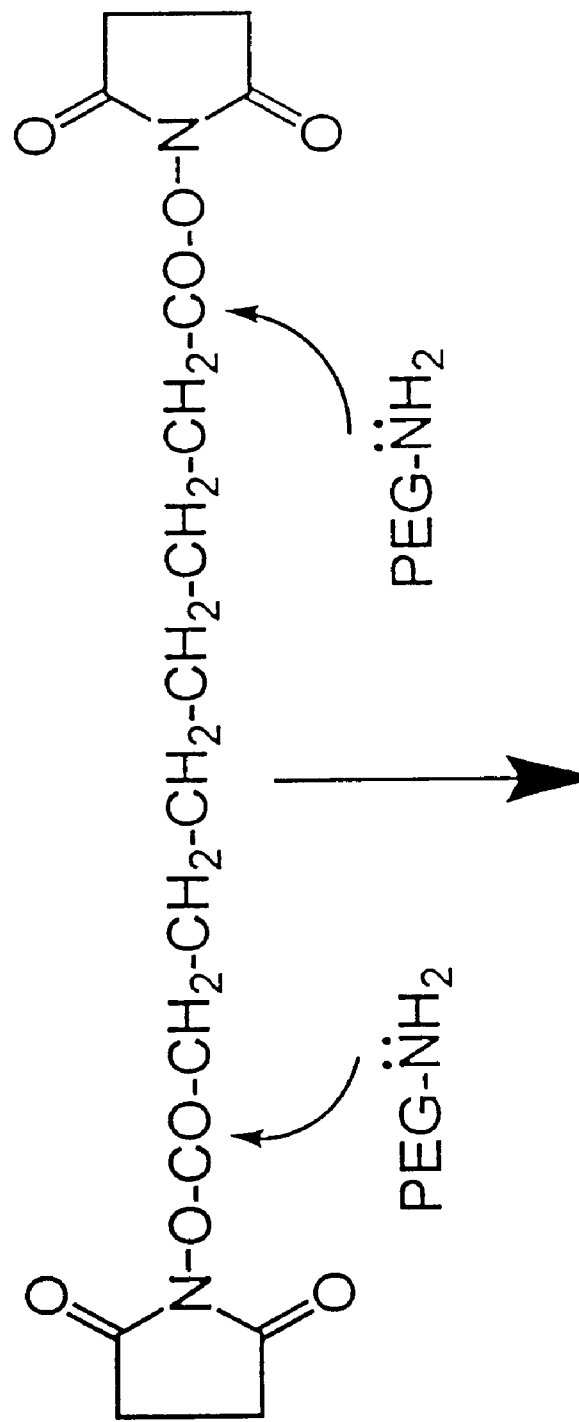
Figure 12:
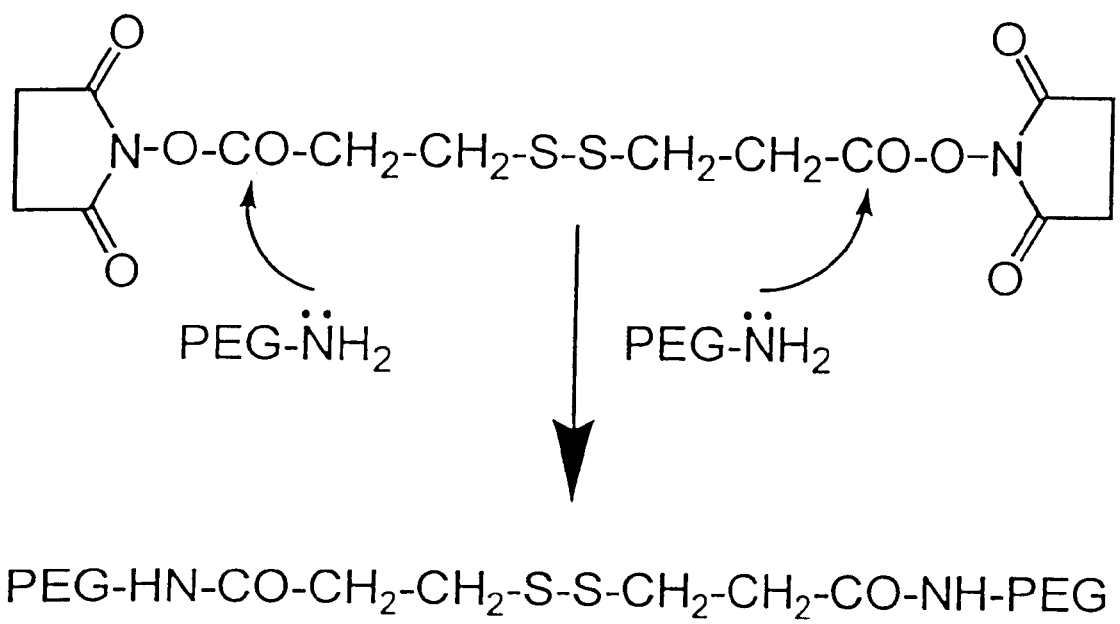
Figure 13:
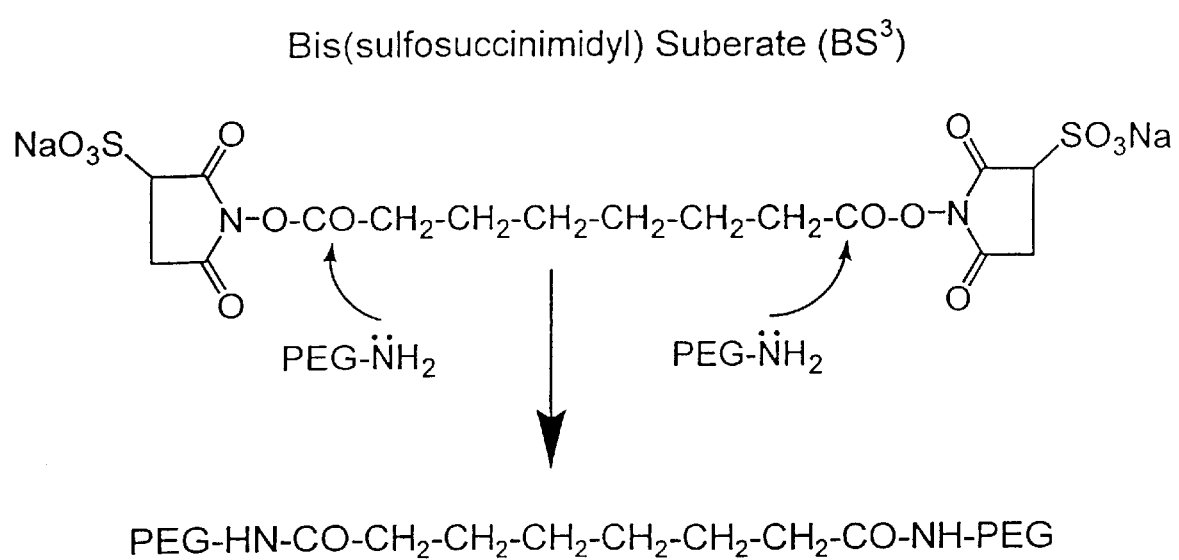
Figure 14:
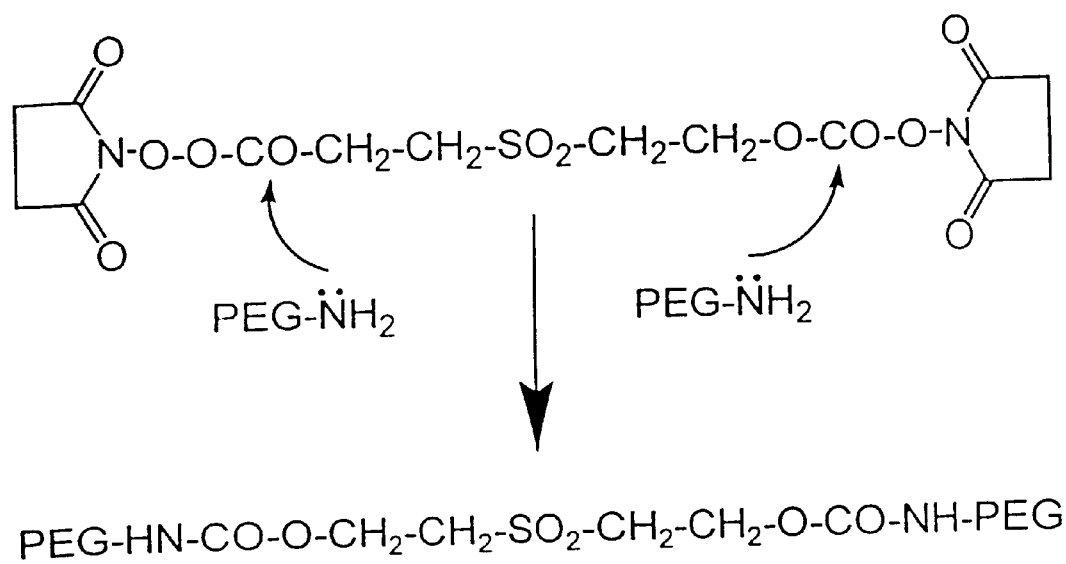

Another activated derivative of polyethylene glycol is functionally activated PEG-vinylsulfone (V-PEG), which is shown in FIG. 10, along with the conjugate formed by reacting such with multi-amino PEG.

Activation with succinimidyl groups to convert terminal hydroxyl groups to reactive esters is one technique for preparing a synthetic hydrophilic polymer with electrophilic moieties suitable for reaction with nucleophiles such as primary amines, thiols, and hydroxyl groups. Other activating agents for hydroxyl groups include carbonyldiimidazole and sulfonyl chloride. However, as discussed in part (B) of this section, a wide variety of electrophilic groups may be advantageously employed for reaction with corresponding nucleophiles. Examples of such electrophilic groups include acid chloride groups; anhydrides, ketones, aldehydes, isocyanate, isothiocyanate, epoxides, and olefins, including conjugated olefins such as ethenesulfonyl ($-SO_2CH=CH_2$) and analogous functional groups.

Hydrophilic di- or poly-nucleophilic polymers of the present composition are exemplified in FIGS. 1-10 by multi-amino PEG. Various forms of multi-amino PEG are commercially available from Shearwater Polymers (Huntsville, Ala.) and from Texaco Chemical Company (Houston, Tex.) under the name "Jeffamine". Multi-amino PEGs useful in the present invention include Texaco's Jeffamine diamines ("D" series) and triamines ("T" series), which contain two and three primary amino groups per molecule. Analogous poly(sulfhydryl) PEGs are also available from Shearwater Polymers, e.g., in the form of pentaerythritol poly(ethylene glycol) ether tetra-sulfhydryl (molecular weight 10,000).

2. HYDROPHOBIC POLYMERS

The crosslinkable compositions of the invention can also include hydrophobic polymers, although for most uses hydrophilic polymers are preferred. Polylactic acid and polyglycolic acid are examples of two hydrophobic polymers that can be used. With other hydrophobic polymers, only short-chain oligomers should be used, containing at most about 14 carbon atoms, to avoid solubility-related problems during reaction.

3. LOW MOLECULAR WEIGHT COMPONENTS

As indicated above, the molecular core of one or two of the crosslinkable components can also be a low molecular weight compound, i.e., a $C_2-C_{14}$ hydrocarbyl group containing zero to 2 heteroatoms selected from N, O, S and combinations thereof Such a molecular core can be substituted with nucleophilic groups or with electrophilic groups.

When the low molecular weight molecular core is substituted with primary amino groups, the component may be, for example, ethylenediamine ($H_2N-CH_2CH_2-NH_2$), tetramethylenediamine ($H_2N-(CH_4)-NH_2$), pentamethylenediamine (cadaverine) ($H_2N-(CH_5)-NH_2$), hexamethylenediamine ($H_2N-(CH6)-NH_2$), bis(2-aminoethyl) amine ($HN-[CH_2CH_2-NH_2]_2$), or tris(2-aminoethyl) amine ($N-[CH_2CH_2-NH_2]_3$).

Low molecular weight diols and polyols include trimethylolpropane, di(trimethylol propane), pentaerythritol, and diglycerol, all of which require activation with a base in order to facilitate their reaction as nucleophiles. Such diols and polyols may also be functionalized to provide di- and poly-carboxylic acids, functional groups that are, as noted earlier herein, also useful as nucleophiles under certain conditions. Polyacids for use in the present compositions include, without limitation, trimethylolpropane-based tricarboxylic acid, di(trimethylol propane)-based tetracarboxylic acid, heptanedioic acid, octanedioic acid (suberic acid), and hexadecanedioic acid (thapsic acid), all of which are commercially available and/or readily synthesized using known techniques.

Low molecular weight di- and poly-electrophiles include, for example, disuccinimidyl suberate (DSS), bis(sulfosuccinimidyl) suberate ($BS_3$), dithiobis (succinimidylpropionate) (DSP), bis(2-succinimidooxycarbonyloxy) ethyl sulfone (BSOCOES), and 3,3'-dithiobis(sulfosuccinimidylpropionate (DTSPP), and their analogs and derivatives. The aforementioned compounds are commercially available from Pierce (Rockford, Ill.). Such di- and poly-electrophiles can also be synthesized from di- and polyacids, for example by reaction with an appropriate molar amount of N-hydroxysuccinimide in the presence of DCC. Polyols such as trimethylolpropane and di(trimethylol propane) can be converted to carboxylic acid form using various known techniques, then further derivatized by reaction with NHS in the presence of DCC to produce trifunctionally and tetrafunctionally activated polymers.

D. STORAGE AND HANDLING

Because crosslinkable components containing electrophilic groups react with water, the electrophilic component or components are generally stored and used in sterile, dry form to prevent hydrolysis. Processes for preparing synthetic hydrophilic polymers containing multiple electrophilic groups in sterile, dry form are set forth in commonly assigned U.S. Pat. No. 5,643,464 to Rhee et al. For example, the dry synthetic polymer may be compression molded into a thin sheet or membrane, which can then be sterilized using gamma or, preferably, e-beam irradiation. The resulting dry membrane or sheet can be cut to the desired size or chopped into smaller size particulates.

Components containing multiple nucleophilic groups are generally not water-reactive and can therefore be stored either dry or in aqueous solution. If stored as a dry, particulate, solid, the various components of the crosslinkable composition may be blended and stored in a single container. Admixture of all components with water, saline, or other aqueous media should not occur until immediately prior to use.

In an alternative embodiment, both components can be mixed together in a single aqueous medium in which they are both unreactive, i.e. such as in a low pH buffer. Thereafter, they can be sprayed onto the targeted tissue site along with a high pH buffer, after which they will rapidly react and form a gel.

Suitable liquid media for storage of crosslinkable compositions include aqueous buffer solutions such as monobasic sodium phosphate/dibasic sodium phosphate, sodium carbonate/sodium bicarbonate, glutamate or acetate, at a concentration of 0.5 to 300 mM. I 0 In general, a sulfhydryl-reactive component such as PEG substituted with maleimido groups or succinimidyl esters is prepared in water or a dilute buffer, with a pH of between around 5 to 6. Buffers with pKs between about 8 and 10.5 for preparing a polysulfhydryl component such as sulfhydryl-PEG are useful to achieve fast gelation time of compositions containing mixtures of sulfhydryl-PEG and SG-PEG. These include carbonate, borate and ANPSO (3-[(1,1-dimethyl-2-hydroxyethyl) amino]2-hydroxy-propane-sulfonic acid). In contrast, using a combination of maleimidyl PEG. and sulfhydryl-PEG, a pH of around 5 to 9 is preferred for the liquid medium used to prepare the sulfhydryl PEG. A particularly preferred composition for hemostatic applications to actively bleeding tissue sites comprises a mixture of maleimidyl and succinimidyl PEG as the first component, and sulfflydryl PEG as the second component. Such compositions produce gels with enhanced biodegradability and superior gel times when compared to compositions having only maleimidyl PEG or succinimicyl PEG alone.

E. OTHER COMPONENTS OF THE CROSSLINKABLE COMPOSITION

In order to enhance matrix strength, it may be generally desirable to add a "tensile strength enhancer" to the composition. Such tensile strength enhancers preferably comprise micron-size, preferably 5 to 40 microns in diameter and 20 to 5000 microns in length, high tensile strength fibers, usually with glass transition temperatures well above 37° C.

Suitable tensile strength enhancers for use in the present invention include, inter alia, collagen fibers, polyglycolide and polylactide fibers, as well as other organic tensile strength enhancers and inorganic tensile strength enhancers. A particularly useful tensile strength enhancer is Vicryl® (polyglycolide:polylactide, 90: 10) The use of tensile strength enhancers, which are part of the broader category of "fillers," are well known. For example, silicone gums, when cross-linked with peroxides, are weak gels a with tensile strength on the order of only about 34 $N/cm^2$. When suitably compounded with reinforcing fillers, the tensile strength of these gums may increase as much as fifty-fold. Lichtenwalner, H. K. and Sprung, M. N., in Mark, H. F., Gaylord, N. G., and Bikales, N. M., Eds., Encyclopedia of Polymer Science and Technology, Vol. 12, p. 535, John Wiley, New York, 1970. Suitable tensile strength enhancers are those that have inherent high tensile strength and also can interact by covalent or non-covalent bonds with the polymerized gel network. The tensile strength enhancer should bond to the gel, either mechanically or covalently, in order to provide tensile-support. Tensile strengths of polyglycolide resorbable sutures are approximately 89,000 $N/cm^2$; that of collagen fibers is 5000–10,000 $N/cm^2$ (Hayashi, T., in Biomedical Applic. of Polym. Mater., Tsuruta, T. et al., Eds., CRC Press, Boca Raton, Fla., 1993).

The crosslinkable compositions can also be prepared to contain various imaging agents such as iodine or barium sulfate, or fluorine, in order to aid visualization of the compositions after administration via X-ray or $^{19}$F-MRI, respectively.

For use in tissue adhesion as discussed below, it may also be desirable to incorporate proteins such as albumin, fibrin or fibrinogen into the crosslinked polymer composition to promote cellular adhesion.

In addition, the introduction of hydrocolloids such as carboxymethylcellulose may promote tissue adhesion and/or swellability.

III. Crosslinking

Any number of crosslinking techniques may be used to effect crosslinking of the aforementioned compositions. Generally, however, components A, B and C are selected such that crosslinking occurs fairly rapidly upon admixture of all components of the crosslinkable composition with an aqueous medium.

For crosslinking compositions in which one or more components contain hydroxyl and/or thiol groups as nucleophilic moieties, the aqueous medium with which the crosslinking composition (or components thereof) are admixed should contain a basic reagent that is effective to increase the nucleophilic reactivity of the hydroxyl and/or thiol group (and thus the rate of the nucleophile-electrophile reactions) but that is preferably non-nucleophilic so as to avoid reaction with any electrophilic groups present. A catalytic amount of base can be used, and/or a base-containing buffer. In an alternative but less preferred embodiment, a reactive base can be used that participates as a reactant in the crosslinking reaction.

In general, the combined concentration of all crosslinkable components in the aqueous admixture will be in the range of about 1 to 50 wt. %, generally about 2 to 40 wt. %. However, a preferred concentration of the crosslinkable composition in the aqueous medium—as well as the preferred concentration of each crosslinkable component therein—will depend on a number of factors, including the type of component, its molecular weight, and the end use of the composition. For example, use of higher concentrations of the crosslinkable components, or using highly functionalized components, will result in the formation of a more tightly crosslinked network, producing a stiffer, more robust gel. As such, compositions intended for use in tissue augmentation will generally employ concentrations of crosslinkable components that fall toward the higher end of the preferred concentration range. Compositions intended for use as bioadhesives or in adhesion prevention do not need to be as firm and may therefore contain lower concentrations of the crosslinkable components. The appropriate concentration of each crosslinkable component can easily be optimized to achieve a desired gelation time and gel strength using routine experimentation.

IV. Administration and Use

The compositions of the present invention may be administered before, during or after crosslinking. Certain uses, which are discussed in greater detail below, such as tissue augmentation, may require the compositions to be crosslinked before administration, whereas other applications, such as tissue adhesion, require the compositions to be administered before crosslinking has reached "equilibrium." The point at which crosslinking has reached equilibrium is defined herein as the point at which the composition no longer feels tacky or sticky to the touch.

The compositions of the present invention are generally delivered to the site of administration in such a way that the individual components of the composition come into contact with one another for the first time at the site of administration, or immediately preceding administration. Thus, the compositions of the present invention are preferably delivered to the site of administration using an apparatus that allows the components to be delivered separately. Such delivery systems usually involve a multi-compartment spray device. Alternatively, the components can be delivered separately using any type of controllable extrusion system, or they can be delivered manually in the form of separate pastes, liquids or dry powders, and mixed together manually at the site of administration. Many devices that are adapted for delivery of multi-component tissue sealants/hemostatic agents are well known in the art and can also be used in the practice of the present invention.

Yet another way of delivering the compositions of the present invention is to prepare the reactive components in inactive form as either a liquid or powder. Such compositions can then be activated after application to the tissue site, or immediately beforehand, by applying an activator. In one embodiment, the activator is a buffer solution having a pH that will activate the composition once mixed therewith. Still another way of delivering the compositions is to prepare preformed sheets, and apply the sheets as such to the site of administration.

The crosslinkable compositions of the present invention can be used in a variety of different applications. In general, the present compositions can be adapted for use in any tissue engineering application where synthetic gel matrices are currently being utilized. For example, the compositions of the present invention are useful as tissue sealants, in tissue augmentation, in tissue repair, as hemostatic agents, in preventing tissue adhesions, in providing surface modifications, and in drug/cell/gene delivery applications. One of skill in the art can easily determine the appropriate administration protocol to use with any particular composition having a known gel strength and gelation time. A more detailed description of several specific applications is given below:

Tissue Sealants and Adhesives: In a preferred application, the compositions described herein can be used for medical conditions that require a coating or sealing layer to prevent the leakage of gases, liquid or solids. The method entails applying both components to the damaged tissue or organ to seal 1) vascular and or other tissues or organs to stop or minimize the flow of blood, 2) thoracic tissue to stop or minimize the leakage of air; 3) gastrointestinal tract or pancreatic tissue to stop or minimize the leakage of fecal or tissue contents; 4) bladder or ureters to stop or minimize the leakage of urine; 5) dura to stop or minimize the leakage of CSF; and 6) skin or serosal tissue to stop the leakage of serosal fluid. These compositions may also be used to adhere tissues together such as small vessels, nerves or dermal tissue. The material can be used 1) by applying it to the surface of one tissue and then a second tissue may be rapidly pressed against the first tissue or 2) by bringing the tissues in close juxtaposition and then applying the material. In addition, the compositions can be used to fill spaces in soft and hard tissues that are created by disease or surgery.

Biologically Active Agent Delivery: The crosslinked compositions of the invention may also be used for localized delivery of various drugs and other biologically active agents. Biologically active agents such as growth factors may be delivered from the composition to a local tissue site in order to facilitate tissue healing and regeneration.

The term "biologically active agent" refers to an organic molecule that exerts biological effects in vivo. Examples of biologically active agents include, without limitation, enzymes, receptor antagonists or agonists, hormones, growth factors, autogenous bone marrow, antibiotics, antimicrobial agents and antibodies. The term "biologically active agent" is also intended to encompass various cell types and genes that can be incorporated into the compositions of the invention.

Preferred biologically active agents for use in the compositions of the present invention are cytokines, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are particularly preferred. Members of the TGF supergene family include the beta transforming growth factors (for example TGF-.beta. 1, TGF-.beta.2, TGF-.beta.3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Biologically active agents may be incorporated into the crosslinked synthetic polymer composition by admixture. Alternatively, the agents may be incorporated into the crosslinked polymer matrix by binding these agents to the fuinctional groups on the synthetic polymers. Processes for covalently binding biologically active agents such as growth factors using functionally activated polyethylene glycols are described in commonly assigned U.S. Pat. No. 5,162,430, issued Nov. 10, 1992, to Rhee et al. Such compositions preferably include linkages that can be easily biodegraded, for example as a result of enzymatic degradation, resulting in the release of the active agent into the target tissue, where it will exert its desired therapeutic effect.

A simple method for incorporating biologically active agents containing nucleophilic groups into the crosslinked polymer composition involves mixing the active agent with a polyelectrophilic component prior to addition of the polynucleophilic component.

By varying the relative molar amounts of the different components of the crosslinkable composition, it is possible to alter the net charge of the resulting crosslinked polymer composition, in order to prepare a matrix for the delivery of a charged compound such as a protein or ionizable drug. As such, the delivery of charged proteins or drugs, which would normally diffuse rapidly out of a neutral carrier matrix, can be controlled.

For example, if a molar excess of a polynucleophilic component is used, the resulting matrix has a net positive charge and can be used to ionically bind and deliver negatively charged compounds. Examples of negatively charged compounds that can be delivered from these matrices include various drugs, cells, proteins, and polysaccharides. Negatively charged collagens, such as succinylated collagen, and glycosaminoglycan derivatives such as sodium hyaluronate, keratan sulfate, keratosulfate, sodium chondroitin sulfate A, sodium dermatan sulfate B, sodium chondroitin sulfate C, heparin, esterified chondroitin sulfate C, and esterified heparin, can be effectively incorporated into the crosslinked polymer matrix as described above.

If a molar excess of a polyelectrophilic component is used, the resulting matrix has a net negative charge and can be used to ionically bind and deliver positively charged compounds. Examples of positively charged compounds that can be delivered from these matrices include various drugs, cells, proteins, and polysaccharides. Positively charged collagens, such as methylated collagen, and glycosaminoglycan derivatives such as esterified deacetylated hyaluronic acid, esterified deacetylated desulfated chondroitin sulfate A, esterified deacetylated desulfated chondroitin sulfate C, deacetylated desulfated keratan sulfate, deacetylated desulfated keratosulfate, esterified desulfated heparin, and chitosan, can be effectively incorporated into the crosslinked polymer matrix as described above, Delivery of cells and genes: The crosslinked polymer compositions of the present invention can also be used to deliver various types of living cells or genes to a desired site of administration in order to form new tissue. The term "genes" as used herein is intended to encompass genetic material from natural sources, synthetic nucleic acids, DNA, antisense-DNA and RNA.

When used to deliver cells, for example, mesenchymal stem cells can be delivered to produce cells of the same type as the tissue into which they are delivered. Mesenchymal stem cells are not differentiated and therefore can differentiate to form various types of new cells due to the presence of an active agent or the effects (chemical, physical, etc.) of the local tissue environment. Examples of mesenchymal stem cells include osteoblasts, chondrocytes, and fibroblasts. Osteoblasts can be delivered to the site of a bone defect to produce new bone; chondrocytes can be delivered to the site of a cartilage defect to produce new cartilage; fibroblasts can be delivered to produce collagen wherever new connective tissue is needed; neurectodermal cells can be delivered to form new nerve tissue; epithelial cells can be delivered to form new epithelial tissues, such as liver, pancreas, etc.

The cells or genes may be either allogeneic or xenogeneic in origin. For example, the compositions can be used to deliver cells or genes from other species that have been genetically modified. Because the compositions of the invention are not easily degraded in vivo, cells and genes entrapped within the crosslinked polymer compositions will be isolated from the patient's own cells and, as such, will not provoke an immune response in the patient. In order to entrap the cells or genes within a crosslinked polymer matrix, the cells or genes are pre-mixed with the polynucleophilic component(s), and then the polyelectrophilic component(s) are added to the mixture to form a crosslinked matrix, thereby entrapping the cells or genes within the matrix. Alternatively, the initial pre-mixing may be carried out with the polyelectrophilic component(s), followed by subsequent addition of the polynucleophilic component(s).

As discussed above for biologically active agents, when used to deliver cells or genes, the synthetic polymers preferably also contain biodegradable groups to aid in controlled release of the cells or genes at the intended site of delivery.

Bioadhesives: As used herein, the terms "bioadhesive", "biological adhesive", and "surgical adhesive" are used interchangeably to refer to biocompatible compositions capable of effecting temporary or permanent attachment between the surfaces of two native tissues, or between a native tissue surface and either a non-native tissue surface or a surface of a synthetic implant.

In a general method for effecting the attachment of a first surface to a second surface, the crosslinkable composition is applied to a first surface, which is then contacted with a second surface to effect adhesion therebetween. Preferably, all reactive components of the crosslinkable composition are first mixed to initiate crosslinking, then delivered to the first surface before substantial crosslinking has occurred. The first surface is then contacted with the second surface, preferably immediately, to effect adhesion . At least one of the first and second surfaces is preferably a native tissue surface.

The two surfaces may be held together manually, or using other appropriate means, while the crosslinking reaction is proceeding to completion. Crosslinking is typically sufficiently complete for adhesion to occur within about 5 to 60 minutes after mixing of the first and second synthetic polymers. However, the time required for complete crosslinking to occur is dependent on a number of factors, including the type and molecular weight of each reactive component, the degree of functionalization, and the concentration of the crosslinkable composition (i.e., higher concentrations result in faster crosslinking times).

At least one of the first and second surfaces is preferably a native tissue surface. As used herein, the term "native tissue" refers to biological tissues that are native to the body of the patient being treated. As used herein, the term "native tissue" is intended to include biological tissues that have been elevated or removed from one part of the body of a patient for implantation to another part of the body of the same patient (such as bone autografts, skin flap autografts, etc.). For example, the compositions of the invention can be used to adhere a piece of skin from one part of a patient's body to another part of the body, as in the case of a burn victim.

The other surface may be a native tissue surface, a non-native tissue surface, or a surface of a synthetic implant. As used herein, the term "non-native tissue" refers to biological tissues that have been removed from the body of a donor patient (who may be of the same species or of a different species than the recipient patient) for implantation into the body of a recipient patient (e.g., tissue and organ transplants). For example, the crosslinkable polymer compositions of the present invention can be used to adhere a donor cornea to the eye of a recipient patient.

As used herein, the term "synthetic implant" refers to any biocompatible material intended for implantation into the body of a patient not encompassed by the above definitions for native tissue and non-native tissue. Synthetic implants include, for example, artificial blood vessels, heart valves, artificial organs, bone prostheses, implantable lenticules, vascular grafts, stents, and stent/graft combinations, etc.

Ophthalmic Applications: Because of their optical clarity, the crosslinked polymer compositions of the invention are particularly well suited for use in ophthalmic applications. For example, a synthetic lenticule for correction of vision can be attached to the Bowman's layer of the cornea of a patient's eye using the methods of the present invention. As disclosed in commonly assigned U.S. Pat. No. 5,565,519, issued Oct. 15, 1996 to Rhee et al., a chemically modified collagen (such as succinylated or methylated collagen) that is in substantially nonfibrillar form at pH 7 can be crosslinked using a synthetic hydrophilic polymer, then molded into a desired lenticular shape and allowed to complete crosslinking. The resulting crosslinked collagen lenticule can then be attached to the Bowman's layer of a de-epithelialized cornea of a patient's eye using the methods of the present invention. By applying the reaction mixture comprising the first and second synthetic polymers to the anterior surface of the cornea, then contacting the anterior surface of the cornea with the posterior surface of the lenticule before substantial crosslinking has occurred, electrophilic groups on the second synthetic polymer will also covalently bind to collagen molecules in both the corneal tissue and the lenticule to firmly anchor the lenticule in place. Alternatively, the reaction mixture can be applied first to the posterior surface of the lenticule, which is then contacted with the anterior surface of the cornea.

The compositions of the present invention are also suitable for use in vitreous replacement.

Tissue Augmentation: The crosslinkable compositions of the invention can also be used for augmentation of soft or hard tissue within the body of a mammalian subject. As such, they may be better than currently marketed collagen-based materials for soft tissue augmentation, because they are less immunogenic and more persistent. Examples of soft tissue augmentation applications include sphincter (e.g., urinary, anal, esophageal) augmentation and the treatment of rhytids and scars. Examples of hard tissue augmentation applications include the repair and/or replacement of bone and/or cartilaginous tissue.

The compositions of the invention are particularly suited for use as a replacement material for synovial fluid in osteoarthritic joints, serving to reduce joint pain and improve joint function by restoring a soft hydrogel network in the joint. The crosslinked compositions can also be used as a replacement material for the nucleus pulposus of a damaged intervertebral disk. The nucleus pulposus of the damaged disk is first removed, and the crosslinkable composition is then injected or otherwise introduced into the center of the disk. The composition may either be crosslinked prior to introduction into the disk, or allowed to crosslink in situ.

In a general method for effecting augmentation of tissue within the body of a mammalian subject, the reactive components of the crosslinkable composition are injected simultaneously to a tissue site in need of augmentation through a small-gauge (e.g., 25–32 gauge) needle. Once inside the patient's body, the nucleophilic groups on the polynucleophilic component(s) and the electrophilic groups on the polyelectrophilic component(s) react with each other to form a crosslinked polymer network in situ. Electrophilic groups on the polyelectrophilic component(s) may also react with primary amino groups on lysine residues of collagen molecules within the patient's own tissue, providing for "biological anchoring" of the compositions with the host tissue.

Adhesion Prevention: Another use of the crosslinkable compositions of the invention is to coat tissues in order to prevent the formation of adhesions following surgery or injury to internal tissues or organs. In a general method for coating tissues to prevent the formation of adhesions following surgery, the reactive components are mixed and a thin layer of the reaction mixture is then applied to the tissues comprising, surrounding, and/or adjacent to the surgical site before substantial crosslinking has occurred. Application of the reaction mixture to the tissue site may be by extrusion, brushing, spraying (as described above), or by any other convenient means.

Following application of the reaction mixture to the surgical site, crosslinking is allowed to continue in situ prior to closure of the surgical incision. Once crosslinking has reached equilibrium, tissues that are brought into contact with the coated tissues will not adhere thereto. The surgical site can then be closed using conventional means (sutures, etc.).

In general, compositions that achieve complete crosslinking within a relatively short period of time (i.e., 5–15 minutes following admixture of the reactive components) are preferred for use in the prevention of surgical adhesions, so that the surgical site may be closed relatively soon after completion of the surgical procedure.

Coating Material for Synthetic Implants: Another use of the crosslinked polymer compositions of the invention is as a coating material for synthetic implants. In a general method for coating a surface of a synthetic implant, the reactive components of the crosslinkable composition are mixed with an aqueous medium, and a thin layer of the reaction mixture is then applied to a surface of the implant before substantial crosslinking has occurred. In order to minimize cellular and fibrous reaction to the coated implant, the reaction mixture is preferably prepared to have a net neutral charge. Application of the reaction mixture to the implant surface may be by extrusion, brushing, spraying (as described above), or by any other convenient means. Following application of the reaction mixture to the implant surface, crosslinking is allowed to continue until complete crosslinking has been achieved.

Although this method can be used to coat the surface of any type of synthetic implant, it is particularly useful for implants where reduced thrombogenicity is an important consideration, such as artificial blood vessels and heart valves, vascular grafts, vascular stents, and stent/graft combinations. The method may also be used to coat implantable surgical membranes (e.g., monofilament polypropylene) or meshes (e.g., for use in hernia repair). Breast implants may also be coated using the above method in order to minimize capsular contracture.

The compositions of the present invention may also be used to coat lenticules, which are made from either naturally occurring or synthetic polymers.

Treatment of Aneurysm: The crosslinkable compositions of the invention can be extruded or molded in the shape of a string or coil, then dehydrated. The resulting dehydrated string or coil can be delivered via catheter to the site of a vascular malformation, such as an aneurysm, for the purpose of vascular occlusion and, ultimately, repair of the malformation. The dehydrated string or coil can be delivered in a compact size and will rehydrate inside the blood vessel, swelling several times in size compared to its dehydrated state, while maintaining its original shape.

Other Uses: As discussed in commonly assigned U.S. Pat. No. 5,752,974, issued May 19, 1998 to Rhee et al., the crosslinkable polymer compositions of the invention can be used to block or fill various lumens and voids in the body of a mammalian subject. The compositions can also be used as biosealants to seal fissures or crevices within a tissue or structure (such as a vessel), or junctures between adjacent tissues or structures, to prevent leakage of blood or other biological fluids.

The compositions can also be used as a large space-filling device for organ displacement in a body cavity during surgical or radiation procedures, for example, to protect the intestines during a planned course of radiation to the pelvis.

The compositions of the invention can also be coated onto the interior surface of a physiological lumen, such as a blood vessel or Fallopian tube, thereby serving as a sealant to prevent restenosis of the lumen following medical treatment, such as, for example, balloon catheterization to remove arterial plaque deposits from the interior surface of a blood vessel, or removal of scar tissue or endometrial tissue from the interior of a Fallopian tube. A thin layer of the reaction mixture is preferably applied to the interior surface of the vessel (for example, via catheter) immediately following mixing of the first and second synthetic polymers. Because the compositions of the invention are not readily degradable in vivo, the potential for restenosis due to degradation of the coating is minimized. The use of crosslinked polymer compositions having a net neutral charge further minimizes the potential for restenosis.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains. All patents, patent applications, patent publications, journal articles and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE 1

Preparation of Crosslinked Compositions from Di-amino PEG 0.15 grams of di-amino PEG (3400 MW, obtained from Shearwater Polymers, Huntsville, Ala.) in 250 $\mu$l of water was mixed with 0.1 g of trifunctionally activated SC-PEG (5000 MW, also obtained from Shearwater Polymers) using syringe-to-syringe mixing. The reaction mixture was extruded onto a petri dish and formed a soft gel at room temperature.

0.15 gram of di-amino PEG in 250 $\mu$l of water was mixed with 0.1 g of tetrafunctionally activated SE-PEG (also from Shearwater Polymers) using syringe-to-syringe mixing. The reaction mixture was extruded onto a petri dish and formed a soft gel at room temperature.

EXAMPLE 2

Preparation of Crosslinked Compositions from Di-amino PEG

The following stock solutions of various di-amino PEGs were prepared:

Ten (10) grams of Jeffamine ED-2001 (obtained from Texaco Chemical Company, Houston, Tex.) was dissolved in 9 ml of water.

Ten (10) grams of Jeffamine ED-4000 (also obtained from Texaco Chemical Company) was dissolved in 9 ml of water.

0.1 grams of di-amino PEG (3400 MW, obtained from Shearwater Polymers, Huntsville, Ala.) was dissolved in 300 $\mu$l of water.

Each of the three di-amino PEG solutions prepared above was mixed with aqueous solutions of triftinctionally activated SC-PEG (TSC-PEG, 5000 MW, also obtained from Shearwater Polymers) as set forth in Table 3, below.

TABLE 3

Preparation of Crosslinked Polymer Compositions

| Di-amino PEG | TSC-PEG + Aqueous Solvent |
|---|---|
| 50 $\mu$l | 0 mg + 50 $\mu$l water |
| 50 $\mu$l | 10 mg + 50 $\mu$l PBS |
| 50 $\mu$l | 10 mg + 100 $\mu$l PBS |
| 250 $\mu$l | 50 mg + 500 $\mu$l PBS |

The solutions of di-amino PEG and TSC-PEG were mixed using syringe-to-syringe mixing. Each of the materials was extruded from the syringe and allowed to set for 1 hour at 37° C. Each of the materials formed a gel. In general, the gels became softer with increasing water content; the gels containing the least amount of aqueous solvent (water or PBS) were firmest.

EXAMPLE 3

Characterization of Crosslinked Multi-amino PEG Compositions

Fifty (50) milligrams of tetra-amino PEG (10,000 MW, obtained from Shearwater Polymers, Huntsville, Ala.) in 0.5 ml PBS was mixed, using syringe-to-syringe mixing, with 50 mg of tetrafunctionally activated SE-PEG ("tetra SE-PEG", 10,000 MW, also obtained from Shearwater Polymers) in 0.5 ml PBS or trifunctionally activated SC-PEG ("tri SC-PEG", 5000 MW, also obtained from Shearwater Polymers) in 0.5 ml PBS.

Syringes containing each of the two mixtures were incubated at 37° C. for approximately 16 hours. Both compositions formed elastic gels. The gels were pushed out of the syringes and sliced into 5-mm thick disks having a diameter of 5 mm, for use in compression and swellability testing, as described below.

Compression force versus displacement for the two gels was measured in the Instron Universal Tester, Model 4202, at a compression rate of 2 mm per minute, using disks of the two gels prepared as described above. Compression force (in Newtons) versus gel displacement (in millimeters) is shown in FIGS. 1 and 2 for gels prepared using the tetra SE-PEG and tri SC-PEG, respectively.

Under compression forces as high as 30–35 Newtons, the gels did not break, but remained elastic.

Disks of each of the two gels, prepared as described above, were weighed and the dimensions (diameter and length) measured. The disks were then immersed in PBS and incubated at 37° C. After 3 days incubation, the disks were removed from the PBS, weighed, and measured. Results of swellability testing are shown in Table 4, below,

TABLE 4

Swellability Testing of Crosslinked Multi-amino PEG Compositions

| Crosslinking Agent | Gel Weight (in grams) | | Dimensions (in mm) diameter/thickness | |
|---|---|---|---|---|
| | Before Swelling | After Swelling | Before Swelling | After Swelling |
| Tetra SE-PEG | 0.116 | 0.310 | 5.0/5.0 | 7.1/8.1 |
| Tri SC-PEG | 0.131 | 0.287 | 5.0/6.0 | 6.4/8.5 |

As shown above, the gels swelled two to three times in weight, as well as swelling an average of about 50% in both diameter and thickness.

EXAMPLE 4

Preparation of Crosslinked Poly(lysine) Compositions

Ten (10) milligrams of poly-L-lysine hydrobromide (8,000 MW, obtained from Peninsula Laboratories, Belmont, Calif.) in 0.1 ml phosphate buffer (0.2M, pH=6.6) was mixed with 10 mg of tetrafunctionally activated SE-PEG (10,000 MW, obtained from Shearwater Polymers, Huntsville, Ala. in 0.1 ml PBS. The composition formed a soft gel almost immediately.

EXAMPLE 5

Preparation and Mechanical Testing of Crosslinked Multi-amino PEG Compositions

Gels comprising tetra-amino PEG (10,000 MW, obtained from Shearwater Polymers, Huntsville, Ala.) and 1–4% (by weight) of tetrafunctionally activated SE-PEG ("tetra SE-PEG", 10,000 MW, also obtained from Shearwater Polymers) were prepared by mixing the tetra-amino PEG (at a concentration of 25 mg/ml in water) with the tetra SE-PEG (in PBS) in a petri dish. The resulting tetra-amino PEG/SE-PEG mixtures were incubated for 16 hours at 37° C.

The mixture containing 1% SE-PEG did not form a gel due to the low SE-PEG concentration. The mixture containing 2% SE-PEG formed a gel at some point during the 16-hour incubation period. The mixtures containing 3 and 4% SE-PEG formed gels within approximately 4–6 minutes of mixing. The gel containing 2% SE-PEG was readily extrudable through a 30-gauge needle; the gel containing 3% SE-PEG could be extruded through a 27-gauge needle.

The effect of elevated temperature on gel formation was evaluated. Gels comprising tetra-amino PEG and 2.5% (by weight) tetra SE-PEG were prepared and incubated at temperatures of 37° C. and 40°–50° C. Elevated temperature was found to have a marked effect on gelation time: the tetra-amino PEG/SE-PEG mixture incubated at 37° C. formed a gel within approximately 20–25 minutes, whereas mixtures incubated at 40°–50° C. formed gels within approximately 5 minutes. Both gels were extrudable through a 27-gauge needle.

The effect of pH on gel formation was evaluated. Gels comprising tetra-amino PEG and 2.5% (by weight) tetra SE-PEG were prepared as set forth in Table 5 below.

TABLE 5

Effect of pH on Gel Formation of Tetra-amino PEG/Tetra SE-PEG Formulations

| pH of Tetra-amino PEG | pH of Tetra SE-PEG | pH of Resulting Mixture | Gelation Time | Gelation Temp. |
|---|---|---|---|---|
| 10 | 4.1 | 6.9 | 10–15 minutes | 45° C. |
| 10 | 7.0 | 7.2 | <5 minutes | 45° C. |

Extrudability through a 27-gauge needle was evaluated for gels comprising tetra-amino PEG and 1–3% (by weight) tetra SE-PEG. The gels were contained within 1-cc syringes. The force required to depress the syringe plunger at a rate of 5 centimeters per minute was measured using the Instron Universal Tester, Model 4202. Results of extrusion testing are presented in Table 6, below.

TABLE 6

Extrusion of Tetra-amino PEG/Tetra SB-PEG Gels Through a 27-Gauge Needle

| Concentration of SE-PEG (by weight) | Extrusion Force (N) |
|---|---|
| 1.5–2% | 10–11 |
| 2–2.5% | 52 |
| 2.5–3% | 88 |

Extrusion forces of 100N or less are considered acceptable for manual injection without the aid of a syringe assist device.

Tensile strength (i.e., elasticity) of 3 mm thick gels comprising tetra-amino PEG and 5,5, and 10% (by weight)

tetra SE-PEG was measured using the Instron Universal Tester, Model 4202. Gels of varying initial lengths were stretched at a rate of 10 millimeters per minute. Length of each gel, strain at failure (change in length as a percentage of the initial length), and force at failure are set forth in Table 7, below.

TABLE 7

Tensile Strength of Tetra-amino PEG/Tetra SE-PEG Gels

| SB-PEG Conc. (wt. %) | Initial Length (cm) | Strain at Failure | Force at Failure (N) |
|---|---|---|---|
| 10 | 1.4 | 139% | 0.4 |
| 10 | 1.9 | 99% | 0.5 |
| 10 | 2.5 | 78% | 0.5 |
| 5 | 1.3 | 111% | 0.2 |
| 5 | 1.3 | 99% | 0.2 |
| 5 | 1.6 | 94% | 0.2 |
| 2.5 | 1.0 | 237% | <0.1 |
| 2.5 | 1.5 | 187% | <0.1 |
| 2.5 | 1.7 | 129% | <0.1 |

Gels containing 5 and 10% tetra SE-PEG approximately doubled in length prior to breaking. Gels containing 2.5% SE-PEG approximately tripled in length prior to breaking, but were considerably weaker (i.e., lower force at failure) than the more highly crosslinked gels.

EXAMPLE 6

Effect of pH on Gel Formation of Tetra-amino PEG/Tetra SE-PEG Formulations

Gel comprising various concentrations of tetra-amino PEG and tetra SE-PEG at pH6, 7, and 8 were prepared in petri dishes. Following mixing of the tetra-amino PEG and tetra SE-PEG, the dishes were tilted repeatedly; the gelation time was considered to be the point at which the formulation ceased to flow. The effect of pH on gelation time of the various tra-amino PEG/tetra SE-PEG formulation at room temperature is shown in Table 8, below.

TABLE 8

Effect of pH on Gel Formation of Tetra-amino PEG/Tetra SE-PEG Formulations

| Tetra-amino PEG Conc. (mg/ml) | Tetra SE-PEG Conc. (mg/ml) | pH | Gelation Time |
|---|---|---|---|
| 20 | 20 | 6 | >90.9 min. |
| 20 | 20 | 7 | 20.0 min. |
| 20 | 20 | 8 | 1.4 min. |
| 50 | 50 | 6 | 24.0 min. |
| 50 | 50 | 7 | 3.5 min. |
| 50 | 50 | 8 | 10.0 sec. |
| 100 | 100 | 6 | 9.0 min. |
| 100 | 100 | 7 | 47.0 sec. |
| 100 | 100 | 8 | 10.0 sec. |
| 200 | 200 | 6 | 2.0 min. |
| 200 | 200 | 7 | 9.0 sec. |
| 200 | 200 | 8 | 5.0 sec. |

The time required for gel formation decreased with increasing pH and increasing tri-amino PEG and tetra SE-PEG concentrations.

EXAMPLE 7

Culturing of Cells in Crosslinked Multi-amino PEG Matrix

Thirty (30) milligrams of tetra-amino PEG (10,000 MW, obtained from Shearwater Polymers, Huntsville, Ala.) was dissolved in 0.6 ml PBS, then sterile filtered. Thirty (30) milligrams of tetrafunctionally activated SE-PEG ("tetra SE-PEG", 10,000 MW, also obtained from Shearwater Polymers) was dissolved in 0.6 of PBS, then sterile filtered.

The solutions of tetra-amino PEG and tetra SE-PEG were mixed together with a pellet containing human skin fibroblast ("HSF") cells (CRL #1885, passage 4, obtained from American Tissue Type Culture Collection, Rockville, Md.). Two hundred fifty (250) microliters of the resulting cell-containing tetra-amino PEG/tetra SE-PEG (PEG-PEG) solution was dispensed into each of two wells on a 48-well culture plate and allowed to gel for approximately 5 minutes at room temperature. One (1) milliliter of Dulbecco Modified Eagle's Media (supplemented with 10% fetal bovine serum, L-glutamine, penicillin-streptomycin, and non-essential amino acids) was added to each of the two wells. The concentration of cells was approximately $3 \times 10^5$ cells per milliliter of tetra-amino PEG/tetra SE-PEG solution, or $7.5 \times 10^5$ cells per well.

To prepare a control, a pellet of HSF cells were suspended in 1.2 ml of complete media. Two hundred fifty (250) microliters of the control mixture was dispensed into each of three wells on the same 48-well culture plate as used above. Each well was estimated to contain approximately $7.5 \times 10^5$ cells. Each well was given fresh media every other day.

Initially, the cell-containing tetra-amino PEG/tetra SE-PEG gels were clear and the cells were found to be densely populated and spheroidal in morphology, indicating that there was little adhesion between the cells and the PEG/PEG gel (the cells would normally assume a flattened, spindle-shaped morphology when adhered to a substrate, such as to the treated plastic of the tissue culture plates). After three 3 days incubation at 37° C., the media in the wells containing the PEG/PEG gels was found to have lightened in color (Dulbecco Modified Eagle's Media is normally red in color), indicating a pH change in the media. This indicated that the cells were alive and feeding. At 7 days incubation at 37° C., the cells were still spheroidal in morphology (indicating lack of adhesion to the gel) and the media had lightened even further, indicating that the cells were still viable and continued to feed.

On day 7, the contents of each well were placed in a 10% formalin solution for histological evaluation. According to histological evaluation, an estimated 75% of the cells in the wells containing the PEG/PEG gels appeared to be alive, but did not appear to be reproducing.

The results of the experiment indicate that HSF cells are viable in the tetra-amino PEG/tetra SE-PEG crosslinked gels, but did not seem to adhere to the gel and did not appear to reproduce while entrapped within the gel matrix. As described above, adherence or non-adherence of cells to a substrate material can influence the cells' morphology. In certain types of cells, cellular morphology can, in turn, influence certain cellular functions. Therefore, non-adherence of the cells to the PEG-PEG gel matrix may be an advantage in the delivery of particular cell types whose function is influenced by cell morphology. For example, the ability of cartilage cells to produce extracellular matrix materials is influenced by cellular morphology: when the cells are in the flattened, spindle-shaped configuration, the cells are in reproductive mode; when the cells are in the spheroidal configuration, reproduction stops, and the cells begin to produce extracellular matrix components.

Because the PEG-PEG gels are not readily degraded in vivo, the gels may be particularly useful in cell delivery applications where it is desirable that the cells remain entrapped within the matrix for extended periods of time.

EXAMPLE 8

Preparation of a Penta-ervthritol-Based Tissue Sealant Composition

Penta-erythritol tetrakis (3-mercapto-proprionate), mol. wt. 489 ("PESH-P," obtained from Aldrich Chemical Company, Milwaukee, Wis.), 1.08 g, and penta-erythritol tetra-acrylate, mol. wt. 352 ("PETA," also obtained from Aldrich), 1.0 g, are mixed together in the presence of 5 to 10 μg of a polyoxypropylene triamine ("T403," Jeffamine, Texaco Chemical Co., Houston, Tex.), which serves as a base. All reactive species are liquids. The PESH-P and PETA are not miscible in water. Accordingly, PETA is warmed to about 40° C. to form a liquid prior to mixing with PESH-P and T403. Within 1 to 5 minutes after mixing, depending on the level of T403, gelation begins. The gel is allowed to cure for several hours, followed by one hour of hydration at 37° C. Thereafter, the tensile strength of the gel is 0.88+/−0.3 MPa. When such gels are left in physiological saline, pH 6.7, they are stable for more than 40 days, and only swell about 20%. Burst strength data shows only moderate adhesion to hide grindate. This would be expected, since there is no chemical bonding of sulfhydryl or acrylate to protein using PETA-P/PESH mixtures. In three tests of burst strength, burst pressures of 20–40 mm Hg were observed.

EXAMPLE 9

Tensile Strength Evaluation

Materials and Methods: Penta-erythritol polyethylene glycol ether tetrathiol, 10,000 mol. wt. ("COH206"), penta-erythritol polyethylene glycol ether tetra succinimidyl-glutarate, 10,000 mol. wt. ("COH102"), and penta-erythritol polyethylene glycol ether tetra amino, 10,000 mol. wt. ("COH204"), were purchased from Shearwater Polymers, Inc. (Huntsville, Ala.) Cyanoacrylate, "Superglue," was purchased over the counter. Gelatin, 70–100 Bloom, was purchased from Sigma (Saint Louis, Mo.) Sulfoethylene glycol bis succinimidyl succinate ("S-EGS"), dimethyl suberimidate ("DMS"), and dissuccinimidyl glutarate ("DSG") were purchased from Pierce Chemical Company, Rockford, Ill. Polyethylene glycol ("PEG") 200 mol. wt. di-acrylate ("PEG-di-acrylate"); PEG, 1,000 mol. wt. di-methacrylate ("PEG-di-methacrylate"); and 2-hydroxy-ethyl methacrylate ("HEMA") were purchased from Polysciences, Inc., Warrington, Pa. Polypropylene ("PPO"), 540 mol. wt. di-acrylate ("PPO-di-acrylate"); PPO, 230 mol. wt. bis-2-aminopropyl ether ("PPO-di-amino 230"); PPO, 2,000 mol. wt. bis-2-aminopropyl ether ("PPO-di-amino 2,000"); poly-tetrahydrofuran bis (3-aminopropyl) ("PTMO"), 350 mol. wt. ("PTMO 350"); PTMO, 1,100 mol. wt. ("PTMO 1,100"); PESH-P, 489 mol. wt.; PETA, 352 mol. wt.; and potassium meta-bisulfite were purchased from Aldrich Chemical Company, Milwaukee, Wis. Ammonium persulfate was purchased from Biorad, Inc., Richmond Calif. Methylated collagen was prepared from purified bovine corium collagen, following a method modified from U.S. Pat No. 4,164,559 (see Example 11).

Gel Preparation:

a. COH102/COH206: 100 mg COH102 were dissolved in 400 μl 0.5 mM sodium phosphate, pH 6.0. 100 mg COH206 were dissolved in 400 μl 300 mM sodium phosphate, pH 7.5. The two solutions were mixed in a beaker and poured into a mold of approximately 8×0.5× 0.5 cm. Gelation occurred in 2–3 minutes. The sample was left at room temperature until dry. The dried matrix was removed from the mold, and hydrated at 37° C. for one hour prior to the tensile strength test.

b. COH102/COH204: The sample was prepared as described in a., except that the COR204 was substituted for COR206.

c. PETA/PESH-P: The sample was prepared as described in Example 8.

d. Gelatin gels: 20% gelatin in sodium phosphate/sodium carbonate buffer, pH 9.6, was mixed with different compounds as indicated below and described in a., assuming 10–20 moles of active amino per mole of gelatin, and using stoichiometric levels of the other compound.

e. COH102/PPO-di-amino 2,000/PEG-di-acrylate: 615 mg COH102 was dissolved in 923 μl ethanol, and mixed with 246 μl PPO-di-amino 2,000 and 246 μl PEG-di-acrylate as described in (a).

f. PETA/PPO-di-amino 230/PPO-di-amino 2,000: 500 μl PETA, 630 μl PPO-di-amino 230 and 150 μl PPO-di-amino 2,000 are mixed together as described in a.

g. COH102/PTMO: The gel was prepared as described in e, with PTMO 1,100 substituted for the PPO-di-amino 2,000.

h. Cyanoacrylate: The glue was extruded onto water and immediately hardened.

i. HEMA: 1.3 ml HEMA and 64 μl PEG-di-acrylate were dissolved in 600 μl of 150 mM sodium phosphate buffer, pH 7.4, and mixed with 40 mg ammonium persulfate in 100 μl water. The mixture was heated to 60–80° C. for 4 hours.

j. COH 102/COH206/methylated collagen: 25 mg methylated collagen, 100 mg COH102, and 100 mg COH206 were dissolved in 1 ml 0.5 mM sodium phosphate, pH 6.

Tensile Strength Measurements:

The ends of the dried gels were secured, and then the central regions of all samples were rehydrated for approximately 1 hour in physiological saline buffer, pH 6.7 at 37° C. prior to the test. Then, the matrices were extended to the point of breakage in an Instron Model 4202 test apparatus (Instron, Inc., Canton, Mass.) that was fitted with a 100 N load cell. The peak load was recorded and converted into ultimate stress using the measured cross-section of the sample at the break point. Data were also plotted as stress v. strain, using strain=$\Delta L/L_0$, where $\Delta L$ is the extension, and $L_0$ is the original sample length. Tensile strength measurements were as follows:

| Material | Tensile Strength (N/cm$^2$) |
|---|---|
| HEMA | >393 |
| Cyanoacrylate | 385 |
| PETA/PESH-P | 78 (n = 10) |
| PETA/PTMO-di-amino 350/1,100 | 26 (n = 2) |
| PETA/PTMO-di-amino 1,100 | 34 |
| PETA/PPO-di-amino 230/2,000 | 36 (n = 2) |
| PESH-P/PPO-di-acrylate | 20 |
| COH102/COH206/methylated collagen | 37 (n = 3) |
| COH102/PPO-di-amino 2,000/PEG-di-acrylate 200 | 10 (n = 2) |
| COH102/PTMO-di-amino | 4 (n = 2) |
| COH102/T403 | 5 |

-continued

| Material | Tensile Strength (N/cm²) |
|---|---|
| COH206/PEG-di-acrylate | 8 |
| COH/206/PEG-di-methacrylate/PEG-diacrylate | 4 |
| COH206/PEG-di-methacrylate | 26 |
| Gelatin/DMS | 6 |
| Gelatin/S-EGS | 6 (n = 2) |
| Gelatin/PETA | 5 |
| Gelatin/DSS/T403 | 3 |
| COH102/COH206 20% | 5 (n = 4) |
| COH102/COH206 10% | 10 |

EXAMPLE 10

High-strength adhesives based on COH102 and COH206 and a comparison with adhesives prepared from PETA, PESH-P (penta-erythritol tetrakis (3-mercapto-proprionate)), and GLYC-20HS:

Summary:

Several types of gels were investigated as potential suture replacement formulations. Gels based on penta-erythritol derivatives exhibited high cohesive, but poor adhesive strength. Gels based on a 3-armed succinimidyl glycerol-PEG exhibited low cohesive strength, but good adhesive strength. Gels based on 60% aqueous (w/v) COH102/COH206, to which various fibrous materials were added, such as fibrous insoluble collagen, polyglycolide sutures and glass wool, exhibited both good cohesive and adhesive strengths.

High strength medical adhesives are of interest as suture-replacements in closure of surgical incisions. In particular, gels formed from PETA and PESH-P were shown to have tensile strengths about 1OX greater than those formed from 20% (w/v) solutions of COH102 and COH206. When PETA-PESH-P gels were supplemented with fibrous or particulate polymers, gels with even higher tensile strengths were observed.

This experiment describes the adhesive properties of PETA/PESH-P and related gels, as well as both adhesive and tensile properties of a formulation of COH102 and COH206 at 60% (w/v), to which collagen and other polymers are added. Also described are properties of gels formed from a 3-arm glycerol succinimide (NOF Corp., Japan) and the above reagents.

Materials and Methods:

PETA, PESH-P, and penta-erythritol tetrakis (3 mercaptoacetate) (PESH-A), polyethylene, surface activated 180□particle size, and polybutadiene, epoxy functionalized, epoxy E. W. 260, were purchased from Aldrich Chemical Co., Milwaukee, Wis. GLYC-20HS (poly-oxyethylene glyceryl ether) succinimidyl succinate 2600 mw), DEPA-10H (poly-oxyethylene bis-amine 1040 mw) were obtained from NOF Corporation, Japan. COH102 and COH206 were reagent grade from Shearwater Polymers, Huntsville, Ala., Polyethylene-co-acrylate-succinimidate (PE-AC-S) was synthesized from: a polyethylene-co-acrylate (approx. mol. wt. 400K with 5% acrylate) purchased from Aldrich Chemical Company, Milwaukee, Wis. Kensey-Nash insoluble collagen (Semed F) was purchased from Kensey-Nash Corporation, Exton, Pennsylvania. Collagen Matrix, Inc, Franklin Lakes, N.J., supplied a second type of insoluble collagen. Prolene 7–0 sutures were manufactured by Ethicon Corporation. Coarse fibered collagen sheets were cut from the same coarse fibered bovine corium collagen as that used for the burst test as described in Prior, J. J., Wallace, D. G., Harner, A., and Powers, N., "A sprayable hemostat containing fibrillar collagen, bovine thrombin, and autologous plasma", Ann. Thor. Surg. 68, 479–485 (1999). These collagen sheets served as a tissue model for further studies. Smaller fiber collagen was prepared from re-precipitated pepsin-digested bovine corium collagen manufactured by Collagen Aesthetics, Inc., Palo Alto, Calif. Glass wool was purchased from VWR Corporation. Poly-glycolide sutures, non-coated ("Dexon S") were from Davis and Geck.

Gel formation for tensile strength measurements is described above in Example 1. For burst tests, the apparatus used is described in Wallace et al., supra. Approximately 1 ml of total formula was sprayed or spread by spatula onto the coarse fibered collagen sheet substrate and allowed to set. Water pressure was applied after the formulation had reached the texture of a relatively firm rubbery solid (no longer tacky), and the pressure to rupture the seal was recorded as mm Hg.

60% gels of COH102 and COH206 were prepared as follows: COH102 was dissolved at 60% (w/v) in S-buffer (0.5 mM sodium phosphate, pH 6.0) and COH206 was dissolved also at 60% in 300 mM sodium phosphate at pH 7.5 or 8.9; or in 117 mM sodium phosphate, 183 mM sodium carbonate, pH 9.6 ("PC buffer"). In some cases the above ratio of phosphate and carbonate were altered to give pH 9.44 for a faster set time. The pH used in each case was determined by the rate of gelation desired. Various additives were added to such a base formulation; e.g., Kensey-Nash and smaller fiber size collagen was added at 28 mg/ml of final gel; glass wool was added at 25 mg/ml; and polyglycolide sutures, at 40 mg/ml.

Results and Discussion:

The results are discussed below and shown in Tables 9, 10 and 11 that follow. A tensile strength of >60 N/cm² is considered to be "strong". A burst strength of >50 mm Hg is considered to be "good adhesion".

Gels of PETA and PESH-P had shown good tensile strengths (Example 8). However, when they were tested for adhesion to a hydrated simulated tissue (coarse fibered collagen sheets) in the burst test, they exhibited poor adhesion (<50 mm Hg burst pressure). As shown below in Table 9, the formulation was then modified to contain water soluble GLYC-20HS and DEPA-10H, or the pair COH 102 and COH206 (which alone in aqueous media gave good adhesion to the collagen sheets). These materials had good tensile strength (manual evaluation), but again poor adhesion to the collagen sheets. The gel formed from GLYC-20HS and DEPA-10H also had poor adhesion when no water was present in the formula. A different result may be observed when these reagents are dissolved in aqueous buffers, since they are water soluble.

However, when GLYC-20HS was the major component by mass, the gels were weak but exhibited good adhesion in the burst test. Using these particular combinations of components, it appeared that one could achieve either high tensile strength or high adhesive bonding, but not both.

TABLE 9

Tensile Strength and Burst Strength of Gels Prepared with NOF 3-arm Glycerol Succnimide

| Material | Tensile Strength (N/cm²) | Burst Strength (mmHg) |
|---|---|---|
| PETA 500 mg<br>PESH-P 540 μl<br>T403 5 μl | >60 | 23 |

TABLE 9-continued

Tensile Strength and Burst Strength of Gels Prepared with NOF 3-arm Glycerol Succnimide

| Material | Tensile Strength (N/cm$^2$) | Burst Strength (mmHg) |
|---|---|---|
| GLYC-20HS 50 mg<br>PETA 500 mg<br>PESHP 540 μl<br>DEPA-10H 9 mg | >60 | 14.5 |
| PESH-A 216 μl<br>PETA 240 mg<br>GLYC-20HS 40 mg | >60 | 11 |
| PETA 400 mg<br>COH102 100 mg<br>PESH-P 440 μl<br>COH206 100 mg<br>DEPA-10H 8 mg | >60 | 15 |
| GLYC-20HS 640 mg<br>DEPA-10H mg | — | 25 |
| GLYC-20HS 400 mg<br>PESH-A 36 μl<br>T403 10 μl | <30 | >120 |
| GLYC-20HS 400 mg<br>PETA 50 mg<br>PESH-A 72 μl<br>T403 20 μl | <30 | 166, 194 |
| GLYC-20HS 200 mg<br>T403 19 μl<br>PESH-P 18 μl | <30 | 55 |

The ability of a succinimidyl-derivatized polyethylene (PE-AC-S) to act as an effective tensile strength enhancer for PETA-PESH-P gels and for COH102/206 gels was also assessed (Table 10). This material did not increase the tensile strength of these gels, perhaps because it was not an extended filament, i.e. its aspect ratio was not high enough.

TABLE 10

Polyethylene-co-acrylate-succinimide ("PE-AC-S") as a Tensile Strength Enhancer

| Material | Tensile Strength (N/cm$^2$) |
|---|---|
| PETA 400 mg<br>PESH-P 432 μl<br>T403 8 μl<br>PE-AC-S 20 mg | 80<br>(same as control with no PE-AC-S) |
| COH102<br>COH206 (60%) +<br>KN collagen (28 mg/ml) +<br>PE-AC-S (40 mg/ml) | 38<br>(weaker than control with no PE-AC-S) |

Table 11 Ialso summarizes results with COH102 and COH206 plus Kensey-Nash fibrillar collagen, which exhibited an enhanced tensile strength over 20% and 60% (w/v) gels of COH 102/206 alone. Furthermore, the COH 102/COH206/collagen formulation possessed good adhesive bonding to the collagen sheets. Other additives, such as hide grindate and Prolene 7-0 sutures also enhanced the gel strength over controls. Some fillers, such as small fiber collagen, polyethylene, and polybutadiene, did not exhibit tensile strength enhancing properties. Finally, some fillers or combinations thereof, such as glass wool and insoluble collagen plus poly-glycolide sutures, exhibited a significant enhancement of tensile strength, exceeding that seen with cyanoacrylate (385 N/cm$^2$) (Example 1). Limnited burst strength data were collected, but they confirm that all these COH102/206 (60%) formulations are highly adhesive to collagen surfaces, and thus would be expected to adhere to tissues as well.

As shown in Table 11, the P-HEMA hydrogel is described in Santin, M., et al., "Synthesis and characterization of a new interpenetrated poly (2-hydroxyethylmethacrylate)-gelatin composite polymer", Biomaterials 17, 1459–1467; and the gelatin-PEG-di-acrylate is described in Nakayama, Y., and Matsuda, T., "Photocurable surgical tissue adhesive glues composed of photoreactive gelatin and poly(ethylene glycol) diacrylate", J. Biomed. Biomat. Res. (Appl. Biomater.) 48, 511–521 (1999).

TABLE 11

Tensile Strength and Burst Strength Tests

| Material | Tensile Strength (N/cm$^2$) | Burst Strength (mm Hg) |
|---|---|---|
| COH102/206<br>20% GEL | 2–12 | 100–200 |
| GELATIN-<br>PEG-DI-<br>ACRYLATE** | 3 | |
| pHEMA<br>HYDROGEL* | 5–16 | 151 ± 34 |
| PETA-<br>PESH-P | 50–170 | 14, 23 |
| PETA-<br>PESH-P +<br>KN collagen | 140–200 | |
| COH102/206<br>(60%) + KN collagen | 123 ± 39<br>(n = 7) | 268,216 |
| COH102/206<br>(60%) + KN collagen +<br>7-0 Prolene sutures | 180 | |
| COH102/206<br>(60%) + hide grindate | 197, 78<br>94 | |
| COH102/206<br>(60%) no filler | 27 | |
| COH102/206<br>(60%) + Small fiber collagen | 27 | |
| COH102/206<br>(60%) + 7-0 Prolene sutures coated | 58 | |
| COH102/206<br>(60%) + polyethylene | 14 | |
| COH102/206<br>(60%) + polyethylene +<br>poly-butadiene | 58, 30<br>28, 21 | |
| COH102/206<br>(60%) + glass wool | 745<br>161 | 156 |
| COH102/206<br>(60%) + KN collagen +<br>Dexon S sutures | 531 | |
| COH102/206<br>(60%) + Collagen<br>Matrix collagen +<br>Dexon S sutures | 718 | 376 |

Figure 15:
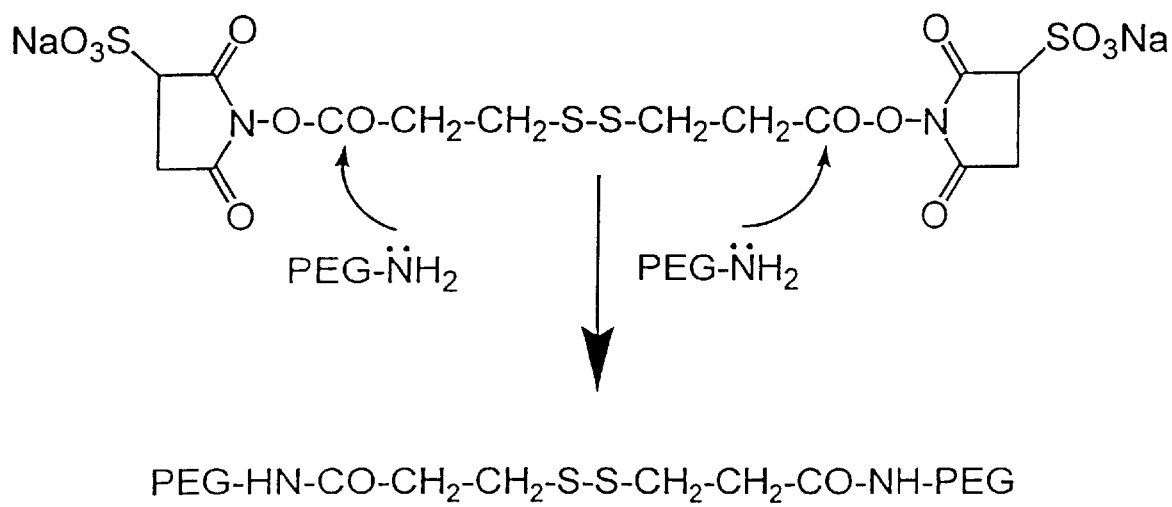
Figure 16:
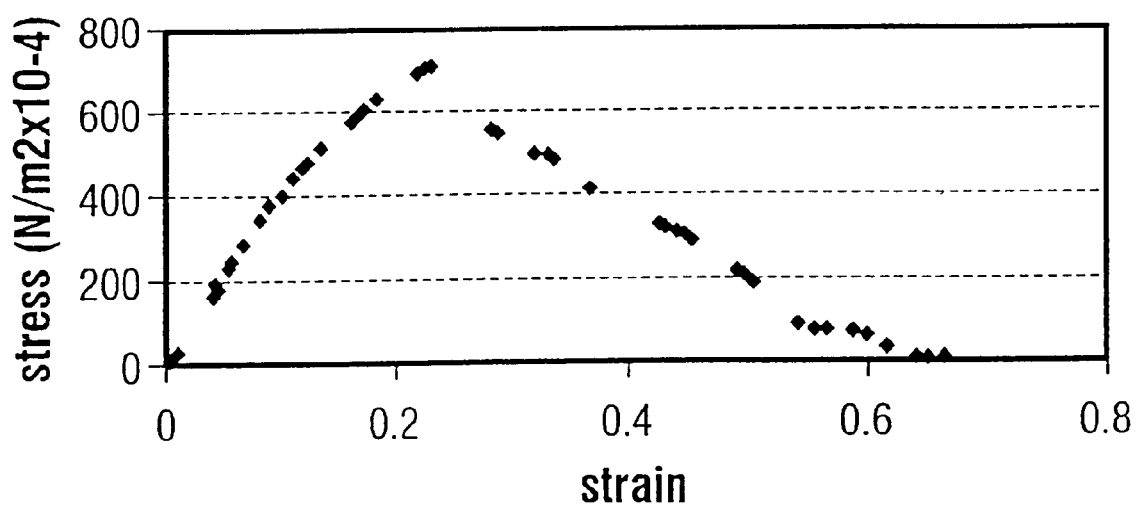

FIG. 15 depicts the tensile test of COH102/206 (60%) plus 28 mg/ml Collagen Matrix collagen plus 40 mg/ml cut pieces of Dexon S uncoated polyglycolide sutures (4-0). The measured tensile strength was higher than 700 N/cm$^2$, and the measurement was interrupted when the sample began slipping out of the testing device (downward slope.)

EXAMPLE 11

COH102/206/methylated Collagen Plus the Fibrous Fillers Glass Wool or Vicryl

Materials:

a. Methylated Collagen

Methylated collagen was prepared by a modification of the procedure of Miyata et al, U.S. Pat. No. 4,164,559. A dispersion (3% w/v) of bovine pepsinized reconstituted collagen in 0.02M sodium phosphate, 0.13M NaCl, pH 7.2 (prepared by the method of McPherson et al., Collagen Rel. Res. 5, 119–135, 1985) was extruded onto a glass surface in a thin layer and dried at room temperature. Methanolic HCl was prepared by adding 104 g of anhydrous sodium sulfate and 10.7 ml of conc. HCl to 1300 ml of anhydrous methanol and allowed to stand tightly capped for 2 days. The dried collagen was cut into 1×5 cm strips and added to the methanolic HCl (200 ml methanolic HCl: 1 g dry collagen) in a sealed vessel and gently shaken at 20° C. for 3 days. The methanolic HCl was carefully decanted off and the collagen was filtered on a sintered glass funnel to remove traces of methanol. Complete methanol removal was completed under vacuum overnight. The methylated collagen was re-solubilized in distilled water, and the pH was adjusted to 4 to 6. The amount of water was calculated to achieve a final protein concentration of about 31 mg/ml. Samples of solubilized methylated collagen at lower protein concentrations were re-concentrated by brief lyophilization to remove water. Solubilized methylated collagen was a completely transparent material, free of fibers or opalescence, having a viscous, gel-like consistency. Preparations which still contained hazy or insoluble components (due to incomplete methylation of the collagen) performed poorly in adhesive formulations, producing gels that swelled too much and exhibited poor bond strength.

b. Adhesive Without Filler

For 0.5 ml of adhesive, 50 mg of dry powdered COH102 (4-armed tetra-glutaryl-succinimidyl polyethylene glycol, 10K) and 50 mg of dry powdered COH206 (4-armed tetra-thiol polyethylene glycol, 10K) were mixed with 400 mg of methylated collagen at 31 mg protein/ml, pH 4. Both PEG components dissolved in the aqueous solution of collagen, yielding a transparent, viscous fluid. The solution was spread on the tissue site with a spatula, it flowed very little under the force of gravity. To cure the adhesive, 20–50 µl of a buffer (either 134 mM sodium phosphate, 166 mM sodium carbonate, pH 8.9; or PC buffer, pH 9.6) was added to the surface. The buffer did not dilute the gel, but slowly soaked in. In 3–5 min, the surface of the gel was noticeably hardened.

For studies of bond strength under hydrated conditions, the gel plus substrate was allowed to cure for 20 min on the bench, then immersed in 50 mM sodium phosphate, 130 mM sodium chloride, pH 6.7, at 37 deg. C. for 2 hours or longer. Testing of bond strength was performed on a tensile apparatus.

c. Adhesive With Filler

Vicryl is a copolymer of glycolic acid and lactic acid (90:10) sold as an implantable mesh by Ethicon Corporation (Polyglactin 910; Sommerville, N.J.).

To the methylated collagen was added 19 mg of Vicryl threads 1–2 cm long which had been unraveled from implantable Vicryl mesh. In some cases, Vicryl fibers as short as 0.3 cm were also used. The threads and the viscous gel were blended, and then the PEG components were added, as described above. Application to the tissue site and curing were as above. Other fillers and their respective amounts added to 0.5 ml of adhesive were: glass wool, 9 mg; fibrous collagen (Semed F collagen, Kensey-Nash Corporation) 8 mg; Dexon S (poly glycolide lactide sutures, "4-0"), 10 pieces 1 cm long, elastin fibers (bovine neck ligament, 0.25 to 10 mm, Elastin Products Co., Inc, Owensville, Mo.), 40 mg; stainless steel fibers (Bekaert Fibre Technologies, Marietta, Ga.), 14–28 mg (Fibers were washed with water or 1N HCl to remove a polyvinylalcohol coating); polylactide/glycolide microparticles, prepared from polylactide/glycolide (65:35, 40–75,000 mol. wt., Aldrich Chemical Co., microparticles 2–4 µm in diameter prepared by the method of Zheng, J., and Hornsby, P. J., Biotechnol. Progr. 15, 763–767 (1999), 25 mg.

d. Adhesive with Methylated Collagen Replaced by Another Agent

Various long-chain molecules were tested, such as hyaluronic acid (rooster comb, Sigma Chemical Co., St. Louis, Mo.), chitosan (Sigma), and polylysine (Sigma). For hyaluronic acid, the formula was: COH102, 50 mg, COH206, 50 mg, Vicryl, 14 mg, and 400 µl of hyaluronic acid, 2% (w/v) in water, pH adjusted to 4; for chitosan, the same formula, with 400 µl of 1% chitosan (w/v) in water, pH 4–5. For polylysine, COH 102, 40 mg, COH206, 30 mg, dissolved together in 50 µl water; polylysine hydrobromide, 330K, 40 mg dissolved in 60 µl water; the two solutions were mixed together, and 7 mg Vicryl fibrils were added. In addition, polylactide/glycolide particles, prepared as above, were tested as a replacement for methylated collagen; 16.5 mg of particles were suspended in 300 µl of water and mixed with 50 mg COH102, 50 mg COH206, and 14 mg Vicryl. All gels were cured with pH 9.6 buffer overlay, as described above.

e. Adhesive Without Filler and Without Methylated Collagen

COH102 was dissolved in water at 20% (w/v), COH206 was dissolved at 20% in pH 8.9 buffer. The two solutions were rapidly mixed and extruded onto the site. Gelation occurred in ~40 sec.

Figure 17A:
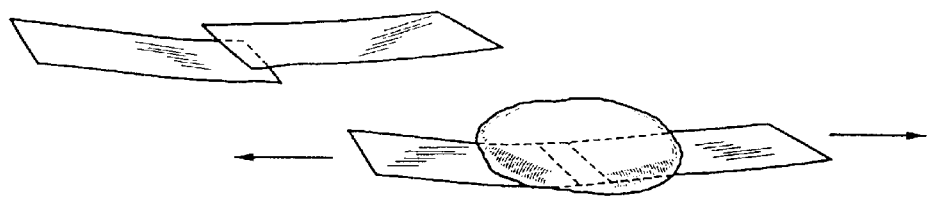
Figure 17B:
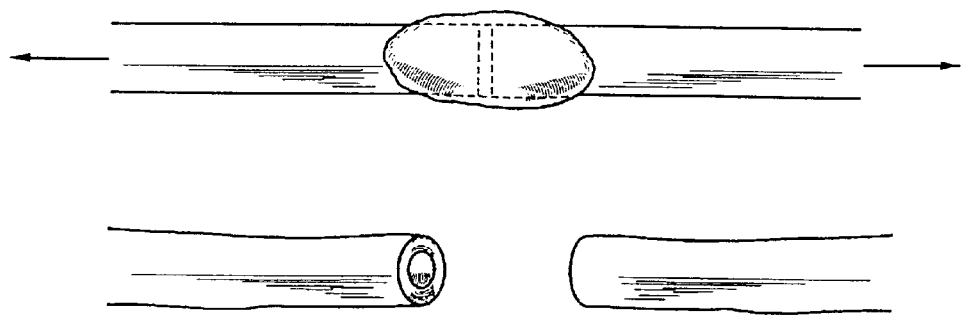
Figure 17C:
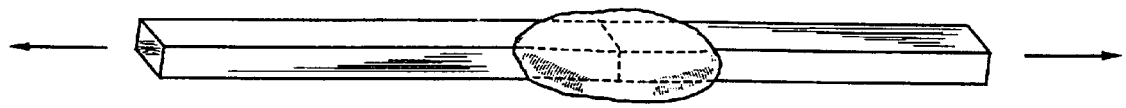

Mechanical Tests:

Bond strength of the adhesive formulations were applied to three types of tissue or tissue surrogates depicted in FIG. 17. Collagen membranes (FIG. 17a, sausage casings, The SausageMaker, Inc., Buffalo, N.Y.) were washed with isopropyl alcohol and water to remove lipid and salt impurities, and dried. Bonding of membranes with a 1–3 mm overlap and a 1 cm width was performed by spreading the adhesive over the top of the sheets. Adhesive was allowed to cure 20 min on the bench and then immersed for 30 min to 2 hours at 37° C. before pulling apart in an Instron model 4202 test apparatus (Canton, Mass.), using a 100N load cell. Bonding of porcine carotid arteries (10b, Pelfreeze, Rogers, Ark.) was also performed in an end-to-end geometry. Cut carotid artery segments were abutted (4–6 mm diameter) and spread with adhesive; no stay sutures were applied. Incubation and testing were the same as described for the collagen membranes.

For bonding of cowhide strips (10c), de-haired calf skin pieces were purchased from Spear Products, Inc., Quakertown, Pa. Pieces were nearly uniform in thickness, 2–3 mm. Strips 0.4 cm wide were cut from the hide pieces, using a single-edged razor blade. Cut strips were abutted end to end and bonded by spreading 0.25 ml of "CT003" adhesive or a few drops of cyanoacrylate. Incubation and testing were the same as described for the collagen membranes. Table 12 below shows that COH 102/COH206/ methylated collagen, when filled with glass wool (Formula c), was superior in bonding strength to unfilled Formulas a and b when tested on collagen membranes. In fact, the bonding strength was comparable to that obtained with a commercial cyanoacrylate adhesive (Table 9). A medical grade cyanoacrylate (Dermabond) formed even stronger bonds with collagen membranes (5.2±1.9 N force for 7 determinations).

TABLE 12

Bonding Performance with and without Methylated Collagen and a Fibrous Filler

| Formula | Bond Strength (N Force) | n |
|---|---|---|
| COH102/206 (20%) | 1.6 ± 1.1 | 3 |
| COH102/206/methylated collagen | 1.7 ± 1.0 | 4 |
| COH102/206/methylated collagen/glass wool | >2.8 ± 0.6* | 6 |

*Collagen membrane tore, but sealant bond was still intact.

TABLE 13

Bond Strength of Cyanoacrylate (Krazy Glue, Elmer's Products) on Three Different Tissue Substrates

| Substrate | Bond Strength (N Force) |
|---|---|
| Cowhide strips | 10.9, 16.2 |
| Porcine carotid artery | 2.0, 3.8 |
| Collagen membrane | 3.0 ± 1.0 (n = 5) |

Table 14 below presents data on the addition of a different filler, Vicryl threads, to the COH102/206/methylated collagen. With substrates such as cowhide or carotid artery, the substrate did not tear, and the bond strength values were representative for the strength of the adhesive bond itself. Typically these bonds failed adhesively, that is, the tensile strength of the adhesive gel itself remained intact and was not the limiting factor. The bond strengths observed in Saline at 37° C. again were comparable to those seen with cyanoacrylate for bonding the same set of tissue substrates (Table 13).

TABLE 14

Bond Strength of COH102/206/methylated Collagen with Vicryl Threads as a Filler on Three Different Tissue Substrates

| Incubation Time (Hrs.) | Bond Strength (N Force) | Substrate* |
|---|---|---|
| 2 | 6.6, 5.6 | Cowhide |
| 17 | 6.3, 5.5 | Cowhide |
| 2 | 4.3, 2.2, 2.8, 5.1 | Porcine Carotid Artery |
| 2 | >5.9, 3.9 | Collagen Membrane |

*cowhide strips, 0.5 cm wide, porcine carotid artery, 0.3–0.5 cm diameter, collagen membrane: sausage casing, 0.2 mm thick, 1 cm width.

Effect of Different Fillers:

Table 15 presents results of various filler materials. Testing was performed on cowhide strips, immersed for 2 hours in saline at 37° C. It appeared that filamentous materials were more effective than spheroidal particles. Bonding of the filler to the gel is very important for improvement of strength. Collagen-polyethylene glycol filaments were waxy and did not adhere to the gel; thus, despite their high aspect ratios, they were not effective fillers.

TABLE 15

Effect of Different Fillers on Bond Strength of COH102/206/methylated Collagen

| Material | Bond Strength (N Force) |
|---|---|
| Vicryl | 4.7, 7.4 |
| Vicryl, washed with ethanol | 7.2, 7.8 |
| Vicryl, treated with ethanol, then washed with 30% hydrogen peroxide | 8.3, 9.1 |
| Surgical silk sutures 1–2 cm long, 30–50 u diameter | 2.5, 3.8 |
| Surgical silk sutures, unraveled to finer threads, washed with chloroform | 5.0, 6.5 |
| Fibrous collagen (Semed F, Kensy-Nash) adjusted to pH 4; 0.5 to 1 mm long, ~50 u diameter | 1.3, 2.8 |
| Gelatin particles, cross-linked by heat, ~100 u diameter, polygonal | 0.6, 0.8 |
| Hydroxyapatite particles, 0.5 to 1 mm diam. polygonal | 0.7 |
| Collagen-polyethylene glycol conjugate filament ~50 u diameter, 1 cm long | 0.8, 1.7 |
| Stainless steel fibers 8 u diameter, 4 mm long | 4.8, 6.9 |
| Elastin fibers 0.25 to 10 mm long | 3.9, 4.0 |
| Polylactide/glycolide articles, 2–4 u diameter | 1.1, 1.1 |

Effect of Replacing Methylated Collagen with Other Polymeric Molecules:

Table 16 shows that none of the tested materials gave bond strengths comparable to the formula containing methylated collagen

TABLE 16

Replacement of Methylated Collagen by Other Molecules

| Material | Bond Strength (N Force) |
|---|---|
| Hyaluronic acid | 1.2, 1.3 |
| Chitosan | 2.1, 1.7 |
| Polylysine | 2.0 |
| Polylactide/glycolide particles, 2–4 | 0.6, 1.1 |

Figure 18:
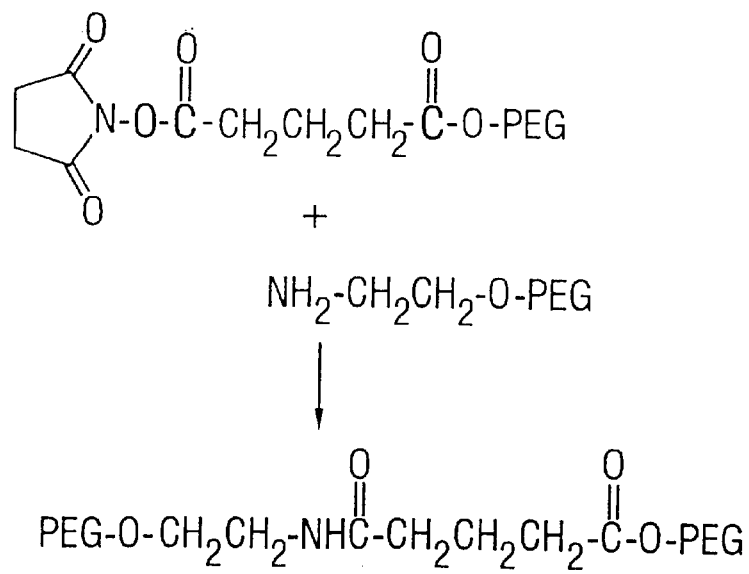

Effect of Cross-Linking Bond:

Table 17 below shows that when the gel was formed from other types of cross-linking reactions, the adhesion and bond strength was affected when tested on cowhides after incubation at 37° C. Material 1 was formed from COH206 and hydrogen peroxide, which oxidizes adjacent sulfhydryl groups to a disulfide bond. A gel forms rapidly, and the gel can be supplemented with methylated collagen and Vicryl; however, after several hours in saline buffer, the gel becomes very weak; the Vicryl fibers are easily pulled out. Material 2 utilized the reaction of sulfhydryl groups from COH206 with the double bond of a 4-arm vinyl sulfone derivative of PEG (10K, Shearwater Polymers; FIG. 10). The presumed reaction, a Michael-type addition, formed a thio-ether bond. Such gels had adequate tensile strength but poor adhesion to the cowhide after incubation in saline. Materials 3 and 4 contained COH204 (4-armed, tetra-functional amino PEG, 10K, Shearwater Polymers); the amino functionality presumably reacted with the succinimidyl ester of COH102 to form an amide linkage (FIG. 18). These gels were comparable in performance to those formed from COH102 and COH206. (For proper reaction in the presence of methylated collagen, the COH204 had to be titrated to pH 2–4 during the mixing of reagents; on addition of curing buffer, its pH was increased, permitting the reaction of the amino group). It appeared that the presence of the succinimidyl ester was important for achieving the highest adhesion to the tissue substrate and for good tensile strength of the gel. Other groups that react with amines, such as aldehydes (aldehydes conjugated to multi-armed PEG), are also anticipated to be effective adhesive-forming reagents.

TABLE 17

Bond Strengths of Various Functionalized PEGs Filled with Vicryl Threads

| Material Strength | Incubation Time (Hrs.) | Bond (N Force) |
|---|---|---|
| COH206/Methylated Collagen/Vicryl/$H_2O_2$ | 17 | 0.32, 0.20 |
| COH206/4arm vinyl 2 sulfone PEG/Methylated Collagen/Vicryl threads | 2 | 2.2, 1.5 |
| COH102/206/204/ Methylated Collagen Vicryl threads | 2 | 6.4 |
| COH102/204/ Methylated collagen/ Vicryl threads | 4 | 3.6, 6.4 |
| COH102/206/ Methylated collagen/ Vicryl threads | 2 | 6.6, 5.6 |

Figure 19:
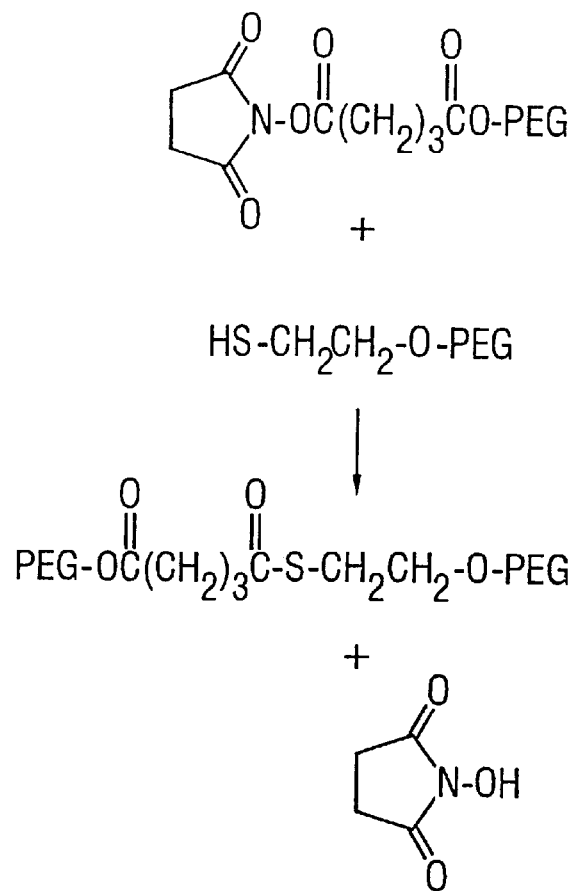
FIG. 19 illustrates the formation of a thioester-linked PEG conjugate resulting from reaction of succinimidyl-PEG with thiol-PEG.

Persistence of the Bond Under Hydrated Conditions:

Table 18 shows that the adhesives formed from COH102, COH206, and also COH204 form bonds using cowhide that persist for long times immersed in saline buffer at 37° C. Such stringent hydrated conditions simulate the in vivo environment. Bond weakening was observed after more than 100 hours of hydration. The weakening of bond strength was thought to be due to hydrolysis of carboxyl-ester and thioester (FIG. 19) network linkages. COH102 is a glutaryl-succinimidyl ester, even after reaction with the terminal carboxyl of the succinimidyl ester, there remains a carboxyl ester linking the glutaryl moiety to the main PEG chain; this bond, as well as the thio-ester bond, could hydrolyze.

TABLE 18

Bond Performance Under Long Hydration Times

| Material | Incubation Time (Hrs.) | Bond Strength (N Force) |
|---|---|---|
| COH102/206/204/ Methylated collagen/ Vicryl threads | 2 | 6.4 |
| | 66 | 2.6, 4.1 |
| | 70 | 3.0 |
| | 137 | 0.70, 2.6 |
| | 140 | 1.1, 0.4 |
| COH102/204/ Methylated collagen/ Vicryl threads | 4 | 3.6, 6.4 |
| | 64 | 7.0, 5.1 |
| | 136 | 3.8, 2.7 |
| | 234 | 2.7, 1.7 |
| COH102/206/ Methylated collagen/ Vicryl threads | 2 | 6.6, 5.6 |
| | 17 | 6.3, 5.5 |
| | 69 | 0.63, 0.90, 3.4, 5.4 |
| | 93 | 2.4, 5.4 |
| | 140 | 3.2, 2.9 |
| | 235 | >2.4, 3.7 |

Related Formulas with Lower Molecular Weight Compounds Bearing Succinimidyl Ester and Amino or Thiol Reactive Groups:

Table 19 presents bond strengths on cowhide strips of lower molecular weight PEG derivatives as adhesives, again supplemented with methylated collagen and Vicryl. GLYC-20HS is a tri-functional succinimidyl-succinate of a 3-armed PEG built from a glycerol core, 2600 mol. wt., NOF Corporation, Japan. COH201 is a tetra-amino, 4-armed PEG, 2000 mol. wt., Shearwater Polymers. The polymers were Vicryl filling appeared to have a small effect on bond strength. The following proportions were used: Methylated Collagen, 500 µl (22 mg/ml in water 2707–30B); GLYC-20HS, 48 mg; COH201, 60 µl of 60% solution in water, titrated to pH 1–2 with 6M HCl Vicryl threads, 26 mg.

TABLE 19

Low Molecular Weight Analogues to COH102 and COH206

| Materials | Incubation Time (Hrs.) | Bond Strength (N Force) |
|---|---|---|
| GLYC-20HS/ COH201/Methylated Collagen | 2 | 2.3, 0.64 |
| GLYC-20HS/ COH201/Methylated Collagen/Vicryl threads | 5 | 2.3, 3.3 |

Burst Tests on Collagen Disks and on Slit Defects in Carotid Arteries:

Performance of adhesives intended for use in surgical applications is often measured by their ability to seal fluid leaks. Two types of leaks, or fluid pressure tests were employed:

a. The Burst Test on a Collagen Disk

Figure 20:
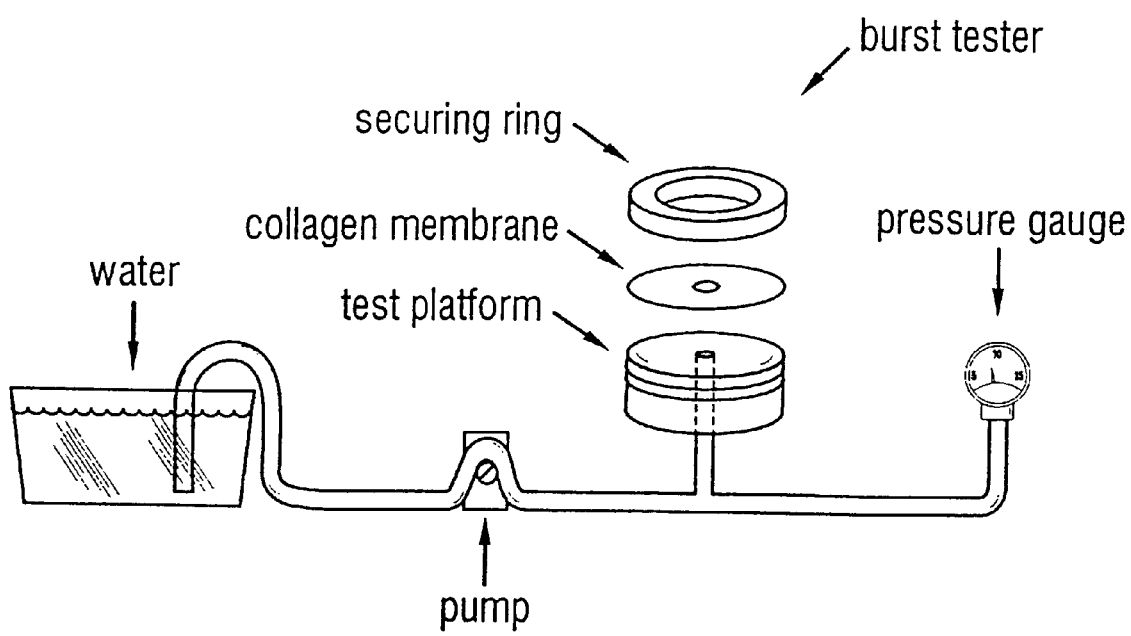
FIG. 20 depicts a device that is useful to test burst strength of a collagen membrane.

Using the device depicted in FIG. 20, collagen mat was mounted on a brass platform and secured with a second brass ring threaded to the first. The lower brass platform was perforated and connected to a line filled with water. Water was driven by a syringe pump at 5 ml/min. A shunt line led to a pressure gauge. The test collagen mat was also perforated (2 mm diameter hole). The adhesive preparation (approx. 0.5 ml) was applied to the mat, covering the perforation. The adhesive was allowed to cure 3 min (or longer, if necessary to effect cure to a firm rubber), then water pressure was applied. The pressure necessary to rupture the seal was recorded. For cyanoacrylate, a small (4×4 mm) piece of collagen mat was glued to the lower perforated mat.

b. Slit Defect on Carotid Artery

Figure 21:
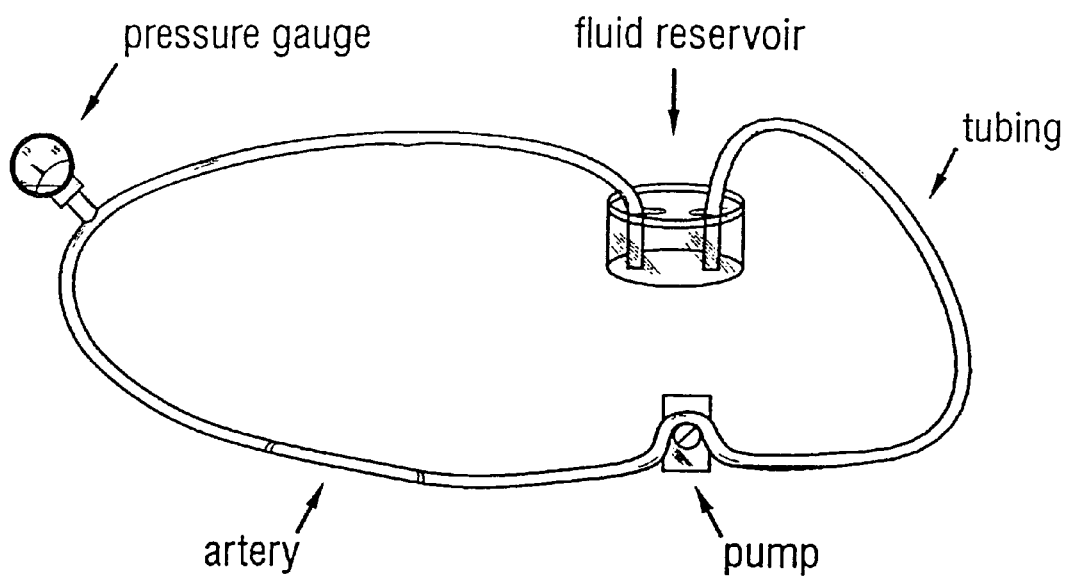
FIG. 21 illustrates a device (a pressurized carotid artery model) that is useful to test burst strength of a repaired artery slit defect.

The pressurized carotid artery model is illustrated in FIG. 21. A porcine artery (Pel Freeze Biologicals, Rogers, Ark.) was connected to a water line. Water was driven by a peristaltic pump. The end of the line had a flow restricter placed on it so that pressures up to 10 psi and more could be imposed on the line by increasing the pump speed. First the intact artery was placed in the system and subjected to water pressure, to assure that it would sustain desired pressures without leaking. Sections of artery devoid of side branches were preferred; leaking branches sometimes were clamped off to stop leaks. Slits approximately 2 mm long were cut transversely in the artery at four sites on a circumference. The cut artery then simulated an anastomosis to, which stay sutures had been applied. The cut sites were then glued all around in an attempt to seal them. Buffer (134 mM sodium acid phospate and 166 mM sodium carbonate, pH 8.9) was applied to the artery tissue just before the glue was applied. The glue mass was further irrigated with a few drops of this buffer to cure the gel. After 8 min cure time, the glued joint was subjected to water pressure. Pressure was increased at 1 psi increments and held at each pressure for 1 minute before increasing further. A leak was scored as positive if it was dripping faster than 1 drop every 10 seconds.

Table 20 shows the burst strengths of COH102/206/ methylated collagen/Vicryl on holes of varying diameters (on collagen membranes at 8 min cure time; cured with pH 8.9 buffer; 0.5 ml sample spread over hole with spatula). A hole with a diameter of 5 mm is the largest defect one might contemplate in a surgical application, since stay sutures would be used to close the largest defects, and the largest interval between such sutures was estimated to be 5 mm. Even with such large holes, the adhesive was able to sustain pressures near or above the maximum expected in hypertensive patients, i.e., 4 psi. The third data entry emphasizes the need to have good gel curing at the inter-face of gel and collagen disk. The addition of curing buffer to this surface prior to application improves the short-term bonding.

TABLE 20

Burst Strength of COH102/206/methylated Collagen/Vicryl

| Diameter of Orifice (mm) | Burst Pressure (PSI)* |
|---|---|
| 2 | >3.0, 7.4, 4.6 |
| 5 | 3.1, 5.5, 5.3 |
| 5 | 1.0 |

*1 PSI = 0.68 N/CM$^2$ = 51 mm Hg
4 PSI = 2.7 N/CM$^2$ = 204 m Hg
+Membrane not pre-treated with a drop of pH 8.9 buffer Table 21 presents data on closing large slit defects in carotid arteries (4×2 mm slits cut on 4–6 mm diameter artery). The COH102/206/methylated collagen/Vicryl formula was comparable to cyanoacrylate in performance. It should be noted that poorer results are seen on thinner arteries that stretch more under pressure.

TABLE 21

Burst Strength Test on Porcine Carotid Artery

| Material | Burst Pressure (PSI) | Cure Time (min.) |
|---|---|---|
| COH102/206/ Methylated Collagen/ Vicryl | 4.3 ± 2.0 (n = 5) 8.0 ± 4.0 (n = 3) | 8 30 |
| Cyanoacrylate (Elmer's Products) | 2.7 ± 3.6 (n = 6) | 8 |
| Cyanoacrylate (Dermabond) | 5.5 ± 5.2 (n = 4) | 8 |

EXAMPLE 12

0.40 g (0.04 mmol) of COH206 (4-armed thiol of PEG, penta-erythritol core, MW 10K) and 0.21 g (0.053 mmol) of trimethylolpropane tris(3-mercaptopropionate) were dissolved in 0.2 g of H$_2$O. The mixture of these two thiols was deprotonated by adding 0.5 mg of T403 (polyoxypropylene triamine). Upon mixing the solution with 0. 112 g (0.16 mmol) of poly (ethylene glycol) diacrylate (MW 700) a gel was formed within 2 minutes.

What is claimed is:

1. A crosslinkable system comprising
at least three biocompatible, reactive compounds each comprised of a molecular core having at least one functional group attached thereto through a direct covalent bond or through a linking group, wherein under reaction-enabling conditions each reactive compound is capable of substantially immediate covalent reaction with at least one other of the plurality of reactive compounds by virtue of the at least one functional group, and further wherein:
each molecular core is selected from the group consisting of synthetic hydrophilic polymers, naturally occurring hydrophilic polymers, hydrophobic polymers, and C$_2$–C$_{14}$ hydrocarbyl groups containing zero to 2 heteroatoms selected from N, O, S and combinations thereof;
at least one of the molecular cores is a synthetic hydrophilic polymer; and
at least two of the molecular cores contain at least two functional groups.

2. The crosslinkable system of claim 1, wherein:
(a) a first crosslinlable compound A has m nucleophilic groups, wherein m≧2;
(b) a second crosslinkable compound B has n electrophilic groups capable of reaction with the m nucleophilic groups to form covalent bonds, wherein n≧2 and m+n>4; and
(c) a third crosslinkable compound C has at least one functional group selected from (i) nucleophilic groups capable of reacting with the electrophilic groups of compound B and (ii) electrophilic groups capable of reacting with the nucleophilic groups of compound A, wherein the total number of functional groups on compound C is represented by p, such that m+n+p>5, wherein compounds A, B and C are combined in a single composition.

3. The system of claim 2, wherein p>2.

4. The system of claim 2, wherein the m nucleophilic groups are identical.

5. The system of claim 3, wherein the m nucleophilic groups are identical.

6. The system of claim 2, wherein at least two of the m nucleophilic groups are different.

7. The system of claim 2, wherein the n electrophilic groups are identical.

8. The system of claim 5, wherein the n electrophilic groups are identical.

9. The system of claim 2, wherein at least two of the n electrophilic groups are different.

10. The system of claim 2, wherein the at least one functional group on compound C is nucleophilic.

11. The system of claim 5, wherein the functional groups on compound C are nucleophilic.

12. The system of claim 11, wherein the functional groups on compound C are the same as the m nucleophilic groups on compound A.

13. The system of claim 11, wherein at least one of the functional groups on compound C is different than the m nucleophilic groups on compound A.

14. The system of claim 2, wherein the at least one functional group on compound C is electrophilic.

15. The system of claim 14, wherein the functional groups on compound C are electrophilic.

16. The system of claim 15, wherein the functional groups on compound C are the same as the n electrophilic groups on compound B.

17. The system of claim 15, wherein at least one functional group on compound C is different than the n electrophilic groups on compound B.

18. The system of claim 2, wherein compound A has the structural formula (I), compound B has the structural formula (II), and compound C has the structural formula (III)

  (I)
  (II)
  (III)

wherein:
R$^1$, R$^2$ and R$^3$ are independently selected from the group consisting of C$_2$ to C$_{14}$ hydrocarbyl, heteroatom-containing C$_2$ to C$_{14}$ hydrocarbyl, hydrophilic polymers, and hydrophobic polymers, providing that at least one of R$^1$, R$^2$ and R$^3$ is a hydrophilic polymer;
X represents one of the m nucleophilic groups of compound A;

Y represents one of the n electrophilic groups of compound B;

Fn represents a functional group on compound C;

$Q^1$, $Q^2$ and $Q^3$ are linking groups;

q, r and s are independently zero or 1; and m, n and p are as defined previously.

19. The system of claim 18, wherein:
(a) $R^1$ is a first synthetic hydrophilic polymer;
(b) $R^2$ is selected from the group consisting of (i) a second synthetic hydrophilic polymer that may or may not be the same as $R^1$ and (ii) $C_2$ to $C_{14}$ hydrocarbyl groups containing zero to 2 heteroatoms selected from N, O and S; and
(c) $R^3$ is selected from the group consisting of (i) a third synthetic hydrophilic polymer that may or may not be the same as $R^1$ or $R^2$ and (ii) $C_2$ to $C_{14}$ hydrocarbyl groups containing zero to 2 heteroatoms selected from N, O, S and combinations thereof.

20. The system of claim 17, wherein the synthetic hydrophilic polymer is of a linear, branched, dendrimeric, hyperbranched, or star polymer.

21. The system of claim 19, wherein the synthetic hydrophilic polymer is selected from the group consisting of: polyalkylene oxides; polyglycerols; poly(oxyalkylene)-substituted polyols; polyacrylic acid and analogs thereof; polymaleic acid; polyacrylamides; poly(olefinic alcohol)s; poly(N-vinyl lactams); polyoxazolines; polyvinylamines; and copolymers thereof.

22. The system of claim 21, wherein the synthetic hydrophilic polymers is a polyalkylene oxide or polyglycerol.

23. The system of 22, wherein the synthetic hydrophilic polymer is a polyalkylene oxide is selected from the group consisting of polyethylene glycol and poly(ethylene oxide)-poly(propylene oxide) copolymers.

24. The system of claim 23, wherein the polyalkylene oxide is polyethylene glycol.

25. The system of claim 21, wherein the synthetic hydrophilic polymer is a poly(oxyalkylene)-substituted diol or polyol.

26. The system of claim 25, wherein the synthetic hydrophilic polymer is selected from the group consisting of mono-poly(oxyalkylene)-substituted propylene glycol, di-(polyoxyalkylene)-substituted propylene glycol, mono-poly(oxyalkylene)-substituted trimethylene glycol, di-(polyoxyalkylene)-substituted trimethylene glycol, mono-poly(oxyalkylene)-substituted glycerol, di-(polyoxyalkylene)-substituted glycerol, and tri-(polyoxyalkylene)-substituted glycerol.

27. The system of claim 21, wherein the synthetic hydrophilic polymer is selected from the group consisting of poly(acrylic acid) and analogs and copolymers thereof.

28. The system of claim 27, wherein the synthetic hydrophilic polymer is selected from the group consisting of poly(acrylic acid), poly(methacrylic acid), poly(hydroxyethylmethacrylate), poly(hydroxyethylacrylate), poly(methylalkylsulfoxide acrylates), poly(methylalkylsulfoxide methacrylates), and copolymers thereof.

29. The system of claim 21, wherein the synthetic hydrophilic polymer is polymaleic acid.

30. The system of claim 21, wherein the synthetic hydrophilic polymer is a polyacrylarnide.

31. The system of claim 30, wherein the synthetic hydrophilic polymer is selected from the group consisting of polyacrylamide, poly(methacrylamide), poly(dimethylacrylamide), poly(N-isopropylacrylamide), and copolymers thereof.

32. The system of claim 21, wherein the synthetic hydrophilic polymer is a poly(olefinic alcohol).

33. The system of claim 32, wherein the poly(olefinic alcohol) is polyvinyl alcohol or a copolymer thereof.

34. The system of claim 21, wherein the synthetic hydrophilic polymer is a poly(N-vinyl lactam).

35. The system of claim 24, wherein the poly(N-vinyl lactam) is selected from the group consisting of poly(vinyl pyrrolidone), poly(vinyl caprolactam), and copolymers thereof.

36. The system of claim 19, wherein at least one of $R^2$ and $R^3$ is $C_2$ to $C_{14}$ hydrocarbyl containing zero to 2 heteroatoms selected from N, O and S.

37. The system of claim 36, wherein at least one of $R^2$ and $R^3$ is $C_2$ to $C_{14}$ hydrocarbyl.

38. The system of claim 19, wherein r, s and t are zero.

39. The system of claim 19, wherein at least one of r, s and t is 1.

40. The system of claim 19, wherein one or more of $Q^1$, $Q^2$ and $Q^3$ contains at least one biodegradable linkage.

41. The system of claim 40, wherein the biodegradable linkage is a hydrolyzable linkage.

42. The system of claim 40, wherein the biodegradable linkage is an enzymatically cleavable linkage.

43. The system of claim 41, wherein the biodegradable linkage is an enzymatically hydrolyzable linkage.

44. The system of claim 2, wherein the nucleophilic groups on compound A and any nucleophilic groups on compound C are selected from the group consisting of $-NH_2$, $-NHR^4$, $-N(R^4)_2$, $-SH$, $-OH$, $-COOH$, $-C_6H_4-OH$, $-PH_2$, $-PHR^5$, $-P(R^5)_2$, $-NH-NH_2$, $-CO-NH-NH_2$, and $-C_5H_4N$, where $R^4$ and $R^5$ are $C_1-C_{12}$ hydrocarbyl.

45. The system of claim 44, wherein the nucleophilic groups are selected from $-NH_2$ and $-NHR^4$ where $R^4$ is lower hydrocarbyl.

46. The system of claim 45, wherein the electrophilic groups on compound B and any electrophilic groups on compound C are amino-reactive groups.

47. The system of claim 46, wherein the amino-reactive groups contain an electrophilically reactive carbonyl group susceptible to nucleophilic attack by a primary or secondary amine.

48. The system of claim 47, wherein the amino-reactive groups are carboxylic acid esters.

49. The system of claim 47, wherein the amino-reactive groups are carboxylic acids or aldehydes.

50. The system of claim 46, wherein the amino-reactive groups are selected from the group consisting of succinimidyl ester, sulfosuccinimidyl ester, maleimido, epoxy, isocyanato, thioisocyanato, and ethenesulfonyl.

51. The system of claim 44, wherein the nucleophilic groups are sulfhydryl groups.

52. The system of claim 51, wherein the electrophilic groups on compound B and any electrophilic groups on compound C are sulihydryl-reactive groups.

53. The system of claim 52, wherein the sulfhydryl-reactive groups are selected so as to form a thioester, thioether, or disulfide linkage upon reaction with the sulfhydryl groups.

54. The system of claim 52, wherein the sulfhydryl-reactive groups contain an electrophilically reactive carbonyl group susceptible to nucleophilic attack by sulfhydryl group.

55. The system of claim 54, wherein the sulfhydryl-reactive groups are carboxylic acid esters.

56. The system of claim 54, wherein the amino-reactive groups are carboxylic acids or aldehydes.

57. The system of claim 52, wherein the sulfhydryl-reactive groups have the structure —S—S—Ar where Ar is a substituted or unsubstituted nitrogen-containing heteroaromatic moiety or a non-heterocyclic aromatic group substituted with an electron-withdrawing moiety.

58. The system of claim 52, wherein the sulfhydryl-reactive groups are selected from the group consisting of succinimidyl ester, sulfosuccinimidyl ester, maleimido, epoxy, and ethenesulfonyl.

59. The system of claim 2, further including at least one additional crosslinkable compound D having at least one functional group selected from nucleophilic groups and electrophilic groups, and the total number of functional groups on compound D is represented by q, such that $q \geq 1$.

60. The system of claim 48, wherein $q \geq 2$.

61. The crosslinkable system of claim 1, wherein each reactive compound is comprised of a molecular core having at least two functional groups covalently attached thereto.

62. The crosslinkable system of claim 1, wherein the functional groups of at least one of the reactive compounds are hydroxyl or sulfhydryl groups and the functional groups of at least one other of the reactive compounds are electrophilic groups capable of undergoing reaction with the hydroxyl or sulfhydryl groups to form covalent bonds, such that upon admixture of the compounds with an aqueous base, a biocompatible crosslinked material is formed.

63. The crosslinkable system of claim 62, wherein at least one of the molecular cores is comprised of a $C_2$–$C_{14}$ hydrocarbyl group containing zero to 2 heteroatoms selected from N, O, S and combinations thereof, and at least one other of the molecular cores is comprised of a naturally occurring hydrophilic polymer.

64. The crosslinkable system of claim 1, wherein: a first reactive compound comprises a synthetic hydrophilic polymer having at least two primary amino groups attached thereto; a second reactive compound comprises a synthetic hydrophilic polymer having at least two amine-reactive electrophilic groups attached thereto; and a third reactive compound comprises a $C_2$–$C_{14}$ hydrocarbyl group containing zero to 2 heteroatoms selected from N, O, S and combinations thereof, and substituted with at least one functional group capable of undergoing reaction with the primary amino groups or the amine-reactive electrophilic groups.

65. The crosslinkable system of claim 1, wherein: a first reactive compound comprises a synthetic hydrophilic polymer having at least two sulihydryl groups attached thereto; a second reactive compound comprises a synthetic hydrophilic polymer having at least two sulfhydryl-reactive electrophilic groups attached thereto; and a third reactive compound comprises a $C_2$–$C_{14}$ hydrocarbyl group containing zero to 2 heteroatoms selected from N, O and combinations thereof, and substituted with at least one functional group capable of undergoing reaction with the sulfhydryl groups or the sulfhydryl-reactive groups.

66. A crosslinked composition prepared by admixing the system of claim 1, with an aqueous solution, with the proviso that if the nucleophilic groups on compound A or the functional groups on compound C are hydroxyl or thiol groups, the aqueous solution contains a base.

67. The composition of claim 66, wherein the base is a non-nucleophilic base.

68. The composition of claim 66, further including a therapeutically effective amount of a biologically active agent.

69. The composition of claim 68, wherein the biologically active agent is selected from the group consisting of: enzymes, receptor antagonists, receptor agonists, hormones, growth factors, autogenous bone marrow, antibiotics, antimicrobial agents, antibodies, cells and genes.

70. The composition of claim 69, wherein the biologically active agent is a growth factor or a derivative, analog or fragment thereof.

71. The composition of claim 69, wherein the biologically active agent is a cell.

72. The composition of claim 69, wherein the biologically active agent is a gene.

73. The crosslinkable system of claim 1, wherein each crosslinkable compound is physically segregated from each other crosslinkable compound.

74. The crosslinkable system of claim 73, wherein compound A is contained in a sterile aqueous medium.

* * * * *

UNITED STATES PATENT AND TRADEMARK OFFICE
CERTIFICATE OF CORRECTION

PATENT NO.    : 6,458,889 B1
DATED         : October 1, 2002
INVENTOR(S)   : Trollsas et al.

It is certified that error appears in the above-identified patent and that said Letters Patent is hereby corrected as shown below:

<u>Column 53,</u>
Line 14, please change "$q \gneq$" to -- $q \geq$ --.

Signed and Sealed this

First Day of April, 2003

JAMES E. ROGAN
*Director of the United States Patent and Trademark Office*